(12) United States Patent
Zeng

(10) Patent No.: US 9,790,503 B2
(45) Date of Patent: *Oct. 17, 2017

(54) VHZ FOR DIAGNOSIS AND TREATMENT OF CANCER

(71) Applicant: **AGENCY FOR SCIENCE, TECHNOLOGY AND RESEARCH (A*STAR)**, Singapore (SG)

(72) Inventor: Qi Zeng, Singapore (SG)

(73) Assignee: **AGENCY FOR SCIENCE, TECHNOLOGY AND RESEARCH (A*STAR)**, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 14/276,203

(22) Filed: May 13, 2014

(65) Prior Publication Data

US 2014/0242092 A1   Aug. 28, 2014

Related U.S. Application Data

(63) Continuation of application No. 12/672,902, filed as application No. PCT/SG2008/000294 on Aug. 8, 2008, now Pat. No. 8,765,388.

(60) Provisional application No. 60/935,406, filed on Aug. 10, 2007.

(51) Int. Cl.

| A61K 39/00 | (2006.01) |
|---|---|
| C07K 16/30 | (2006.01) |
| C12N 15/113 | (2010.01) |
| C07K 16/40 | (2006.01) |
| C12N 9/12 | (2006.01) |
| C12N 9/16 | (2006.01) |
| C12Q 1/42 | (2006.01) |
| G01N 33/574 | (2006.01) |
| C12Q 1/44 | (2006.01) |

(52) U.S. Cl.
CPC .......... *C12N 15/1137* (2013.01); *C07K 16/40* (2013.01); *C12N 9/1205* (2013.01); *C12N 9/16* (2013.01); *C12Q 1/42* (2013.01); *C12Q 1/44* (2013.01); *G01N 33/57415* (2013.01); *G01N 2333/916* (2013.01); *G01N 2800/52* (2013.01); *G01N 2800/56* (2013.01)

(58) Field of Classification Search
None
See application file for complete search history.

(56) References Cited

U.S. PATENT DOCUMENTS 5,861,155 A    1/1999 Lin
6,649,391 B1 * 11/2003 Luche et al. .................. 435/196

FOREIGN PATENT DOCUMENTS

| SG | 159086 | 5/2013 |
|---|---|---|
| WO | 01/05983 A | 1/2001 |
| WO | 0112819 A2 | 2/2001 |
| WO | 01/20004 A | 3/2001 |
| WO | 02/095012 A1 | 11/2002 |
| WO | 2009/022988 A2 | 2/2009 |

OTHER PUBLICATIONS

Robert A. Weinberg ("Weinberg", The Biology of Cancer, 2nd Ed. Chapter 2. The Nature of Cancer, pp. 31-69).*
Radke et al. ("Radke", Br.J. Cancer, 2006, 95 (3), 347-354).*
Cancer Drug Design and Discovery Neidle, Stephen, ed. (Elsevier/Academic Press, 2008) p. 427-431.*
Jain RK (Scientific American, Jul. 1994, 58-65).*
Gura, Science Nov. 7, 1997: vol. 278, p. 1041-1042.*
Sporn et al, "Chemoprevention of Cancer," Carcinogenesis, vol. 21 (2000), 525-530.*
Gao et al. ("Gao", May 2008, Cancer Bio. & Therapy, 7, 752-759, Exhibit A, Affidavit filed Mar. 8, 2016).*
Alonso, A. et al., Cell, 117(6):699-711 (2004). "Protein tyrosine phosphatase in the human genome."
Qihan, W. et al., 36:1542-1553 (2004). "Molecular cloning and characterisation of a novel dual-specificity phosphatase 23 gene from human fetal brain."
Alonzo et al., The Journal of Biological Chemistry, 279(34): 35768-35774 (2004). "The Minimal Essential Core of a Cysteine-based Protein-tyrosine Phosphatase Revealed by a Novel 16-kDa VH1-like Phosphatase, VHZ."
Takagaki et al., The Biochemical Journal, 383:447-455 (2004). "Characterization of a Novel Low-Molecular-Mass Dual-Specificity Phosphatase-3 (Ldp-3) That Enhances Activation of Jnk and P38."
Agarwal et al., "Structure of human dual specificity protein phosphatese 23, VHZ, enzyme-substrate/product complex", Journal of Biological Chemistry, 283(14):8946-8953 (2008).
Bergers et al., "Extrinsic regulators of epithelial tumor progression: metalloproteinases", Current Opinion in Genetics and Development 10:120-127 (2000).
Bernard et al. "A Unique Epitope on the CD2 molecule defined by the monoclonal antibody 9-1: Epitope-specific modulation of the E-Rosette receptor and effects on t-cell functions", Human Immunol. 17:388-405 (1986).
Caldas et al., "Humanization of the anti-CD18 antibody 6.7: an unexpected effect of a framework residue in binding to antigen", Mol. Immunol 39(15):941-952 (2003).
Carter et al., "Potent antibody therapeutics by design", Reviews, 6:343-357 (2006).
Casset et al. "A peptide mimetic of an anti-CD4 monoclonal antibody by rational design", Biochem Biophys Res. Commun 307(1):198-205 (2003).

(Continued)

Primary Examiner — Mark Halvorson
Assistant Examiner — Kauser Akhoon
(74) Attorney, Agent, or Firm — Nixon Peabody LLP; Mark J. FitzGerald; Srividya Subramanian

(57) ABSTRACT

We provide VHZ for use in a method of treatment, prophylaxis or alleviation of a cancer, such as breast cancer, in an individual. We provide an anti-VHZ agent for the treatment, prophylaxis or alleviation of cancer. We further provide a kit for detecting breast cancer in an individual or susceptibility of the individual to breast cancer comprising means for detection of VHZ expression in the individual or a sample taken from him or her as well as a method of detecting a cancer cell, the method comprising detecting modulation of expression, amount or activity of VHZ in the cell.

7 Claims, 40 Drawing Sheets

(56) References Cited

OTHER PUBLICATIONS

Chien et al., "Significant structural and functional change of an antigen-binding site by a distant amino acid substitution: proposal of a structural mechanism", PNAS 86(14):5532-5536 (1989).
Dennis C., "Off by a whsiper", Nature. 442:739-741 (2006).
Depascalis et al., "Grafting of "Abbreviated" complementarity-determining regions containing specificity-determining residues essential for ligand contact to engineer a less immunogenic humanized monoclonal antibody", J. Immol. 169(6):3076-3084 (2002).
Ferrone et al., "Hidden immunotherapy targets challenge dogma", Cancer, 3(99):1-3 (2011).
George et al., "Differential effects of anti-beta2-glycoprotein I antibodies on endothelial cells and on the manifestations of experimental antiphospholipid syndrone", Circulation 97:900-906 (1998).
Guisti et al., "Somatic diversification of S107 from an antiphosphocholine to an anti-DNA autoantibody is due to a single base change i its heavy variable region", PNAS 84(9):2926-2930 (1987).
Guo et al., "Targeting intracellular oncoproteins with antibody therapy or vaccination", Science Translational Medicine 3(99ra85):1-10 (2011).
Gussow et al., Humanization of monoclonal antibodies, Methods in Enzymology, 203:99-121 (1991).
Hara et al., "Interleukin-2 potentiation of cetuximad antitumor activity for epidermal growth factor receptor-overexpressing gastric cancer xenografts through antibody-dependent cellular cytotoxicity", Cancer Sci. 99(7):1471-1478 (2008).
Holm et l., "Functional mapping and single chain construction of the anti-cytokeratin 8 monoclonal antibody TS1", Mol. Immuol 44(6):1075-1084 (2007).
Imai et al., "Comparing antibody and small-molecule therapies for cancer", Reviews, vol. 6, 714-727 (2006).
Jiang et al., "A novel peptide isolated from a phage display peptide library with trastuzumab can mimic antigen epitope of HER-2", J. Biol Chem 280(6):4656-4662 (2005).
Kelland et al., "Of mice and Men": values and liabilites of the athymic nude mouse model in anticancer drug development, Eur. J. Cancer. 40(6):827-836 (2004).
MacCallum et al., "Antibody-antigen interactions: Contact analysis and binding site topography", J. Mol. Biol 262(5):732-745 (1996).
Mariuzza et l., "The structure basis of antigen-antibody recognition", Annu Rev. Biophys. Biohys. Chem. 16:139-159 (1987).
Muller et al., "TransMabs: cell-penetrating antibodies, the next generation", Expert Opinion Biol. Ther. 5(2):237-241 (2005).
Pettersen et al., "CD47 signals T cell death", J. Immunol 162(12):7031-7040 (1999).
Rudikoff et al., "Single amino acid substitution altering antigen-binding specificity", PNAS 79:1979-1983 (1982).
Saijo et al., "What are the reasons for negative phase III trials of molecular-target-based drugs?", Cancer Sci. 95(10):772-776 (2004).
Stancovski et al., "Mechanistic aspects of the opposing effects of monoclonal antibodies to the ERBB2 receptor on tumor growth", PNAS 88:8691-8695 (1991).
Vajdos et al., "Comprehensive functional maps of the antigen-binding site of an anti-ErbB2 antibody obtained with shotgun scanning mutagenesis", J. Mol. Biol. 320(2):415-428.
Winkler et al., "Changing the antigen binding specificity by single point mutations of an anti-p24 (HIV01) antibody", J. Immunol. 165(8):4505-4514 (2000).
Labbe et al., "Protein tyrosine phosphatases in cancer: friends and foes!", Prog Mol Biol Transl Sci., 106(16):253-306 (2012).
Tang et al., "VHZ is a novel centrosomal phosphatase associated with cell growth and human primary cancers", Molecular Cancer, 9:128 (2010).

* cited by examiner

VHZ-EGFP

Pericentrin

MCF-VHZ(C95S)-EGFP

MCF-EGFP Vector

E-Cadherin

FIGURE 6B  MCF-VHZ-EGFP
0 hr
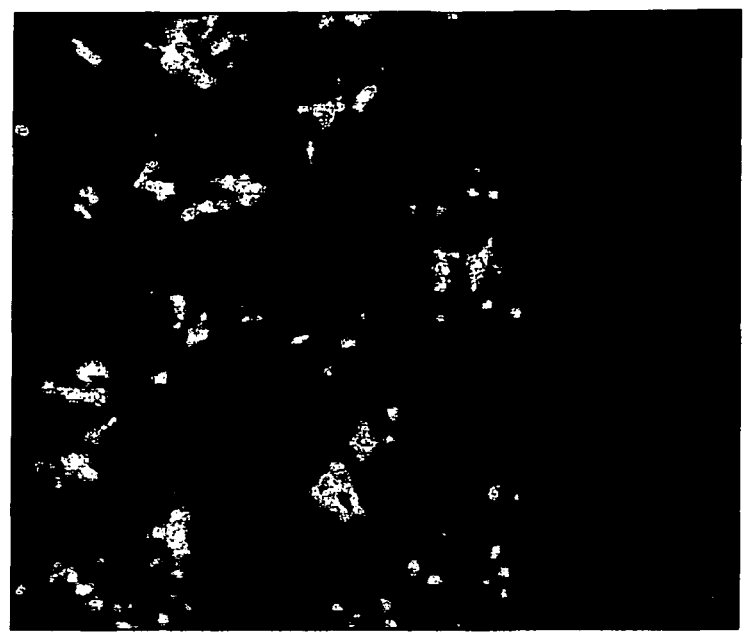
48 hr

MCF-VHZ (C95S)-EGFP

FIGURE 7B

|   | 1 | 2 | 3 | 4 | 5 | 6 | 7 | 8 | 9 | 10 | 11 | 12 |
|---|---|---|---|---|---|---|---|---|---|---|---|---|
| A | whole brain | cerebellum left | | heart | esophagus | colon transverse | kidney | lung | liver | leukemia HL-60 | fetal brain | yeast total RNA |
| B | cerebral cortex | cerebellum right | accumbens nucleus | aorta | stomach | colon descending | skeletal muscle | placenta | pancreas | Hela S3 | fetal heart | yeast tRNA |
| C | frontal lobe | corpus callosum | thalamus | atrium left | duodenum | rectum | spleen | bladder | adrenal gland | leukemia K-562 | fetal kidney | *E.coli* rRNA |
| D | parietal lobe | amygdala | | atrium right | jejunum | | thymus | uterus | thyroid gland | leukemia MOLT-4 | fetal liver | *E.coli* DNA |
| E | occipital lobe | caudate nucleus | spinal cord | ventricle left | ileum | | peripheral blood leukocyte | prostate | salivary gland | Burkitt's lymphoma Raji | fetal spleen | Poly r(A) |
| F | temporal lobe | hippocampus | | ventricle right | ilocecum | | lymph node | testis | | Burkitt's lymphoma Daudi | fetal thymus | human Cot I DNA |
| G | p.g.of cerebral cortex | medulla oblongata | | inter-ventricle septum | appendix | | bone marrow | ovary | | colorectal adenocarcinoma SW480 | fetal lung | human DNA 100ng |
| H | pons | putamen | | apex of the heart | colon ascending | | trachea | | | lung carcinoam A549 | | human DNA 500ng |

SEQUENCE LISTING

```
<160> NUMBER OF SEQ ID NOS: 9

<210> SEQ ID NO 1
<211> LENGTH: 718
<212> TYPE: DNA
<213> ORGANISM: Homo sapiens

<400> SEQUENCE: 1
gtggcccggg aggcgccgag gccagcgatg ggcgtgcagc cccccaactt ctcctgggtg      60
cttccgggcc ggctggcggg actggcgctg ccgcggctcc ccgcccacta ccagttcctg     120
```

```
ttggacctgg gcgtgcggca cctggtgtcc ctgacggagc gcgggccccc tcacagcgac    180
agctgccccg gcctcaccct gcaccgcctg cgcatccccg acttctgccc gccggccccc    240
gaccagatcg accgcttcgt gcagatcgtg gacgaggcca acgcacgggg agaggctgtg    300
ggagtgcact gtgctctggg ctttggccgc actggcacca tgctggcctg ttacctggtg    360
aaggagcggg gcttggctgc aggagatgcc attgctgaaa tccgacgact acgacccggc    420
tccatcgaga cctatgagca ggagaaagca gtcttccagt tctaccagcg aacgaaataa    480
ggggccttag taccctttcta ccaggccctc actccccttc ccatgttgt cgatggggcc    540 agagatgaag ggaagtggac taaagtatta aaccctctag ctcccattgg ctgaagacac    600
tgaagtagcc cacccctgca ggcaggtcct gattgaaggg gaggcttgta ctgctttgtt    660
gaataaatga gttttacgaa ccaggaaaaa aaaaaaaaaa aaaaaaaaaa aaaaaaa       718
```

<210> SEQ ID NO 2
<211> LENGTH: 150
<212> TYPE: PRT
<213> ORGANISM: Homo sapiens

<400> SEQUENCE: 2

```
Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
        35                  40                  45

His Ser Asp Ser Cys Pro Gly Leu Thr Leu His Arg Leu Arg Ile Pro
    50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150
```

<210> SEQ ID NO 3
<211> LENGTH: 15
<212> TYPE: PRT
<213> ORGANISM: Homo sapiens

<400> SEQUENCE: 3

```
Arg Arg Leu Arg Pro Gly Ser Ile Glu Thr Tyr Glu Gln Glu Lys
1               5                   10                  15
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<223> OTHER INFORMATION: See specification as filed for detailed -continued description of substitutions and preferred embodiments

<400> SEQUENCE: 4

His His His His His His His His His His
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgaattcac catgggcgtg cagcccccca acttctcc                              38

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtggatcccg tttcgttcgc tggtag                                           26

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccaaagccc agagcagagt gcactcccac agc                                   33

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Leu Arg Pro Gly Ser Ile Glu Thr Tyr Glu Gln Glu Lys
1               5                   10                  15

VHZ FOR DIAGNOSIS AND TREATMENT OF CANCER

CROSS REFERENCE TO RELATED APPLICATIONS

This application is a continuation application of U.S. Ser. No. 12/672,902 filed on Feb. 10, 2010, which is a 371 National Phase Entry Application of International Application No. PCT/SG2008/000294 filed Aug. 8, 2008, which designates the U.S., and which claims the benefit of priority under 35 U.S.C. §119(e) of U.S. Provisional No. 60/935,406 filed Aug. 10, 2007, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 26, 2015, is named 062915-067311-DIV_SL.txt and is 4,374 bytes in size.

FIELD

The present invention relates to the fields of medicine, cell biology, molecular biology and genetics. This invention relates to the field of medicine. In particular, it relates to treatment and diagnosis of diseases such as breast cancer, as well as compositions for such use.

BACKGROUND

VHZ is a phosphatase that shares about 28% amino acid sequence identity with human PRL-PTPs. VHZ was previously reported to be expressed in many tissues and located in the cytosol and in nucleoli (Alonso et al., 2004a).

However, the role of VHZ was largely unknown; despite its conservation through evolution with orthologues in frogs, fish, fly, and the Archaea. VHZ, as well as VHR, belongs to a separate subgroup of VH1-like PTPs (Alonso et al, 2004b). VHR has been reported to have a function in regulating cell cycle progression (Rahmouni et al., 2006).

In the Western world and the developed countries of Asia, breast carcinoma is the second leading cause of cancer-related death in women (Polyak, 2001). Breast cancer tops the cancer list for women in Singapore, with 700-800 new cases being diagnosed each year (Singapore Cancer Registry Report, 2000). In the USA, 180,000 women are diagnosed annually with new cases of breast cancer (Polyak, 2001). Despite better diagnosis and routine screening around a quarter of the cases will die from their disease.

Accordingly, there is a need for improved breast cancer detection and therapy.

SUMMARY

According to a $1^{st}$ aspect of the present invention, we provide VHZ for use in a method of treatment, prophylaxis or alleviation of a cancer, such as breast cancer, in an individual.

There is provided, according to a $2^{nd}$ aspect of the present invention, an anti-VHZ agent for the treatment, prophylaxis or alleviation of cancer. The cancer may comprise breast cancer. The cancer may comprise an invasive or metastatic cancer such as Invasive Ductal Carcinoma (IDC).

The anti-VHZ agent may be capable of down-regulating any combination of the expression, amount or activity of a VHZ sequence shown as GenBank accession number NM_017823 or NP_060293, or a sequence which has at least 90% sequence identity to that sequence. The anti-VHZ agent may comprise an anti-VHZ antibody.

The anti-VHZ antibody may comprise an anti-peptide antibody generated against RRLRPGSIETYEQEK (SEQ ID NO: 3) corresponding to amino acid residues (126-140) of human VHZ.

The anti-VHZ antibody may comprise chicken anti-human VHZ antibody (catalogue numbers LS-C32281, amino acids 35 to 90, LS-C42458, LS-A6806 and LS-A6803, LS-C32281, LifeSpan Inc, Seattle, Wash., USA), rabbit anti-human VHZ antibody (catalogue number DS-PB-00676, RayBiotech Inc, Norcross, Ga., USA), chicken anti-human VHZ antibody (catalogue number XW-7857, ProSci Incorporated, Poway, Calif., USA), rabbit anti-human VHZ antibody (catalogue number F4560 and D9840-66A, United States Biological, Swampscott, Mass., USA), chicken anti-human VHZ antibody (catalogue number D9840-66, United States Biological, Swampscott, Mass., USA), rabbit anti-human VHZ antibody (catalogue number AHP1142, AdB Serotec, Oxford, United Kingdom), rabbit anti-human VHZ antibody (catalogue number NB 110-40452, Novus Biologicals, Littleton, Colo., USA), chicken anti-human VHZ antibody (catalogue number NB 100-75328, Novus Biologicals, Littleton, Colo., USA).

The anti-VHZ agent may be capable of downregulating VHZ by RNA interference. It may comprise a Small Interfering RNA (siRNA), Short Hairpin RNA (shRNA) or Chimera RNAi such as a DUSP23 Pre-design Chimera RNAi (catalogue number H00054935-R01, Novus Biologicals, Littleton, Colo., USA).

We provide, according to a $3^{rd}$ aspect of the present invention, a kit for detecting breast cancer in an individual or susceptibility of the individual to breast cancer. The kit may comprise means for detection of VHZ expression in the individual or a sample taken from him or her. The means for detection may be selected from the group consisting of: a VHZ polynucleotide or a fragment thereof; a complementary nucleotide sequence to VHZ nucleic acid or a fragment thereof; a VHZ polypeptide or a fragment thereof, or an anti-VHZ antibody, or an anti-VHZ agent as set out above, and optionally instructions for use. It may further comprise a therapeutic drug for treatment, prophylaxis or alleviation of breast cancer, such as comprising Tamoxifen or Herceptin.

As a 4th aspect of the present invention, there is provided a method of detecting a cancer cell such as a breast cancer cell. The cancer cell may comprise invasive or metastatic cancer cell such as Invasive Ductal Carcinoma (IDC). The method may comprise detecting modulation of expression, amount or activity of VHZ in the cell. The modulation may comprise up-regulation. The expression of VHZ may be compared to the expression, amount or activity of VHZ in a control cell known to be non-cancerous.

The method may comprise detecting a VHZ nucleic acid. This may be by means of a probe comprising at least a portion of a nucleic acid having a sequence shown as GenBank accession number NM_017823 or NP_060293 or a sequence having at least 90% sequence identity to such a sequence, or in which the method comprises detecting a VHZ polypeptide, such as by means of an anti-VHZ antibody set out in claim 2.

The method may further comprise histological grading. The histological grading may be by means of the Elston- Ellis modified Scarff, Bloom, Richardson grading system (Nottingham Grading System (NGS)).

We provide, according to a 5th aspect of the present invention, a method of determining the proliferative state of a cell, or determining the likelihood that a cell will become invasive or aggressive. The method comprises detecting modulation of expression, amount or activity of VHZ in the cell.

The present invention, in a 6th aspect, provides a method of predicting a survival rate of an individual with cancer. The method comprises detecting modulation of expression of VHZ in a cell of the individual In a 7th aspect of the present invention, there is provided a method of choosing a therapy for an individual with cancer, the method comprising detecting modulation of expression of VHZ in a cell of the individual choosing an appropriate therapy based on the aggressiveness of the cancer. The therapy may comprise an anti-VHZ agent as described above.

According to an 8th aspect of the present invention, we provide a method of determining the likelihood of success of a particular therapy in an individual with a cancer. The method comprises comparing the therapy with a therapy determined by a method as set out above.

Each of these methods may further comprise a feature set out above in any of the 1st to 3rd aspects of the invention.

We provide, according to a 9th aspect of the invention, a method of manipulating a cancer cell, such as a breast cancer cell. The cancer cell may comprise an invasive or metastatic cancer cell such as Invasive Ductal Carcinoma (IDC). The method may comprise modulating the expression, amount or activity of VHZ in the cell. The modulation may comprise down-regulation. The method may comprise exposing the cell to an siRNA or shRNA capable of specifically binding to VHZ. It may comprise exposing the cell to an anti-VHZ antibody such as set out above. The cancer cell may become non-cancerous or the invasive or metastatic cancer cell may become non-invasive or non-metastatic as a result of the manipulation.

There is provided, in accordance with a 10th aspect of the present invention, a method of manipulating a cell, the method comprising the steps of: (a) detecting increased VHZ expression, amount or activity in a cell; and (b) reducing the level of VHZ in the cell.

As an 11th aspect of the invention, we provide a method of identifying a molecule capable of binding to a VHZ polypeptide, the method comprising contacting a VHZ polypeptide or a sequence having at least 90% sequence identity thereto with a candidate molecule and determining whether the candidate molecule binds to the VHZ polypeptide or sequence having at least 90% sequence identity thereto.

We provide, according to a 12th aspect of the invention, there is provided a method of identifying a modulator of VHZ, the method comprising contacting a cell with a candidate molecule and detecting elevated or reduced expression, amount or activity of VHZ in or of the cell.

According to a 13th aspect of the present invention, we provide a method of identifying a molecule suitable for the treatment, prophylaxis or alleviation of cancer, the method comprising determining if a candidate molecule is an agonist or antagonist of VHZ or a sequence having at least 90% sequence identity thereto. The method may comprise exposing a candidate molecule to a VHZ polypeptide or a cell expressing a VHZ polypeptide in order to determine if the candidate molecule is an agonist or antagonist thereof.

There is provided, according to a 14th aspect of the present invention, a method of identifying an agonist or antagonist of a VHZ or a sequence having at least 90% sequence identity thereto, the method comprising administering a candidate molecule to an animal and determining whether the animal exhibits increased or decreased expression, amount or activity of VHZ.

We provide, according to a 15th aspect of the present invention, a method of treatment, prophylaxis or alleviation of a cancer in an individual, the method comprising modulating the expression, amount or activity of a VHZ in a cell of an individual. The cancer may comprise breast cancer, such as invasive or metastatic cancer such as Invasive Ductal Carcinoma (IDC). The method may be such that the expression, amount or activity of VHZ is decreased in a breast cell of the individual.

We provide, according to a 16th aspect of the present invention, a method of diagnosis of a cancer or susceptibility to cancer in an individual or prognosis of an individual with cancer, the method comprising detecting modulation of expression, amount or activity of VHZ in a cell of the individual. The cancer may comprise breast cancer, such as invasive or metastatic cancer such as Invasive Ductal Carcinoma (IDC).

We provide, according to a 17th aspect of the present invention, a method of determining whether a tumour in an individual is, or is likely to be, an invasive or metastatic tumour, the method comprising detecting modulation of expression, amount or activity of VHZ in a tumour cell of the individual.

We provide, according to a 18th aspect of the present invention, a method of treatment, prophylaxis or alleviation of cancer in an individual, the method comprising detecting modulation of expression, amount or activity of VHZ in a cell of the individual and administering an appropriate therapy to the individual based on the aggressiveness of the tumour. The therapy may comprise an anti-VHZ agent as described above. The cancer may comprise breast cancer, such as invasive or metastatic cancer such as Invasive Ductal Carcinoma (IDC).

The diagnosis, prognosis or choice of therapy may be further determined by assessing the size of the tumour, or the lymph node stage, or both, optionally together or in combination with other risk factors. The diagnosis, prognosis or choice of therapy may be further determined by assessing the estrogen receptor (ER) status of the tumour.

We provide, according to a 19th aspect of the present invention, molecule, agonist or antagonist of a VHZ polypeptide identified by a method or use as set out above.

We provide, according to a 20th aspect of the present invention, a molecule capable of modulating, such as down-regulating, the expression of a VHZ for use in the treatment, prophylaxis or alleviation of cancer. The molecule may comprise an anti-peptide antibody generated against RRL-RPGSIETYEQEK (SEQ ID NO: 3) corresponding to amino acid residues (126-140) of human VHZ.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 1A. VHZ-EGFP (green) is transfected into NRK cells, and exhibits a range of subcellular locations (a). A predominant localization of VHZ is the centrosome, where it co-localizes with the centrosomal marker-pericentrin in red (b). To-pro-3 iodide is used to visualize nuclei in blue (b). Merged images showed that VHZ-EGFP (green) co-localized with pericentrin (c). Bar, 20 μm.

FIG. 1B. VHZ-EGFP is transfected into NRK cells and is visualized in cells at various cell cycle stages: Interphase (a), Prophase (b), Metaphase (c), and Telophase (d). Pericentrin is shown in red (a'-d'), and nuclei are shown with To-pro-3 iodide in blue (a'-d'). The images are merged as shown (a"-d"). Bar, 10 μm.

FIG. 2A. Endogenous VHZ is visualized in NRK (a-c, bar, 10 μm) and MCF-10A (d-f, bar, 20 μm) cells by double staining with affinity-purified rabbit anti-VHZ and mouse anti-γ-tubulin antibodies followed by anti-rabbit IgG conjugated with anti-rabbit-FITC (green) and anti-mouse IgG conjugated with anti-mouse-Texas Red. Endogenous VHZ is also detected in A431 cells (g-i, bar, 20 μm) by double staining with mouse monoclonal antibody anti-VHZ (clone #25) and rabbit anti-pericentrin antibodies followed by anti-mouse IgG conjugated with anti-mouse-FITC (green) and anti-rabbit IgG conjugated with anti-rabbit-Texas Red.

FIG. 2B. Endogenous VHZ is visualized in serum-starved NRK (a-c, bar, 20 μm) by double staining with rabbit anti-VHZ and mouse anti-γ-tubulin antibodies followed by anti-rabbit IgG conjugated with anti-rabbit-FITC (green) and anti-mouse IgG conjugated with anti-mouse-Texas Red.

FIG. 3B. a. Three total cell lysates are derived from MCF-7 cells expressing VHZ-EGFP, VHZ(C95S)-EGFP, or EGFP vector. The protein expression levels are analyzed by western blot with anti-EGFP antibody. GAPDH is used as protein loading control. b. DNA content is measured by BrdU incorporation and FACS analysis. APC-BrdU incorporation to the newly synthesized DNA (R1 corresponds to the amount of red fluorescence).

FIG. 3C. NRK cells that stably expressed the same three expression constructs showed that VHZ could reduce G1 but increase S populations. The resulting histogram consists of three populations (in %): M1:G1 phase, M2: S phase and M3: G2/M phase. The graph showed typical results obtained for a proliferating cell population when the DNA content of its individual cells is determined by FACS analysis.

FIG. 4B. A proposed model is shown to illustrate how the VHZ might coordinate with these molecules in G1/S phase transition.

FIG. 5A. VHZ is seen to localize to the centrosome of cells in breast cancer by indirect double immunofluorescence labeling on the same tissue section. VHZ (a) and γ-tubulin (b) are co-localized at the centrosome (c) as indicated by the white arrowheads. Image c shows the merged images a and b. Bar: 100 μm.

FIG. 5B. Two consecutive sections of breast cancer samples are processed for immunohistochemical labeling to detect VHZ and γ-tubulin, respectively. The positive signals are detected by staining with 3,3'-diaminobenzidine chromogen (brown). Similar centrosomal labeling patterns of VHZ (a) and γ-tubulin localization (b) are indicated by the black arrows. Overview images (a', b') are derived from two adjacent sections. Three rectangular areas boxed in panels a' to c' (magnification ×630) are further enlarged (×5) and shown in panels a to c, respectively where centrosomes are indicated by black arrows. Panel c' and c show a VHZ-negative sample as a control. An original overview image is shown in (FIG. 8A).

FIG. 5C. VHZ protein is overexpressed throughout the cytoplasm of dispersed epithelia in some breast cancer samples. An original overview image is shown in (FIG. 8B). Selected sections from different breast samples are shown in overview images (a' and b'). Three rectangular areas boxed in the overview images (a', b' and c' magnification ×400) are further enlarged (×5) and shown in panels a, b and c, respectively. Panel c and c' is a VHZ-negative sample shown as a control.

FIG. 6A. Two adjacent formalin-fixed and paraffin-embedded breast cancer samples tissue sections showed VHZ positive cells that are E-cadherin negative (a, magnification ×400) and VHZ negative epithelia are E-cadherin positive (b, magnification ×400).

FIG. 6B. To assess MCF-7-VHZ-EGFP and MCF-7-VHZ (C95S)-EGFP cell motility, cells are plated in a confluent monolayer on a coverslip. The cell-coated coverslip is then inverted with cell side down onto a fresh culture dish. Images are taken at 0-hour and 48-hour for MCF-7-VHZ-EGFP cells (a, a') and for MCF-7-VHZ (C95S)-EGFP (b, b'). Panel a' showed MCF-7-VHZ-EGFP cells moving out (arrows indicated) from underneath the overlaid coverslip. Immunofluorescent images (a, b). Phase-contrast images (a', b' magnification ×200).

FIG. 7A and FIG. 7B are figures showing that VHZ mRNA is broadly expressed in tissues and cells Human Multiple Tissue Arrays (Cat#7776-1) are obtained from BD Bioscience (San Jose, Calif.). The arrays contain 73 mRNAs derived from 65 different human tissues and 8 human cell lines.

FIG. 7A. The dot blots are probed with human VHZ cDNA that is radiolabeled with $^{32}$P-dCTP according to the manufacturer's instructions (Cat#1585584, Roche, Mannheim, Germany). VHZ mRNA expression patterns are shown. VHZ is predominantly expressed in the heart (spots: 4A, 4C-4H) and in many other tissues, as well as in the lung carcinoma cell line-A549 (spot-10H).

FIG. 7B. A complete map of Human Multiple Tissue Arrays.

FIG. 8B. Overexpression of VHZ protein is found in the cytoplasm of breast cancer cells (magnification ×200).

FIG. 9B. The VHZ mAbs can be used for ECL (A), IF (B) and IHC (FIG. 5).

DETAILED DESCRIPTION

Figure 1A:
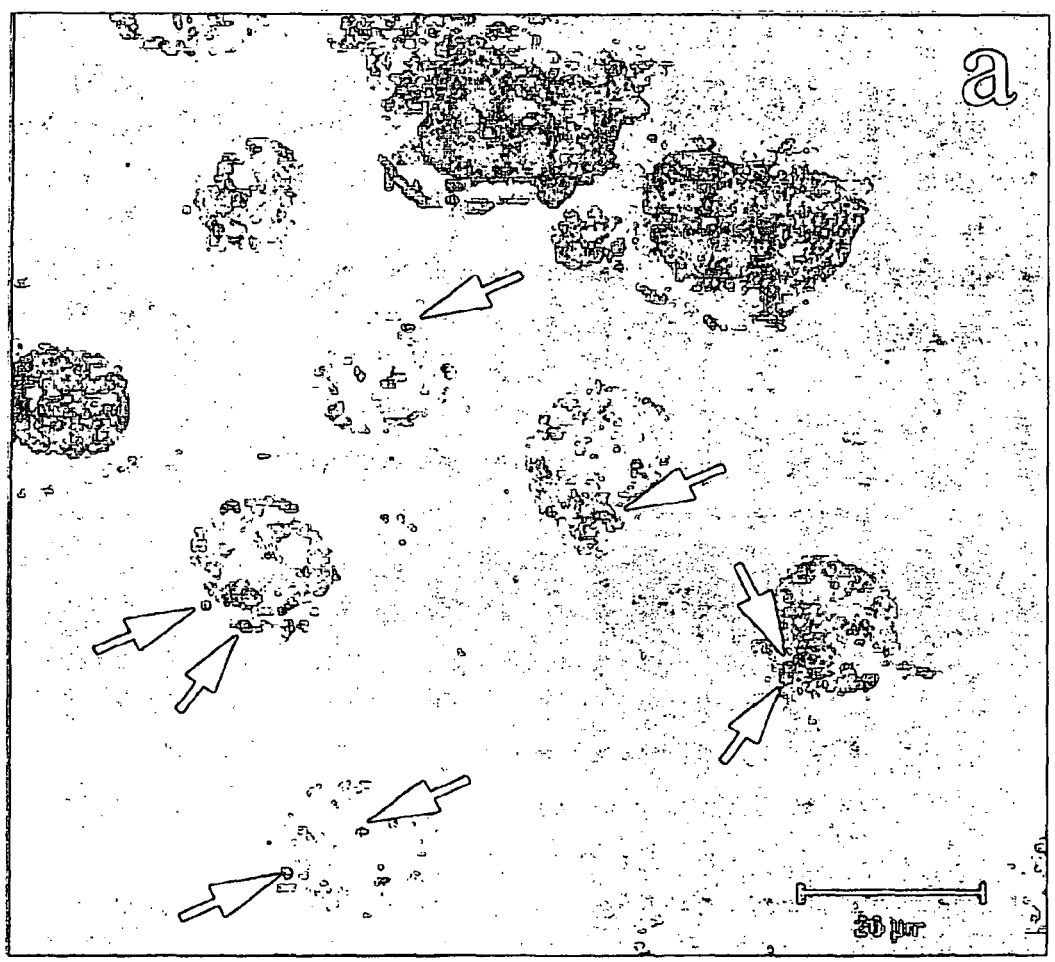
FIG. 1A and FIG. 1B are figures showing that exogenous VHZ localizes in the centrosome and throughout the cytoplasm. Indirect immunofluorescence showed exogenous VHZ in the centrosome.
Figure 1A:
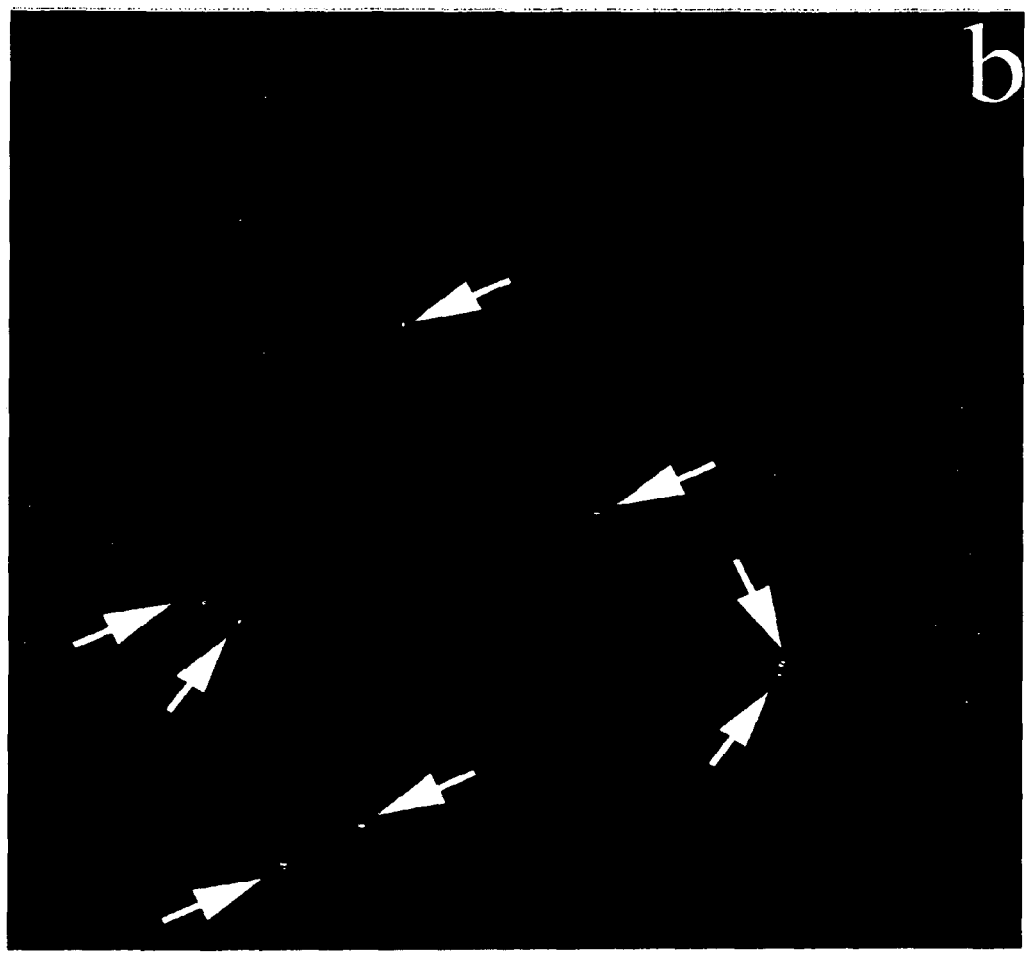
Figure 1A:
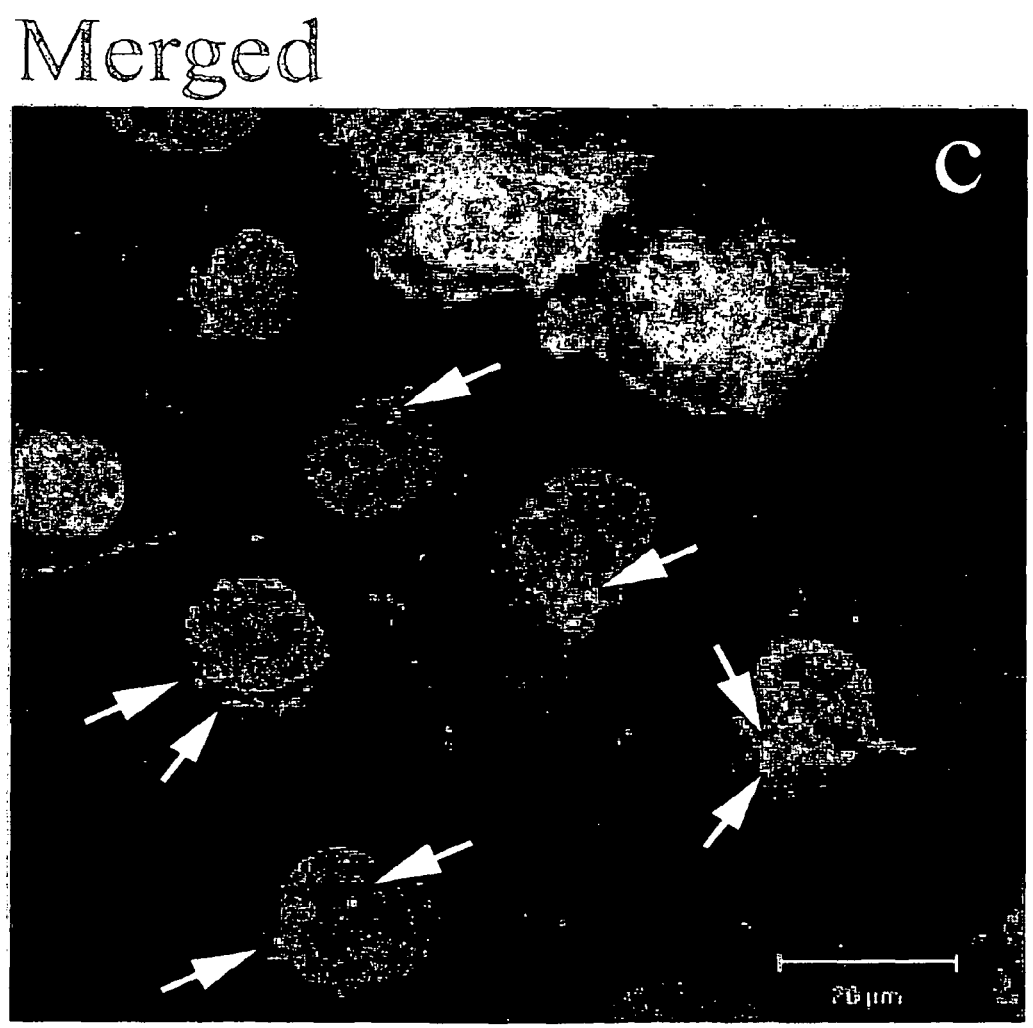

The present invention is based on the demonstration, for the first time, that VHZ phosphatase plays a role in cancer.

VHZ is the smallest known active protein-tyrosine phosphatase (only 16 kDa) and belongs to the group of small Vaccinia virus VH1-related dual specific phosphatases. The gene encoding VHZ is located on human chromosome 1q23.1 and consists of only two coding exons (Wu et al., 2004, Int J Biochem Cell Biol. 36(8):1542-53.

VHZ shows distinctive phosphatase activity toward p-nitrophenyl phosphate, as well as oligopeptides containing phospho-tyrosine and phospho-threonine residues. Furthermore, VHZ can dephosphorylate p44ERK1 but not p38 and p54SAPKbeta in vitro (Alonso et al (2004). J Biol. Chem. 20; 279(34):35768-74).

We show that VHZ is predominantly associated with invasive human epithelial breast cancer cells. Overexpression of VHZ protein is found in the centrosome (6/65 cases) or throughout the cytoplasm (11/65 cases) of human breast cancer samples examined.

Accordingly, VHZ may be used as a marker for detection of breast cancer. The level of VHZ expression may be used as an indicator of cancer, in particular breast cancer such as metastatic, aggressive or invasive breast cancer. The level of VHZ expression may also be used as an indicator of likelihood of such a cancer. We therefore provide for methods of diagnosis or detection of a cancer, particularly breast cancer. We further provide methods of diagnosis and detection of the aggressiveness or invasiveness or the metastatic state, or any combination of these, of such a cancer. The methods may comprise analysis of protein levels (e.g., immunohistochemistry) or RNA levels (e.g., by in situ hybridisation). Such diagnostic and detection methods are described in further detail below.

Using indirect immunofluorescence, we show that both exogenous and endogenous VHZ proteins are localized in the centrosome in addition to its cytoplasmic distribution. Accordingly, VHZ may be used as a marker for detection of centrosomal structures.

We demonstrate that VHZ regulates cell-cycle progression and that it has the capacity to enhance the G1-S phase transition. We demonstrate that over-expression of VHZ contributes to breast cancer development. FACS analysis of BrdU-labeled MCF-7 cells engineered to express VHZ indicates that VHZ is able to accelerate the G1 to S phase transition. Analogous results from FACS analyses of NRK cells that stably express the same three expression constructs shows that VHZ accelerates G1 to S phase transition by reducing G1 but increasing S populations.

Accordingly, we provide for methods of treatment or prophylaxis of an individual suffering from cancer. Restoration of VHZ levels to those in normal tissue may also be used as a means of restoring normal function of breast cells. We therefore provide for the use of VHZ nucleic acids and polypeptides for the treatment of cancers, including breast cancer. Our methods may be used for treatment or prophylaxis of breast cancer or invasive cancer such as invasive breast cancer.

We further provide for the user of VHZ in screening for drugs against cancer, for example breast cancer. The cancer may comprise invasive breast cancer. Cells over- and underexpressing VHZ, as well as tissues, organs and organisms comprising these may be used as models for cancer or in screens for anti-cancer agents.

Overexpression of VHZ in MCF-7 cells causes down-regulation of p21Cip1 and upregulation of Cdk4. As a result, an accumulation of phosphorylated (inactivated) retinoblastoma protein (Rb) is observed as assessed by immunoblotting with phospho-specific antibodies. Cells expressing catalytically inactive VHZ (C95S) are impaired in the above VHZ-mediated events, indicating that these properties require phosphatase activity.

Mutation of the catalytic cysteine residue (C95S) in VHZ abolishes its protein tyrosine phosphatase (PTP) activity.

Where the term "VHZ" is used, this should be taken to refer to any VHZ sequence, including a VHZ protein or a VHZ nucleic acid and any fragment, variant homologue, derivative, variant thereof.

The properties and activities of VHZ are described in this document, for example, in the references.

VHZ Polypeptides

The methods and compositions described here make use of VHZ polypeptides, which are described in detail below.

VHZ is also known as DUSP23, MOSP, LDP-3, DUSP25, FLJ20442 and RP11-190A12.1

As used here, the term "VHZ polypeptide" is intended to refer to a sequence having GenBank Accession number NP_060293.2, NP_081001.1, XP_341157.1, XP_001170819.1, XP_001170835.1, XP_545747.2, NP_001076078.1, NP_001011371.1, NP_783859.1, NP_001034709.1, XP_001480730.1, XP_001117253.1 or XP_001117256.1.

A "VHZ polypeptide" may comprise or consist of a human VHZ polypeptide, such as the sequence having accession number NP_060293.

Homologues variants and derivatives thereof of any, some or all of these polypeptides are also included.

VHZ polypeptides may be used for a variety of means, for example, administration to an individual suffering from, or suspected to be suffering from, breast cancer, for the treatment thereof. They may also be used for production or screening of anti-VHZ agents such as specific VHZ binding agents, in particular, anti-VHZ antibodies. These are described in further detail below. The expression of VHZ polypeptides may be detected for diagnosis or detection of cancer, in particular breast cancer.

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., *Posttranslational Protein Modifications: Perspectives and Prospects,* pgs. 1-12 in *Posttranslational Covalent Modification of Proteins,* B. C. Johnson, Ed., Academic Press, New York, 1983; Seifter et al., "Analysis for protein modifications and non-protein cofactors", *Meth Enzymol* (1990) 182:626-646 and Rattan et al., "Protein Synthesis: Posttranslational Modifications and Aging", *Ann NY Acad Sci* (1992) 663:48-62.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralising antibodies in vivo.

As applied to VHZ, the resultant amino acid sequence may have one or more activities, such as biological activities in common with a VHZ polypeptide, for example a human VHZ polypeptide. For example, a VHZ homologue may have an increased expression level in breast cancer cells compared to normal breast cells. In particular, the term "homologue" covers identity with respect to structure and/or function providing the resultant amino acid sequence has VHZ activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the VHZ nucleic acid sequence.

Where reference is made to the "activity" or "biological activity" of a polypeptide such as VHZ, these terms are intended to refer to the metabolic or physiological function of VHZ, including similar activities or improved activities or these activities with decreased undesirable side effects. Also included are antigenic and immunogenic activities of VHZ. Examples of such activities, and methods of assaying and quantifying these activities, are known in the art, and are described in detail elsewhere in this document.

For example, such activities may include any one or more of the following: hydrolase activity, protein tyrosine phosphatase activity, protein tyrosine/serine/threonine phosphatase activity and protein amino acid dephosphorylation. Assays for these activities are known in the art, and are for example described in Wu et al (2004), *Int J Biochem Cell Biol.* 36(8):1542-53 and Alonso et al (2004). *J Biol. Chem.* 20; 279(34):35768-74.

Other VHZ Polypeptides

VHZ variants, homologues, derivatives and fragments are also of use in the methods and compositions described here.

The terms "variant", "homologue", "derivative" or "fragment" in relation to VHZ include any substitution of, variation of, modification of, replacement of, deletion of or addition of one (or more) amino acid from or to a sequence. Unless the context admits otherwise, references to "VHZ" includes references to such variants, homologues, derivatives and fragments of VHZ.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

VHZ polypeptides as described here may also have deletions, insertions or substitutions of amino acid residues which produce a silent change and result in a functionally equivalent amino acid sequence. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and in the same line in the third column may be substituted for each other:

| ALIPHATIC | Non-polar | G A P |
|---|---|---|
|  |  | I L V |
|  | Polar - uncharged | C S T M |
|  |  | N Q |
|  | Polar - charged | D E |
|  |  | K R |
| AROMATIC |  | H F W Y |

VHZ polypeptides may further comprise heterologous amino acid sequences, typically at the N-terminus or C-terminus, such as the N-terminus. Heterologous sequences may include sequences that affect intra or extracellular protein targeting (such as leader sequences). Heterologous sequences may also include sequences that increase the immunogenicity of the VHZ polypeptide and/or which facilitate identification, extraction and/or purification of the polypeptides. Another heterologous sequence that may be used is a polyamino acid sequence such as polyhistidine which may be N-terminal. A polyhistidine sequence of at least 10 amino acids (SEQ ID NO: 4), such as at least 17 amino acids but fewer than 50 amino acids may be employed.

The VHZ polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

VHZ polypeptides as described here are advantageously made by recombinant means, using known techniques. However they may also be made by synthetic means using techniques well known to skilled persons such as solid phase synthesis. Such polypeptides may also be produced as fusion proteins, for example to aid in extraction and purification. Examples of fusion protein partners include glutathione-S-transferase (GST), 6×His (SEQ ID NO: 5), GAL4 (DNA binding and/or transcriptional activation domains) and β-galactosidase. It may also be convenient to include a proteolytic cleavage site between the fusion protein partner and the protein sequence of interest to allow removal of fusion protein sequences, such as a thrombin cleavage site. The fusion protein may be one which does not hinder the function of the protein of interest sequence.

The VHZ polypeptides may be in a substantially isolated form. This term is intended to refer to alteration by the hand of man from the natural state. If an "isolated" composition or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the VHZ protein may be mixed with carriers or diluents which will not interfere with the intended purpose of the protein and still be regarded as substantially isolated. A VHZ polypeptide may also be in a substantially purified form, in which case it will generally comprise the protein in a preparation in which more than 90%, for example, 95%, 98% or 99% of the protein in the preparation is a VHZ polypeptide.

By aligning VHZ sequences from different species, it is possible to determine which regions of the amino acid sequence are conserved between different species ("homologous regions"), and which regions vary between the different species ("heterologous regions").

The VHZ polypeptides may therefore comprise a sequence which corresponds to at least part of a homologous region. A homologous region shows a high degree of homology between at least two species. For example, the homologous region may show at least 70%, at least 80%, at least 90% or at least 95% identity at the amino acid level using the tests described above. Peptides which comprise a sequence which corresponds to a homologous region may be used in therapeutic strategies as explained in further detail below. Alternatively, the VHZ peptide may comprise a sequence which corresponds to at least part of a heterologous region. A heterologous region shows a low degree of homology between at least two species.

VHZ Homologues

The VHZ polypeptides disclosed for use include homologous sequences obtained from any source, for example related viral/bacterial proteins, cellular homologues and synthetic peptides, as well as variants or derivatives thereof. Thus polypeptides also include those encoding homologues of VHZ from other species including animals such as mammals (e.g. mice, rats or rabbits), especially primates, more especially humans. More specifically, homologues include human homologues.

In the context of this document, a homologous sequence is taken to include an amino acid sequence which is at least 15, 20, 25, 30, 40, 50, 60, 70, 80 or 90% identical, such as at least 95 or 98% identical at the amino acid level, for example over at least 50 or 100, 110, 115, 120, 125, 130, 135, 140, 141, 142, 143, 144, 145, 146, 147, 148 or 149 amino acids with the sequence of a relevant VHZ sequence.

In particular, homology should typically be considered with respect to those regions of the sequence known to be essential for protein function rather than non-essential neighbouring sequences. This is especially important when considering homologous sequences from distantly related organisms. An example is the cysteine residue at or corresponding to residue number 95 of the human VHZ protein, shown to be essential for phosphatase function, and surrounding residues.

Although homology can also be considered in terms of similarity (i.e. amino acid residues having similar chemical properties/functions), in the context of the present document homology may be expressed in terms of sequence identity.

Homology comparisons can be conducted by eye, or more usually, with the aid of readily available sequence comparison programs. These publicly and commercially available computer programs can calculate % identity between two or more sequences.

% identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local identity or similarity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Altschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package may be used, or in the case of other software, the default matrix, such as BLOSUM62.

Once the software has produced an optimal alignment, it is possible to calculate % homology, such as % sequence identity. The software typically does this as part of the sequence comparison and generates a numerical result.

The terms "variant" or "derivative" in relation to amino acid sequences includes any substitution of, variation of, modification of, replacement of, deletion of or addition of one (or more) amino acids from or to the sequence providing the resultant amino acid sequence retains substantially the same activity as the unmodified sequence, such as having at least the same activity as the VHZ polypeptides.

Polypeptides having the VHZ amino acid sequence disclosed here, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Amino acid substitutions may include the use of non-naturally occurring analogues, for example to increase blood plasma half-life of a therapeutically administered polypeptide.

VHZ Fragments

Polypeptides for use in the methods and compositions described here also include fragments of the full length sequence of any of the VHZ polypeptides identified above. Fragments may comprise at least one epitope. Methods of identifying epitopes are well known in the art. Fragments will typically comprise at least 6 amino acids, such as at least 10, 20, 30, 50 or 100 amino acids.

Included are fragments comprising or consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or more residues from a relevant VHZ amino acid sequence.

We further describe peptides comprising a portion of a VHZ polypeptide as described here. Thus, fragments of VHZ and its homologues, variants or derivatives are included. The peptides may be between 2 and 200 amino acids, such as between 4 and 40 amino acids in length. The peptide may be derived from a VHZ polypeptide as disclosed here, for example by digestion with a suitable enzyme, such as trypsin. Alternatively the peptide, fragment, etc may be made by recombinant means, or synthesised synthetically.

Such VHZ fragments may be used to generate probes to preferentially detect VHZ expression, for example, through antibodies generated against such fragments. These antibodies would be expected to bind specifically to VHZ, and are useful in the methods of diagnosis and treatment disclosed here.

VHZ and its fragments, homologues, variants and derivatives, may be made by recombinant means. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 5), GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be one which will not hinder the function of the protein of interest sequence. Proteins may also be obtained by purification of cell extracts from animal cells.

The VHZ polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A VHZ variant, homologue, fragment or derivative may also be in a substantially purified form, in which case it will generally comprise the protein in a preparation in which more than 90%, e.g. 95%, 98% or 99% of the protein in the preparation is a protein.

The VHZ polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A VHZ polypeptides, variants, homologues, fragments and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The VHZ polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the VHZ polypeptides, variants, homologues, fragments and derivatives disclosed here are expressed may be used in assay systems to identify candidate substances which interfere with or enhance the functions of the polypeptides in the cell.

VHZ Nucleic Acids

The methods and compositions described here may employ, as a means for detecting expression levels of VHZ, VHZ polynucleotides, VHZ nucleotides and VHZ nucleic acids, as well as variants, homologues, derivatives and fragments of any of these. In addition, we disclose particular VHZ fragments useful for the methods of diagnosis described here. The VHZ nucleic acids may also be used for the methods of treatment or prophylaxis described.

The terms "VHZ polynucleotide", "VHZ nucleotide" and "VHZ nucleic acid" may be used interchangeably, and should be understood to specifically include both cDNA and genomic VHZ sequences. These terms are also intended to include a nucleic acid sequence capable of encoding a VHZ polypeptide and/or a fragment, derivative, homologue or variant of this.

Where reference is made to a VHZ nucleic acid, this should be taken as a reference to any member of the VHZ family of nucleic acids. Of particular interest are VHZ nucleic acids selected from the group consisting of: NM_017823.3, NM_026725.2, XM_341156.3, XM_001170819.1, XM_001170835.1, XM_545747.2, NM_001082609.1, NM_001011371.1, NM_175732.1, NM_001039620.1, XM_001480680.1, XM_001117253.1 or XM_001117256.1.

Also included are any one or more of the nucleic acid sequences set out as "Other VHZ nucleic acid sequences" below.

For example, the VHZ nucleic acid may comprise a human VHZ sequence having GenBank Accession Number NM_017823.3.

VHZ nucleic acids may be used for a variety of means, for example, administration to an individual suffering from, or suspected to be suffering from, breast cancer, for the treatment thereof. The expression of VHZ nucleic acids may be detected for diagnosis or detection of cancer, in particular breast cancer. VHZ nucleic acids may also be used for the expression or production of VHZ polypeptides.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

The term "nucleotide sequence" may means DNA.

Other Nucleic Acids

We also provide nucleic acids which are fragments, homologues, variants or derivatives of VHZ nucleic acids. The terms "variant", "homologue", "derivative" or "fragment" in relation to VHZ nucleic acid include any substitution of, variation of, modification of, replacement of, deletion of or addition of one (or more) nucleic acids from or to the sequence of a VHZ nucleotide sequence. Unless the context admits otherwise, references to "VHZ" and "VHZ" include references to such variants, homologues, derivatives and fragments of VHZ.

The resultant nucleotide sequence may encode a polypeptide having any one or more VHZ activity. The term "homologue" may be intended to cover identity with respect to structure and/or function such that the resultant nucleotide sequence encodes a polypeptide which has VHZ activity. For example, a homologue etc of VHZ may have a increased expression level in breast cancer cells compared to normal breast cells. With respect to sequence identity (i.e. similarity), there may be at least 70%, at least 75%, at least 85% or at least 90% sequence identity. There may be at least 95%, such as at least 98%, sequence identity to a relevant sequence (e.g., a VHZ sequence having GenBank accession number NM_017823.3). These terms also encompass allelic variations of the sequences.

Variants, Derivatives and Homologues

VHZ nucleic acid variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleic acid from or to the sequence. Said variant, homologues or derivatives may code for a polypeptide having biological activity. Such fragments, homologues, variants and derivatives of VHZ may comprise modulated activity, as set out above.

As indicated above, with respect to sequence identity, a "homologue" may have at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence (e.g., a VHZ sequence having GenBank accession number NM_017823.3).

There may be at least 95% identity, at least 96% identity, at least 97% identity, at least 98% identity or at least 99% identity. Nucleotide identity comparisons may be conducted as described above. A sequence comparison program which may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences may be at least 15 nucleotides in length, such as at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, may be at least 40% homologous, at least 45% homologous, at least 50% homologous, at least 55% homologous, at least 60% homologous, at least 65% homologous, at least 70% homologous, at least 75% homologous, at least 80% homologous, at least 85% homologous, at least 90% homologous, or at least 95% homologous to the corresponding nucleotide sequences presented herein (e.g., a VHZ sequence having GenBank accession number NM_017823.3). Such polynucleotides may be generally at least 70%, at least 80 or 90% or at least 95% or 98% homologous to the corresponding nucleotide sequences over a region of at least 20, such as at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$ or $^{33}P$ or with non-radioactive probes (e.g., fluorescent dyes, biotin or digoxigenin).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

We provide nucleotide sequences that may be able to hybridise to the VHZ nucleic acids, fragments, variants, homologues or derivatives under stringent conditions (e.g. 65° C. and 0.1×SSC (1×SSC=0.15 M NaCl, 0.015 M $Na_3$Citrate pH 7.0)).

Generation of Homologues, Variants and Derivatives

Polynucleotides which are not 100% identical to the relevant sequences (e.g., a human VHZ sequence having GenBank accession number NM_017823.3) but which are also included, as well as homologues, variants and derivatives of VHZ can be obtained in a number of ways. Other variants of the sequences may be obtained for example by probing DNA libraries made from a range of individuals, for example individuals from different populations. For example, VHZ homologues may be identified from other individuals, or other species. Further recombinant VHZ nucleic acids and polypeptides may be produced by identifying corresponding positions in the homologues, and synthesising or producing the molecule as described elsewhere in this document.

In addition, other viral/bacterial, or cellular homologues of VHZ, particularly cellular homologues found in mammalian cells (e.g. rat, mouse, bovine and primate cells), may be obtained and such homologues and fragments thereof in general will be capable of selectively hybridising to human VHZ. Such homologues may be used to design non-human VHZ nucleic acids, fragments, variants and homologues. Mutagenesis may be carried out by means known in the art to produce further variety.

Sequences of VHZ homologues may be obtained by probing cDNA libraries made from or genomic DNA libraries from other animal species, and probing such libraries with probes comprising all or part of any of the VHZ nucleic acids, fragments, variants and homologues, or other fragments of VHZ under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the VHZ nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the VHZ sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, VHZ nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, such as at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Primers comprising fragments of VHZ are particularly useful in the methods of detection of VHZ expression, such as up-regulation of VHZ expression, for example, as associated with breast cancer. Suitable primers for amplification of VHZ may be generated from any suitable stretch of VHZ. Primers which may be used include those capable of amplifying a sequence of VHZ which is specific.

Although VHZ primers may be provided on their own, they are most usefully provided as primer pairs, comprising a forward primer and a reverse primer.

Longer polynucleotides will generally be produced using recombinant means, for example using a PCR (polymerase chain reaction) cloning techniques. This will involve making a pair of primers (e.g. of about 15 to 30 nucleotides), bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}P$ or $^{35}S$, digoxigenin, fluorescent dyes, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the VHZ nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

VHZ Control Regions

For some purposes, it may be necessary to utilise or investigate control regions of VHZ. Such control regions include promoters, enhancers and locus control regions. By a control region we mean a nucleic acid sequence or structure which is capable of modulating the expression of a coding sequence which is operatively linked to it.

For example, control regions are useful in generating transgenic animals expressing VHZ. Furthermore, control regions may be used to generate expression constructs for VHZ. This is described in further detail below.

Identification of control regions of VHZ is straightforward, and may be carried out in a number of ways. For example, the coding sequence of VHZ may be obtained from an organism, by screening a cDNA library using a human or mouse VHZ cDNA sequence as a probe. 5' sequences may be obtained by screening an appropriate genomic library, or by primer extension as known in the art. Database searching of genome databases may also be employed. Such 5' sequences which are particularly of interest include non-coding regions. The 5' regions may be examined by eye, or with the aid of computer programs, to identify sequence motifs which indicate the presence of promoter and/or enhancer regions.

Furthermore, sequence alignments may be conducted of VHZ nucleic acid sequences from two or more organisms. By aligning VHZ sequences from different species, it is possible to determine which regions of the amino acid sequence are conserved between different species. Such conserved regions are likely to contain control regions for the gene in question (i.e., VHZ). The mouse and human genomic sequences as disclosed here, for example, a mouse VHZ genomic sequence, may be employed for this purpose. Furthermore, VHZ homologues from other organisms may be obtained using standard methods of screening using appropriate probes generated from the mouse and human VHZ sequences. The genome of the pufferfish (*Takifugu rubripes*) or zebrafish may also be screened to identify a VHZ homologue; thus, several zebrafish sequences of VHZ have been identified (noted above). Comparison of the 5' non-coding region of the Fugu or zebrafish VHZ gene with a mouse or human genomic VHZ sequence may be used to identify conserved regions containing control regions.

Deletion studies may also be conducted to identify promoter and/or enhancer regions for VHZ.

The identity of putative control regions may be confirmed by molecular biology experiments, in which the candidate sequences are linked to a reporter gene and the expression of the reporter detected.

Detection and Diagnostic Methods

Detection of Expression of VHZ

We show in the Examples that the expression of VHZ in breast cancer tissue is up-regulated when compared to normal breast tissue. Accordingly, we provide for a method of diagnosis of cancer, including breast cancer such as metastatic, aggressive or invasive breast cancer, comprising detecting modulation of expression of VHZ, such as up-regulation of expression of VHZ in a cell or tissue of an individual.

Detection of VHZ expression, activity or amount may be used to provide a method of determining the proliferative state of a cell. Thus, a proliferative cell is one with high levels of VHZ expression, activity or amount compared to a normal cell. Similarly, a non-proliferative cell may be one with low levels VHZ expression, activity or amount compared to a normal cell.

Such detection may also be used to determine whether a cell will become invasive or aggressive. Thus, detection of a high level of VHZ expression, amount or activity of VHZ in the cell may indicate that the cell is likely to be or become aggressive, metastatic or invasive. Similarly, if a cell has a low level of VHZ expression, amount or activity, the cell is not or is not likely to be aggressive, metastatic or invasive.

It will be appreciated that if the level of VHZ varies with the aggressiveness of a tumour, that detection of VHZ expression, amount or activity may also be used to predict a survival rate of an individual with cancer, i.e., high levels of VHZ indicating a lower survival rate or probability and low levels of VHZ indicating a higher survival rate or probability, both as compared to individuals or cognate populations with normal levels of VHZ. Detection of expression, amount or activity of VHZ may therefore be used as a method of prognosis of an individual with cancer.

Detection of VHZ expression, amount or level may be used to determine the likelihood of success of a particular therapy in an individual with a cancer. It may be used in a method of determining whether a tumour in an individual is, or is likely to be, an invasive or metastatic tumour.

The diagnostic methods described in this document may be combined with the therapeutic methods described. Thus, we provide for a method of treatment, prophylaxis or alleviation of cancer in an individual, the method comprising detecting modulation of expression, amount or activity of VHZ in a cell of the individual and administering an appropriate therapy to the individual based on the aggressiveness of the tumour. The therapy may comprise an anti-VHZ agent as described above.

Typically, physical examination of the breast and X-ray mammography is used for the detection of breast cancer. A biopsy of the tumour is typically taken for histopathological examination for the diagnosis of breast cancer. Detection of VHZ expression, amount or activity can be used to diagnose, or further confirm the diagnosis of, breast cancer, along with the standard histopathological procedures. This may be especially useful when the histopathological analysis does not yield a clear result.

The presence and quantity of VHZ polypeptides and nucleic acids may be detected in a sample as described in further detail below. Thus, the VHZ associated diseases, including breast cancer, can be diagnosed by methods comprising determining from a sample derived from a subject an abnormally decreased or increased expression, amount or activity, such as a increased expression, amount or activity, of the VHZ polypeptide or VHZ mRNA.

The sample may comprise a cell or tissue sample from an organism or individual suffering or suspected to be suffering from a disease associated with increased, reduced or otherwise abnormal VHZ expression, amount or activity, including spatial or temporal changes in level or pattern of expression, amount or activity. The level or pattern of expression, amount or activity of VHZ in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from breast cancer, such as a breast tissue or cell sample.

In some embodiments, an increased level of expression, amount or activity of VHZ is detected in the sample. The level of VHZ may be increased to a significant extent when compared to normal cells, or cells known not to be cancerous. Such cells may be obtained from the individual being tested, or another individual, such as those matched to the tested individual by age, weight, lifestyle, etc.

In some embodiments, the level of expression, amount or activity of VHZ is increased by 10%, 20%, 30% or 40% or more. In some embodiments, the level of expression, amount or activity of VHZ is increased by 45% or more, such as 50% or more, as judged by cDNA hybridisation.

The expression, amount or activity of VHZ may be detected in a number of ways, as known in the art, and as described in further detail below. Typically, the amount of VHZ in a sample of tissue from an individual is measured, and compared with a sample from an unaffected individual. Both VHZ nucleic acid, as well as VHZ polypeptide levels may be measured.

Detection of the amount, activity or expression of VHZ may be used to grade breast cancer. For example, a high level of amount, activity or expression of VHZ may indicate an aggressive, invasive or metastatic cancer. Similarly, a low level of amount, activity or expression of VHZ may indicate a non-aggressive, non-invasive or non-metastatic cancer. Such a grading system may be used in conjunction with established grading systems such as the Elston-Ellis modified Scarff, Bloom, Richardson grading system, also known as the Nottingham grading system (NGS) (5, 6, Haybittle et al, 1982).

This system is the most studied and widely used method of breast tumor grading. The NGS is based on a phenotypic scoring procedure that involves the microscopic evaluation of morphologic and cytologic features of tumor cells including degree of tubule formation, nuclear pleomorphism and mitotic count (6). The sum of these scores stratifies breast tumors into grade I (G1) (well-differentiated, slow-growing), grade II (G2) (moderately differentiated), and grade III (G3) (poorly-differentiated, highly-proliferative) malignancies.

Levels of VHZ gene expression may be determined using a number of different techniques.

Measuring Expression of VHZ at the RNA Level

VHZ Gene Expression can be Detected at the RNA Level.

In one embodiment therefore, we disclose a method of detecting the presence of a nucleic acid comprising a VHZ nucleic acid in a sample, by contacting the sample with at least one nucleic acid probe which is specific for the VHZ nucleic acid and monitoring said sample for the presence of the VHZ nucleic acid. For example, the nucleic acid probe may specifically bind to the VHZ nucleic acid, or a portion of it, and binding between the two detected; the presence of the complex itself may also be detected.

Thus, in one embodiment, the amount of VHZ nucleic acid in the form of VHZ mRNA may be measured in a sample. VHZ mRNA may be assayed by in situ hybridization, Northern blotting and reverse transcriptase—polymerase chain reaction. Nucleic acid sequences may be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

VHZ RNA may be extracted from cells using RNA extraction techniques including, for example, using acid phenol/guanidine isothiocyanate extraction (RNAzol B; Biogenesis), or RNeasy RNA preparation kits (Qiagen). Typical assay formats utilising ribonucleic acid hybridisation include nuclear run-on assays, RT-PCR and RNase protection assays (Melton et al., *Nuc. Acids Res.* 12:7035. Methods for detection which can be employed include radioactive labels, enzyme labels, chemiluminescent labels, fluorescent labels and other suitable labels.

Each of these methods allows quantitative determinations to be made, and are well known in the art. Decreased or increased VHZ expression, amount or activity can therefore be measured at the RNA level using any of the methods well known in the art for the quantitation of polynucleotides. Any suitable probe from a VHZ sequence, for example, any portion of a suitable human VHZ sequence may be used as a probe. Sequences for designing VHZ probes may include a sequence having accession number NM_015472, or a portion thereof.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U. et al., *Science* 242:229-237 (1988) and Lewis, R., *Genetic Engineering News* 10:1, 54-55 (1990).

For example, the polymerase chain reaction may be employed to detect VHZ mRNA.

The "polymerase chain reaction" or "PCR" is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the Qβ Replicase technique, RNA replicase for the bacteriophage Qβ, which replicates single-stranded RNA, is used to amplify the target DNA, as described by Lizardi et al., 1988, *Bio/Technology* 6:1197.

A PCR procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Reverse transcription-polymerase chain reaction (RT-PCR) may be employed. Quantitative RT-PCR may also be used. Such PCR techniques are well known in the art, and may employ any suitable primer from a VHZ sequence.

Alternative amplification technology can also be exploited. For example, rolling circle amplification (Lizardi et al., 1998, *Nat Genet.* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Measuring Expression of VHZ at the Polypeptide Level

VHZ Expression can be Detected at the Polypeptide Level.

In a further embodiment, therefore, VHZ expression, amount or activity may be detected by detecting the presence or amount of VHZ polypeptide in a sample. This may be achieved by using molecules which bind to VHZ polypeptide. Suitable molecules/agents which bind either directly or indirectly to the VHZ polypeptide in order to detect its presence include naturally occurring molecules such as peptides and proteins, for example antibodies, or they may be synthetic molecules.

Thus, we disclose a method of detecting the presence of a VHZ polypeptide by contacting a cell sample with an antibody capable of binding the polypeptide and monitoring said sample for the presence of the polypeptide.

For example, the VHZ polypeptide may be detected using an anti-VHZ antibody. Such antibodies may be made by means known in the art (as described in further detail below). For example, an anti-VHZ antibody may comprise any commercially available antibody to VHZ, such as but not limited to chicken anti-human VHZ antibody (catalogue numbers LS-C32281, amino acids 35 to 90, LS-C42458, LS-A6806 and LS-C32281, LifeSpan Inc, Seattle, Wash., USA), rabbit anti-human VHZ antibody (catalogue number DS-PB-00676, RayBiotech Inc, Norcross, Ga., USA), chicken anti-human VHZ antibody (catalogue number XW-7857, ProSci Incorporated, Poway, Calif., USA), rabbit anti-human VHZ antibody (catalogue number F4560 and D9840-66A, United States Biological, Swampscott, Mass., USA), chicken anti-human VHZ antibody (catalogue number D9840-66, United States Biological, Swampscott, Mass., USA), rabbit anti-human VHZ antibody (catalogue number AHP1142, AdB Serotec, Oxford, United Kingdom), rabbit anti-human VHZ antibody (catalogue number NB 110-40452, Novus Biologicals, Littleton, Colo., USA), chicken anti-human VHZ antibody (catalogue number NB 100-75328, Novus Biologicals, Littleton, Colo., USA).

This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of VHZ protein, as compared with untreated cells in the same cell population.

Gene expression may also be determined by detecting changes in post-translational processing of VHZ polypeptides or post-transcriptional modification of VHZ nucleic acids. For example, differential phosphorylation of VHZ polypeptides, the cleavage of VHZ polypeptides or alternative splicing of VHZ RNA, and the like may be measured. Levels of expression of gene products such as VHZ polypeptides, as well as their post-translational modification, may be detected using proprietary protein assays or techniques such as 2D polyacrylamide gel electrophoresis.

Assay techniques that can be used to determine levels of VHZ protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

The specimen may be assayed for polypeptides/proteins by immunohistochemical and immunocytochemical staining (see generally Stites and Terr, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654;

3,935,074; 3,984,533; 3,996,345; 4,034,074; 4,098,876; 4,879,219; 5,011,771 and 5,281,521 as well as Sambrook et al, 1992.

Diagnostic Kits

We also provide diagnostic kits for detecting breast cancer in an individual, or susceptibility to breast cancer in an individual.

The diagnostic kit may comprise means for detecting expression, amount or activity of VHZ in the individual, by any means as described in this document. The diagnostic kit may therefore comprise any one or more of the following: a VHZ polynucleotide or a fragment thereof; a complementary nucleotide sequence to VHZ nucleic acid or a fragment thereof; a VHZ polypeptide or a fragment thereof, or an antibody to a VHZ, such as comprising an anti-VHZ antibody against VHZ, e.g., an anti-peptide antibody human VHZ antibody.

The diagnostic kit may comprise instructions for use, or other indicia. The diagnostic kit may further comprise means for treatment or prophylaxis of breast cancer, such as any of the compositions described in this document, or any means known in the art for treating breast cancer. In particular, the diagnostic kit may comprise an anti-VHZ agent as described, for example obtained by screening. The diagnostic kit may comprise a therapeutic drug such as Tamoxifen (Nolvadex) or its variants such as tamoxifen, tamoxifen citrate or any other antiestrogen or estrogen blocker. The therapeutic drug may also comprise an anti-VHZ antibody.

Prophylactic and Therapeutic Methods

We disclose methods of treating an abnormal conditions, such as breast cancer, related to insufficient amounts of VHZ expression or activity. Methods of preventing breast cancer (i.e., prophylaxis) also suitably employ the same or similar approaches.

In general terms, our methods involve manipulation of cancer cells, by modulating (such as down-regulating) the expression, amount or activity of VHZ in the cell. A step of detecting modulated VHZ expression, amount or activity in a cell may be conducted before or after the manipulation step. The detection step may detect up-regulated or down-regulated VHZ expression, amount or activity. Any of the methods of modulating or down-regulating VHZ, as described in detail elsewhere in this document, may be used.

The method may comprise exposing the cell to a suitable siRNA, shRNA or chimera RNAi. For example, a DUSP23 Pre-design Chimera RNAi (catalogue number H00054935-R01, Novus Biologicals, Littleton, Colo., USA) may be employed to down-regulate VHZ mRNA expression. Chimera RNA interference (chimera RNAi) is process by which small interfering RNA/DNA chimera triggers the destruction of mRNA for the original gene. Chimer RNAi is described in detail in Ui-Tei K et al., 2008, Nucleic Acids Res., April 2008; 36: 2136-2151, Naito al. Nucleic Acids Res., July 2005; 33: W589-W591, Ui-Tei K et al., 2004, Nucleic Acids Res. 2004 Feb. 9; 32(3):936-48 and Naito et al. Nucleic Acids Res. 2004 Jul. 1; 32 (Web Server issue): W124-9.

The method may comprise exposing the cell to an anti-VHZ antibody capable of specifically binding to VHZ. Such an antibody may comprise any commercially available anti-VHZ antibody, as set out above.

According to our methods, the cancer cell becomes non-cancerous or the invasive or metastatic cancer cell becomes non-invasive or non-metastatic as a result of the manipulation. The cancer may in particular comprise breast cancer. It may comprise invasive or metastatic cancer such as Invasive Ductal Carcinoma (IDC).

As VHZ is associated with aggressiveness and invasiveness of cancer, the level of VHZ may be detected in a cell of an individual with cancer, in a cancer or non-cancer cell, and the aggressiveness of the cancer assessed. A high level of VHZ amount, expression or activity compared with a normal cell indicates an aggressive or invasive cancer, and a stronger or harsher therapy may therefore be required and chosen. Similarly, a lower level may indicate a less aggressive or invasive therapy.

The approaches described here may be used for therapy of any VHZ related disease in general. VHZ related diseases include proliferative diseases and in particular include cancer. For example, a VHZ related disease may include breast cancer, such as metastatic, invasive or aggressive breast cancer.

A VHZ related disease is defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, etc. By the term "treatment" we mean to also include prophylaxis or alleviation of cancer.

VHZ polypeptide represents a target for inhibition of its function for therapy, particularly in tumour cells and other proliferative cells.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leimyosarcoma, rhabdomyosarcoma, colon carcinoma, ovarian cancer, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neutroblastoma and retinoblastoma.

One possible approach for therapy of such disorders is to express anti-sense constructs directed against VHZ polynucleotides as described here, and administering them to tumour cells, to inhibit gene function and prevent the tumour cell from growing or progressing.

Anti-sense constructs may be used to inhibit gene function to prevent growth or progression in a proliferative cell. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit Rev Oncog* 3(1-2):175-231, the teachings of which document are specifically incorporated by reference.

In a particular example, breast cancer may be treated or prevented by reducing the amount, expression or activity of VHZ in whole or in part, for example by siRNAs capable of binding to and destroying VHZ mRNA. We specifically provide for an anti-VHZ agent which downregulates VHZ by RNA interference. The anti-VHZ agent may comprise a Small Interfering RNA (siRNA) or Short Hairpin RNA (shRNA). It may comprise a chimera RNAi, such as a DUSP23 Pre-design Chimera RNAi (catalogue number H00054935-R01, Novus Biologicals, Littleton, Colo., USA).

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., *Nature* 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the VHZ nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of a VHZ polynucleotide can be introduced into or expressed in oocytes and cells of a candidate organism to interfere with VHZ activity.

Other methods of modulating VHZ gene expression are known to those skilled in the art and include dominant negative approaches. Thus, another approach is to use non-functional variants of VHZ polypeptide in this document that compete with the endogenous gene product resulting in inhibition of function. One example of a non-functional variant of VHZ is a mutation to cysteine at a position 95 of (or corresponding to) the human sequence. The Examples show the generation and use of a C95S variant of VHZ which is defective in phosphatase and associated biological activities.

VHZ gene expression may also be modulated by as introducing peptides or small molecules which inhibit gene expression or functional activity. Thus, compounds identified by the assays described here as binding to or modulating, such as down-regulating, the amount, activity or expression of VHZ polypeptide may be administered to tumour or proliferative cells to prevent the function of VHZ polypeptide. Such a compound may be administered along with a pharmaceutically acceptable carrier in an amount effective to down-regulate expression or activity VHZ, or by activating or down-regulating a second signal which controls VHZ expression, activity or amount, and thereby alleviating the abnormal condition.

Suitable antibodies against VHZ polypeptide as described herein may also be used as therapeutic agents. An anti-VHZ antibody may comprise a rabbit anti-VHZ antibody against VHZ. Furthermore, the anti-VHZ antibody may comprise any one or more of the following: chicken anti-human VHZ antibody (catalogue numbers LS-C32281, amino acids 35 to 90, LS-C42458, LS-A6806 and LS-A6803, LS-C32281, LifeSpan Inc, Seattle, Wash., USA), rabbit anti-human VHZ antibody (catalogue number DS-PB-00676, RayBiotech Inc, Norcross, Ga., USA), chicken anti-human VHZ antibody (catalogue number XW-7857, ProSci Incorporated, Poway, Calif., USA), rabbit anti-human VHZ antibody (catalogue number F4560 and D9840-66A, United States Biological, Swampscott, Mass., USA), chicken anti-human VHZ antibody (catalogue number D9840-66, United States Biological, Swampscott, Mass., USA), rabbit anti-human VHZ antibody (catalogue number AHP1142, AdB Serotec, Oxford, United Kingdom), rabbit anti-human VHZ antibody (catalogue number NB110-40452, Novus Biologicals, Littleton, Colo., USA), chicken anti-human VHZ antibody (catalogue number NB100-75328, Novus Biologicals, Littleton, Colo., USA).

Alternatively, gene therapy may be employed to control the endogenous production of VHZ by the relevant cells such as breast cells in the subject. For example, a polynucleotide encoding a VHZ siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-VHZ siRNA such that the packaging cell now produces infectious viral particles containing the sequence of interest. These producer cells may be administered to a subject for engineering cells in vivo and regulating expression of the VHZ polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd. (1996).

In some embodiments, the level of VHZ is decreased in a breast cell. Furthermore, in such embodiments, treatment may be targeted to, or specific to, breast cells. The expression of VHZ may be specifically decreased only in diseased breast cells (i.e., those cells which are cancerous), and not substantially in other non-diseased breast cells. In these methods, expression of VHZ may be not substantially reduced in other cells, i.e., cells which are not breast cells. Thus, in such embodiments, the level of VHZ remains substantially the same or similar in non-breast cells in the course of or following treatment.

Breast cell specific reduction of VHZ levels may be achieved by targeted administration, i.e., applying the treatment only to the breast cells and not other cells. However, in other embodiments, down-regulation of VHZ expression in breast cells (and not substantially in other cell or tissue types) is employed. Such methods may advantageously make use of breast specific expression vectors, for breast specific expression of for example siRNAs, as described in further detail below.

Breast-specific Expression of a Transgene (Anti-VHZ siRNA)

Cancer gene therapy has to selectively target tumour tissues so as to reduce undesired side effects in normal tissue. Targeting transgene expression to malignant tissues requires the use of specific regulatory elements including promoters based on tumour biology, tissue-specific promoters and inducible regulatory elements (A1).

Promoters Based on Tumour Biology

Certain genes are upregulated in breast cancer. The promoters of these genes can be used to drive tumour-selective expression of a transgene using a recombinant replication-defective retroviral vectors. Examples of such genes include the vascular endothelial growth factor (VEGF), vascular endothelial growth factor receptor-1 (VEGFR-1) and VEGFR-2, which are known to be upregulated in breast cancer in a tumour-stage dependent manner (A2). c-erbB2 oncogene is selectively upregulated in breast carcinomas (A3, A6). L-plastin, a human actin-binding protein is constitutively and abundantly expressed in malignant epithelial cells but not in normal tissue, except for low-level expression in mature hematopoietic cells (A4). Anti-apoptotic gene Bcl-2 has been found to be upregulated in breast cancer cells (A5). Human breast tumours express high levels of MUC1 compared to normal breast tissues (A7).

Tissue Specific Promoters

Certain genes are expressed specifically in breast tissues. Examples of such genes are the human α-lactalbumin (ALA) and ovine β-lactoglobulin (BLG). The promoters of such genes can be used to drive the expression of transgenes in adenoviral vectors in a breast cancer cell-specific manner (A8). Gene therapy for breast carcinoma may be approached by tailoring a virus with affinity to this tissue, such as the mouse mammary tumour virus (MMTV). The glucorticoid-responsive long terminal repeats (LTR) of this retrovirus can be used as promoter for glucocorticoid-induced the expression of a transgene (A9).

Inducible Promoters

Inducible promoters are used as mediators of transient transgene expression. Various stress genes are upregulated in breast tumours upon irradiation or chemotherapeutic treatment. Examples of such stress genes are heat shock protein (HSP) (A10) and multidrug resistance gene-1 (MDR-1) (A11). The promoters of these genes can therefore be used to drive the tumour specific expression of a transgene in breast cancers that have been subjected to irradiation or chemotherapy.

Transcriptionally targeted gene therapy is usually achieved by direct intratumour injection of a replication-defective adenoviral expression vector containing the transgene of interest (A6, A12, A13). The transgene can also be delivered by intratumoural injection as a lipid complex with cationic liposomes (A14, A15).

Breast Cancer

According to the methods and compositions described here, VHZ is useful for diagnosing or treating breast cancer. Where this document refers to "cancer", this should be taken to include metastatic, aggressive or invasive cancer. For example, the cancer may be a cancer associated with VHZ over-expression. By this we mean that a cancer cell of the cancer in question displays an elevated level of expression or activity (or both) of VHZ, as compared to a non-cancer cell.

There are several types of breast cancer. The most common is ductal carcinoma, which begins in the lining of the milk ducts of the breast. Another type, lobular carcinoma, begins in the lobules where breast milk is produced. If a malignant tumor invades nearby tissue, it is known as infiltrating or invasive cancer. When breast cancer spreads outside the breast, cancer cells often are found in the lymph nodes under the arm. Breast cancer cells may spread beyond the breast such as to other lymph nodes, the bones, liver, or lungs.

The recognised stages of breast cancer comprise:

Stage 0: Very early breast cancer. This type of cancer has not spread within or outside the breast. It is sometimes called DCIS, LCIS, or breast cancer in situ or non-invasive cancer.

Stage I: The cancer is no larger than about 1 inch in size and has not spread outside the breast. (also described as early breast cancer.)

Stage II: The presence of any of the following: the cancer is no larger than 1 inch, but has spread to the lymph nodes under the arm; the cancer is between 1 and 2 inches. It may or may not have spread to the lymph nodes under the arm; the cancer is larger than 2 inches, but has not spread to the lymph nodes under the arm.

Stage III and Stage IIIA: The presence of any of the following: the cancer is smaller than 2 inches and has spread to the lymph nodes under the arm, the cancer also is spreading further to other lymph nodes; the cancer is larger than 2 inches and has spread to the lymph nodes under the arm.

Stage IIIB: The presence of any of the following: the cancer has spread to tissues near the breast (skin, chest wall, including the ribs and the muscles in the chest); the cancer has spread to lymph nodes inside the chest wall along the breast bone.

Stage IV: The cancer has spread to other parts of the body, most often the bones, lungs, liver, or brain. Or, the tumor has spread locally to the skin and lymph nodes inside the neck, near the collarbone.

Inflammatory Breast Cancer: Inflammatory breast cancer is a rare, but very serious, aggressive type of breast cancer. The breast may look red and feel warm. There may be ridges, welts, or hives on the breast; or the skin may look wrinkled. It is sometimes misdiagnosed as a simple infection.

Recurrent Breast Cancer: Recurrent disease means that the cancer has come back (recurred) after it has been treated. It may come back in the breast, in the soft tissues of the chest (the chest wall), or in another part of the body.

Breast Cancer In Situ—DCIS and LCIS

Many breast cancers being found are very early cancers known as breast cancer in situ or noninvasive cancer. Most of these cancers are found by mammography. These very early cell changes may become invasive breast cancer. Two types of breast cancer in situ include the following:

DCIS (ductal carcinoma in situ), which means that abnormal cells are found only in the lining of a milk duct of the breast. The abnormal cells have not spread outside the duct. They have not spread within the breast, beyond the breast, to the lymph nodes under the arm, or to other parts of the body. There are several types of DCIS. If not removed, some types may change over time and become invasive cancers. Some may never become invasive cancers. (DCIS is sometimes called intraductal carcinoma.)

LCIS (lobular carcinoma in situ), which means that abnormal cells are found in the lining of a milk lobule. Although LCIS is not considered to be actual breast cancer at this noninvasive stage, it is a warning sign of increased risk of developing invasive cancer. LCIS is sometimes found when a biopsy is done for another lump or unusual change that is found on a mammogram. Patients with LCIS have a 25 percent chance of developing breast cancer in either breast during the next 25 years.

Microcalcifications are very small specks of calcium that can't be felt, but can be seen on a mammogram. They are formed by rapidly dividing cells. When they are clustered in one area of the breast, this could be an early sign of breast cancer in situ. About half of the breast cancers found by mammography appear as clusters of microcalcifications. The other half appear as lumps.

Diagnosis

Our diagnostic methods may be used in conjunction with any known method of diagnosis of breast cancer, including detecting of mutations in either or both of the known breast cancer genes BRCA1 and BRCA2. Alternatively, or in addition, the diagnosis may be carried out by detection of Her2 expression, for example by use of anti-Her2 antibody.

Treatment

Known treatments for breast cancer may consist of any one or more of the following: Surgery, radiation therapy, chemotherapy, high-dose chemotherapy, hormonal therapy and immunotherapy. Accordingly, any of the treatment methods described here may be combined with any one or more of the preceding known therapies. In addition, any one or more of the following general therapies known to be effective for treatment or alleviation of cancer may be used.

Nonspecific Immunomodulating Agents

Nonspecific immunomodulating agents are substances that stimulate or indirectly augment the immune system. Often, these agents target key immune system cells and cause secondary responses such as increased production of cytokines and immunoglobulins. Two nonspecific immunomodulating agents used in cancer treatment are *bacillus* Calmette-Guerin (BCG) and levamisole. The anti-VHZ agents described here may be used in conjunction with any of such nonspecific immunomodulating agents.

Biological Response Modifiers

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, and vaccines. The anti-VHZ agents described here may be used in conjunction with any of such biological response modifiers.

Interferons (IFN)

There are three major types of interferons—interferon alpha, interferon beta, and interferon gamma; interferon alpha is the type most widely used in cancer treatment.

Interferons can improve the way a cancer patient's immune system acts against cancer cells. In addition, interferons may act directly on cancer cells by slowing their growth or promoting their development into cells with more normal behavior. Some interferons may also stimulate NK cells, T cells, and macrophages, boosting the immune system's anticancer function.

The anti-VHZ agents described here may be used in conjunction with any of such interferons.

Interleukins (IL)

Like interferons, interleukins are cytokines that occur naturally in the body. Many interleukins have been identified; interleukin-2 (IL-2 or aldesleukin) has been the most widely studied in cancer treatment. IL-2 stimulates the growth and activity of many immune cells, such as lymphocytes, that can destroy cancer cells.

The anti-VHZ agents described here may be used in conjunction with any of such interleukins.

Colony-Stimulating Factors (CSFs)

Colony-stimulating factors (CSFs) (sometimes called hematopoietic growth factors) usually do not directly affect tumor cells; rather, they encourage bone marrow stem cells to divide and develop into white blood cells, platelets, and red blood cells. Bone marrow is critical to the body's immune system because it is the source of all blood cells.

G-CSF (filgrastim) and GM-CSF (sargramostim) can increase the number of white blood cells, thereby reducing the risk of infection in patients receiving chemotherapy. G-CSF and GM-CSF can also stimulate the production of stem cells in preparation for stem cell or bone marrow transplants; Erythropoietin can increase the number of red blood cells and reduce the need for red blood cell transfusions in patients receiving chemotherapy; and Oprelvekin can reduce the need for platelet transfusions in patients receiving chemotherapy.

The anti-VHZ agents described here may be used in conjunction with any of such colony-stimulating factors.

Monoclonal Antibodies (MOABs)

Herceptin is used to treat metastatic breast cancer in patients with tumors that produce excess amounts of a protein called HER-2. (Approximately 25 percent of breast cancer tumors produce excess amounts of HER-2). In particular embodiments, the methods of treatment described here may be used in combination with administration of anti-Her2 antibody, for example, Herceptin, to the individual concerned.

The anti-VHZ agents described here may be used in conjunction with any of such monoclonal antibodies.

Her2/Neu

The HER-2/neu (erbB-2) gene product is a 185-kDA transmembrane receptor tyrosine kinase that belongs to the family of receptors for epidermal growth factor. It is described in some detail in Reese, D. M., et al., Stem Cells, 15, 1-8 (1997) which is incorporated herein by reference.

Recently, enormous attention has been given to the importance of HER-2/neu in breast cancer. HER-2/neu is overexpressed in 20-30% of human breast cancers and the increased expression has been associated with poor prognosis. The discovery of this has led to the development of HERCEPTIN, an antibody to HER-2/neu, which in tests has been found to lengthen remission time in metastatic breast cancer. HER-2/neu is a cell-surface receptor that transmits growth signals to the cell nucleus. HERCEPTIN appears to block these signals thereby apparently inhibiting proliferation of cells mediated by HER-2/neu in HER-2/neu positive breast cancer.

Overexpression of HER-2/neu has also been found in a portion of ovarian cancers, gastric cancers, endometrial cancers, salivary cancers, pancreatic cancers, prostate cancers, colorectal cancers, and non-small-cell lung cancers. The other cancers associated with overexpression of HER-2-neu are potentially treatable with HERCEPTIN.

Accordingly, our methods of diagnosis may be combined with detection of over-expression of Her2 in an individual. Likewise, the methods of treatment described here may include administration of Herceptin to an individual, in addition to decreasing activity, amount or expression of VHZ. We therefore provide a combination of VHZ nucleic acid or VHZ polypeptide, together with an anti-Her2 antibody. We also provide a combination of an anti-VHZ antibody together with an anti-Her2 antibody. In some embodiments, the anti-Her2 antibody comprises Herceptin.

Screening for Anti-VHZ Agents

Identifying VHZ Modulators, Agonists and Antagonists

Antagonists, in particular, small molecules may be used to specifically inhibit VHZ for use as anti-VHZ agents.

We therefore disclose VHZ antagonists and small molecule VHZ inhibitors, as well as assays for screening for these. Antagonists of VHZ may be screened by detecting modulation, such as down regulation, of binding or other VHZ activity. We therefore provide a compound capable of down-regulating the expression, amount or activity VHZ polypeptide. Such a compound may be used in the methods and compositions described here for treating or preventing cancer, particularly breast cancer.

VHZ may therefore be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991). Furthermore, screens may be conducted to identify factors which influence the expression of VHZ, in particular in breast cells.

In general, the assays for agonists and antagonists rely on determining the effect of candidate molecules on one or more activities of VHZ. An assay may involve assaying VHZ activity in the presence of a candidate molecule, and optionally in the absence of the candidate molecule, or in the presence of a molecule known to inhibit or activate a VHZ activity.

We have demonstrated that expression of VHZ is increased in breast cancer cells; accordingly, control of VHZ expression may be employed to treat breast cancer and other cancers. Therefore, it is desirous to find compounds and drugs which stimulate the expression and/or activity of VHZ, or which can inhibit the function of this protein. In general, agonists and antagonists are employed for therapeutic and prophylactic purposes for any known cancer, in particular, breast cancer.

By "down-regulation" we include any negative effect on the behaviour being studied; this may be total or partial. Thus, where binding is being detected, candidate antagonists are capable of reducing, ameliorating, or abolishing the binding between two entities. The down-regulation of binding (or any other activity) achieved by the candidate molecule may be at least 10%, such as at least 20%, at least 30%, at least 40%, at least 50%, at least 60%, at least 70%, at least 80%, at least 90% or more compared to binding (or which ever activity) in the absence of the candidate molecule. Thus, a candidate molecule suitable for use as an antagonist is one which is capable of reducing by 10% more the binding or other activity.

The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Examples of potential antagonists of VHZ include antibodies, small molecules, nucleotides and their analogues, including purines and purine analogues, oligonucleotides or proteins which are closely related to a binding partner of VHZ, e.g., a fragment of the binding partner, or small molecules which bind to the VHZ polypeptide but do not elicit a response, so that the activity of the polypeptide is prevented, etc.

Screening Kits

The materials necessary for such screening to be conducted may be packaged into a screening kit.

Such a screening kit is useful for identifying agonists, antagonists, ligands, receptors, substrates, enzymes, etc. for VHZ polypeptides or compounds which decrease or enhance the production of VHZ. The screening kit may comprise: (a) a VHZ polypeptide; (b) a recombinant cell expressing a VHZ polypeptide; or (c) an antibody to VHZ polypeptide. The screening kit may comprise a library. The screening kit may comprise any one or more of the components needed for screening, as described below. The screening kit may optionally comprise instructions for use.

Screening kits may also be provided which are capable of detecting VHZ expression at the nucleic acid level. Such kits may comprise a primer for amplification of VHZ, or a pair of primers for amplification. The primer or primers may be chosen from any suitable sequence, for example a portion of the VHZ sequence. Methods of identifying primer sequences are well known in the art, and the skilled person will be able to design such primers with ease. The kits may comprise a nucleic acid probe for VHZ expression, as described in this document. The kits may also optionally comprise instructions for use.

Rational Design

Rational design of candidate compounds likely to be able to interact with VHZ may be based upon structural studies of the molecular shapes of a VHZ polypeptide. One means for determining which sites interact with specific other proteins is a physical structure determination, e.g., X-ray crystallography or two-dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Polypeptide Binding Assays

Modulators and antagonists of VHZ activity or expression may be identified by any means known in the art.

In their simplest form, the assays may simply comprise the steps of mixing a candidate compound with a solution containing a VHZ polypeptide to form a mixture, measuring activity of VHZ polypeptide in the mixture, and comparing the activity of the mixture to a standard.

Furthermore, molecules may be identified by their binding to VHZ, in an assay which detects binding between VHZ and the putative molecule.

One type of assay for identifying substances that bind to a VHZ polypeptide described here involves contacting the VHZ polypeptide, which is immobilised on a solid support, with a non-immobilised candidate substance determining whether and/or to what extent the VHZ polypeptide of interest and candidate substance bind to each other. Alternatively, the candidate substance may be immobilised and the VHZ polypeptide as set out in this document non-immobilised.

The binding of the substance to the VHZ polypeptide can be transient, reversible or permanent. The substance may bind to the polypeptide with a Kd value which is lower than the Kd value for binding to control polypeptides (e.g., polypeptides known to not be involved in cancer growth or progression). The Kd value of the substance may be 2 fold less than the Kd value for binding to control polypeptides, such as a Kd value 100 fold less or a Kd 1000 fold less than that for binding to the control polypeptide.

In an example assay method, the VHZ polypeptide may be immobilised on beads such as agarose beads. Typically this may be achieved by expressing the VHZ polypeptide as a GST-fusion protein in bacteria, yeast or higher eukaryotic cell lines and purifying the GST-VHZ fusion protein from crude cell extracts using glutathione-agarose beads (Smith and Johnson, 1988; *Gene* 67(10):31-40). As a control, binding of the candidate substance, which is not a GST-fusion protein, to an immobilised polypeptide may be determined in the absence of the VHZ polypeptide. The binding of the candidate substance to the immobilised VHZ polypeptide may then be determined. This type of assay is known in the art as a GST pulldown assay. Again, the candidate substance may be immobilised and the VHZ polypeptide non-immobilised.

It is also possible to perform this type of assay using different affinity purification systems for immobilising one of the components, for example Ni-NTA agarose and histidine-tagged components.

Binding of the polypeptide to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, such as from 1 to 100 nmol/ml. In the case of antibodies, the final concentration used is typically from 100 to 500 µg/ml, such as from 200 to 300 µg/ml.

Modulators and antagonists of VHZ may also be identified by detecting modulation of binding between VHZ and any molecule to which this polypeptide binds, or modulation of any activity consequential on such binding or release.

Cell Based Assays

A cell based assay may simply test binding of a candidate compound wherein adherence to the cells bearing the VHZ polypeptide is detected by means of a label directly or indirectly associated with the candidate compound or in an assay involving competition with a labeled competitor.

Further, these assays may test whether the candidate compound results in a signal generated by binding to the VHZ polypeptide, using detection systems appropriate to the cells bearing the polypeptides at their surfaces. Inhibitors of activation are generally assayed in the presence of a known agonist and the effect on activation by the agonist by the presence of the candidate compound is observed.

Another method of screening compounds utilises eukaryotic or prokaryotic host cells which are stably transformed with recombinant DNA molecules expressing a library of compounds. Such cells, either in viable or fixed form, can be used for standard binding-partner assays. See also Parce et al. (1989) Science 246:243-247; and Owicki et al. (1990) Proc. Nat'l Acad. Sci. USA 87; 4007-4011, which describe sensitive methods to detect cellular responses.

Competitive assays are particularly useful, where the cells expressing the library of compounds are contacted or incubated with a labelled antibody known to bind to a VHZ polypeptide, such as $^{125}$I-antibody, and a test sample such as a candidate compound whose binding affinity to the binding composition is being measured. The bound and free labelled binding partners for the VHZ polypeptide are then separated to assess the degree of binding. The amount of test sample bound is inversely proportional to the amount of labelled antibody binding to the VHZ polypeptide.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

The assays may involve exposing a candidate molecule to a cell, such as a breast cell, and assaying expression of VHZ by any suitable means. Molecules which down-regulate the expression of VHZ in such assays may be optionally chosen for further study, and used as drugs to down-regulate VHZ expression. Such drugs may be usefully employed to treat or prevent breast cancer.

cDNA encoding VHZ protein and antibodies to the proteins may also be used to configure assays for detecting the effect of added compounds on the production of VHZ mRNA and protein in cells. For example, an ELISA may be constructed for measuring secreted or cell associated levels of VHZ polypeptide using monoclonal and polyclonal antibodies by standard methods known in the art, and this can be used to discover agents which may inhibit or enhance the production of VHZ protein (also called antagonist or agonist, respectively) from suitably manipulated cells or tissues. Standard methods for conducting screening assays are well understood in the art.

Activity Assays

Assays to detect modulators or antagonists typically involve detecting modulation of any activity of VHZ, in the presence, optionally together with detection of modulation of activity in the absence, of a candidate molecule.

Assays which detect specific biological activities of VHZ, such as phosphatase activity, may be used. The assays typically involve contacting a candidate molecule (e.g., in the form of a library) with VHZ whether in the form of a polypeptide, a nucleic acid encoding the polypeptide, or a cell, organelle, extract, or other material comprising such, with a candidate modulator. The relevant activity of VHZ (such as phosphatase activity, as described below) may be detected, to establish whether the presence of the candidate modulator has any effect.

Phosphatase assays are known in the art and are described in Wu et al (2004), Int J Biochem Cell Biol. 36(8):1542-53 and Alonso et al (2004). J Biol. Chem. 20; 279(34):35768-74. Such assays comprise assaying the ability of VHZ to de-phosphorylate a suitable substrate such as p-nitrophenyl phosphate, or as oligopeptides containing phospho-tyrosine and phospho-threonine residues. The assays may be performed in the presence or absence of a candidate modulator and the appropriate activity detected to detect modulation of VHZ activity and hence identification of a candidate modulator and/or antagonist of VHZ.

Promoter binding assays to detect candidate modulators which bind to and/or affect the transcription or expression of VHZ may also be used. Candidate modulators may then be chosen for further study, or isolated for use. Details of such screening procedures are well known in the art, and are for example described in, *Handbook of Drug Screening*, edited by Ramakrishna Seethala, Prabhavathi B. Fernandes (2001, New York, N.Y., Marcel Dekker, ISBN 0-8247-0562-9).

The screening methods described here may employ in vivo assays, although they may be configured for in vitro use. In vivo assays generally involve exposing a cell comprising VHZ to the candidate molecule. In in vitro assays, VHZ is exposed to the candidate molecule, optionally in the presence of other components, such as crude or semi-purified cell extract, or purified proteins. Where in vitro assays are conducted, these may employ arrays of candidate molecules (for example, an arrayed library). In vivo assays may be employed. Therefore, the VHZ polypeptide may be comprised in a cell, such as heterologously. Such a cell may be a transgenic cell, which has been engineered to express VHZ as described above.

Where an extract is employed, it may comprise a cytoplasmic extract or a nuclear extract, methods of preparation of which are well known in the art.

It will be appreciated that any component of a cell comprising VHZ may be employed, such as an organelle. One embodiment utilises a cytoplasmic or nuclear preparation, e.g., comprising a cell nucleus which comprises VHZ as described. The nuclear preparation may comprise one or more nuclei, which may be permeabilised or semi-permeabilised, by detergent treatment, for example.

Thus, in a specific embodiment, an assay format may include the following: a multiwell microtitre plate is set up to include one or more cells expressing VHZ polypeptide in each well; individual candidate molecules, or pools of candidate molecules, derived for example from a library, may be added to individual wells and modulation of VHZ activity measured. Where pools are used, these may be subdivided in to further pools and tested in the same manner. VHZ activity, for example binding activity or transcriptional co-activation activity, as described elsewhere in this document may then be assayed.

Alternatively or in addition to the assay methods described above, "subtractive" procedures may also be used to identify modulators or antagonists of VHZ. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising VHZ (or a component thereof) as described.

Thus, for example, an 'immunodepletion' assay may be conducted to identify such modulators as follows. A cytoplasmic or nuclear extract may be prepared from a suitable cell. The extract may be depleted or fractionated to remove putative modulators, such as by use of immunodepletion with appropriate antibodies. If the extract is depleted of a modulator, it will lose the ability to affect VHZ function or activity or expression. A series of subtractions and/or depletions may be required to identify the modulators or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In one embodiment, more than one candidate molecule may be screened simultaneously. A library of candidate molecules may be generated, for example, a small molecule library, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising VHZ may be exposed to individual members of the library, and effect on the VHZ activity determined. Array technology may be employed for this purpose. The cells may be spatially separated, for example, in wells of a microtitre plate.

In an embodiment, a small molecule library is employed. By a "small molecule", we refer to a molecule whose molecular weight may be less than about 50 kDa. In particular embodiments, a small molecule may have a molecular weight which is less than about 30 kDa, such as less than about 15 kDa or less than 10 kDa or so. Libraries of such small molecules, here referred to as "small molecule libraries" may contain polypeptides, small peptides, for example, peptides of 20 amino acids or fewer, for example, 15, 10 or 5 amino acids, simple compounds, etc.

Alternatively or in addition, a combinatorial library, as described in further detail below, may be screened for modulators or antagonists of VHZ. Assays for VHZ activity are described above.

Libraries

Libraries of candidate molecules, such as libraries of polypeptides or nucleic acids, may be employed in the screens for VHZ antagonists and inhibitors described here. Such libraries are exposed to VHZ protein, and their effect, if any, on the activity of the protein determined.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. U.S.A.,* 88: 4363; Clackson et al. (1991) *Nature,* 352: 624; Lowman et al. (1991) *Biochemistry,* 30: 10832; Burton et al. (1991) *Proc. Natl. Acad. Sci. U.S.A.,* 88: 10134; Hoogenboom et al. (1991) Nucleic Acids Res., 19: 4133; Chang et al. (1991) *J. Immunol.,* 147: 3610; Breitling et al. (1991) *Gene,* 104: 147; Marks et al. (1991) supra; Barbas et al. (1992) supra; Hawkins and Winter (1992) *J. Immunol.,* 22: 867; Marks et al., 1992, *J. Biol. Chem.,* 267: 16007; Lerner et al. (1992) *Science,* 258: 1313, incorporated herein by reference). Such techniques may be modified if necessary for the expression generally of polypeptide libraries.

One particularly advantageous approach has been the use of scFv phage-libraries (Bird, R. E., et al. (1988) *Science* 242: 423-6, Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) supra; Marks et al. (1991)

supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science,* 246: 1275; Caton and Koprowski (1990) *Proc. Natl. Acad. Sci. U.S.A.,* 87; Mullinax et al. (1990) *Proc. Natl. Acad. Sci. U.S.A.,* 87: 8095; Persson et al. (1991) *Proc. Natl. Acad. Sci. U.S.A.,* 88: 2432) and are of use in the methods and compositions described here. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science,* 251: 767; Dower and Fodor (1991) *Ann. Rep. Med. Chem.,* 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science,* 249: 505; Ellington and Szostak (1990) *Nature,* 346: 818). A similar technique may be used to identify DNA sequences which bind a predetermined human transcription factor (Thiesen and Bach (1990) *Nucleic Acids Res.,* 18: 3203; Beaudry and Joyce (1992) *Science,* 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of inhibiting VHZ.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 235-282. Reference is also made to *Combinatorial peptide library protocols* (edited by Shmuel Cabilly, Totowa, N.J.: Humana Press, c1998. *Methods in Molecular Biology* v. 87). Specific combinatorial libraries and methods for their construction are disclosed in U.S. Pat. No. 6,168,914 (Campbell, et al), as well as in Baldwin et al. (1995), "Synthesis of a Small Molecule Library Encoded with Molecular Tags," J. Am. Chem. Soc. 117:5588-5589, and in the references mentioned in those documents.

In one embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone methylation enzymes), or DNA modification, for example, DNA methylation or demethylation.

Further references describing chemical combinatorial libraries, their production and use include those available from the worldwide web at netsci.org/Science/Combichem, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Anti-VHZ Antibodies

Anti-VHZ agents, including antagonists or modulators of VHZ, which may be used to regulate the activity of this protein (for example, for methods of treating or preventing diseases such as cancer as described in this document) may include antibodies against the VHZ protein.

We therefore provide for antibodies which bind to a VHZ polypeptide, fragment, homologue, variant or derivative thereof. Such antibodies are useful in detecting VHZ expression, and in particular in diagnosing a VHZ associated disease such as breast cancer. Other antibodies include those which have therapeutic activity, i.e., which are may be used in a therapeutic manner to treat, manage or prevent any VHZ associated disease, including breast cancer.

An antibody against VHZ may be generated as described in the Examples, by immunisation with a peptide RRLRPGSIETYEQEK (SEQ ID NO: 3) corresponding to amino acid residues (126-140) of human VHZ.

Examples of antibodies capable of binding to VHZ include chicken anti-human VHZ antibody (catalogue numbers LS-C32281, amino acids 35 to 90, LS-C42458, LS-A6806 and LS-A6803, LS-C32281, LifeSpan Inc, Seattle, Wash., USA), rabbit anti-human VHZ antibody (catalogue number DS-PB-00676, RayBiotech Inc, Norcross, Ga., USA), chicken anti-human VHZ antibody (catalogue number XW-7857, ProSci Incorporated, Poway, Calif., USA), rabbit anti-human VHZ antibody (catalogue number F4560 and D9840-66A, United States Biological, Swampscott, Mass., USA), chicken anti-human VHZ antibody (catalogue number D9840-66, United States Biological, Swampscott, Mass., USA), rabbit anti-human VHZ antibody (catalogue number AHP1142, AdB Serotec, Oxford, United Kingdom), rabbit anti-human VHZ antibody (catalogue number NB 110-40452, Novus Biologicals, Littleton, Colo., USA), chicken anti-human VHZ antibody (catalogue number NB 100-75328, Novus Biologicals, Littleton, Colo., USA).

Furthermore, antibodies which are specific for VHZ may be generated against any suitable epitope, for example, an epitope derived from the VHZ protein. The sequence of a suitable fragment of VHZ may comprise residue C95 of VHZ and any epitope from this sequence may be used for the generation of specific VHZ antibodies.

For the purposes of this document, the term "antibody" refers to complete antibodies or antibody fragments capable of binding to a selected target. Unless specified to the contrary, the term includes but is not limited to, polyclonal, monoclonal, natural or engineered antibodies including chimeric, CDR-grafted and humanised antibodies, and artificially selected antibodies produced using phage display or alternative techniques. The term also includes single chain, Fab fragments and fragments produced by a Fab expression library. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Small fragments, such as Fv and ScFv, possess advantageous properties for diagnostic and therapeutic applications on account of their small size and consequent superior tissue distribution.

The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used. Neutralizing antibodies, i.e., those which inhibit any biological activity of VHZ, may be used for diagnostics and therapeutics.

The antibodies described here may be altered antibodies comprising an effector protein such as a label. Labels which allow the imaging of the distribution of the antibody in vivo or in vitro may be used. Such labels may be radioactive labels or radioopaque labels, such as metal particles, which are readily visualisable within an embryo or a cell mass. Moreover, they may be fluorescent labels or other labels which are visualisable on tissue samples.

Antibodies may be produced by standard techniques, such as by immunisation or by using a phage display library. Such an antibody may be capable of binding specifically to the VHZ protein or homologue, fragment, etc.

Polyclonal Antibodies

If polyclonal antibodies are desired, a selected mammal (e.g., mouse, rabbit, goat, horse, etc.) may be immunised with an immunogenic composition comprising a VHZ polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed if purified the substance amino acid sequence is administered to immunologically compromised individuals for the purpose of stimulating systemic defence.

Serum from the immunised animal is collected and treated according to known procedures. If serum containing polyclonal antibodies to an epitope obtainable from a VHZ polypeptide contains antibodies to other antigens, the polyclonal antibodies can be purified by immunoaffinity chromatography. Techniques for producing and processing polyclonal antisera are known in the art. In order that such antibodies may be made, we also provide VHZ amino acid sequences or fragments thereof haptenised to another amino acid sequence for use as immunogens in animals or humans.

Monoclonal Antibodies

Monoclonal antibodies directed against epitopes obtainable from a VHZ polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

Recombinant DNA technology may be used to improve the antibodies as described here. Thus, chimeric antibodies may be constructed in order to decrease the immunogenicity thereof in diagnostic or therapeutic applications. Such techniques comprise splicing of mouse antibody genes to human antibody genes to obtain a molecule with appropriate antigen specificity and biological activity (Morrison et al (1984) Proc Natl Acad Sci 81:6851-6855; Neuberger et al (1984) Nature 312:604-608; Takeda et al (1985) Nature 314:452-454). Moreover, immunogenicity may be minimised by humanising the antibodies by CDR grafting [see European Patent Application 0 239 400 (Winter)] and, optionally, framework modification [EP 0 239 400].

Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from a VHZ polypeptide or peptide are particularly useful in diagnosis. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for the polypeptide or peptide may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275-128 1).

Techniques for the production of single chain antibodies (U.S. Pat. No. 4,946,778) can also be adapted to produce single chain antibodies to VHZ polypeptides. Also, transgenic mice, or other organisms including other mammals, may be used to express humanized antibodies.

The above-described antibodies may be employed to isolate or to identify clones expressing the polypeptide or to purify the polypeptides by affinity chromatography.

Recombinant Techniques of Antibody Production Recombinant DNA technology may be used to produce the antibodies according to established procedure, in bacterial or mammalian cell culture. The selected cell culture system may secrete the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules are described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the antigen, or fragments thereof, or with Protein-A.

Hybridoma cells secreting the monoclonal antibodies are also provided. Hybridoma cells may be genetically stable, secrete monoclonal antibodies of the desired specificity and can be activated from deep-frozen cultures by thawing and recloning.

Also included is a process for the preparation of a hybridoma cell line secreting monoclonal antibodies directed to the VHZ polypeptide, characterised in that a suitable mammal, for example a Balb/c mouse, is immunised with a one or more VHZ polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with VHZ are fused with cells of the myeloma cell line PAI or the myeloma cell line Sp2/0-Ag14, the obtained hybrid cells are screened for secretion of the desired antibodies, and positive hybridoma cells are cloned.

We describe a process for the preparation of a hybridoma cell line, characterised in that Balb/c mice are immunised by injecting subcutaneously and/or intraperitoneally between 10 and $10^7$ and $10^8$ cells expressing VHZ and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, such as polyethylene glycol. The myeloma cells may be fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to VHZ as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to VHZ can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. The modification(s) may be outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly E. coli, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to VHZ fused to a human constant domain g, for example γ1, γ2, γ3 or γ4, such as γ1 or γ4. Likewise recombinant DNAs comprising an insert coding for a light chain murine variable domain of an antibody directed to VHZ fused to a human constant domain κ or λ, such as κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Use

Anti-VHZ antibodies may be used in method of detecting a VHZ polypeptide present in biological samples by a method which comprises: (a) providing an anti-VHZ antibody; (b) incubating a biological sample with said antibody under conditions which allow for the formation of an antibody-antigen complex; and (c) determining whether antibody-antigen complex comprising said antibody is formed.

Suitable samples include extracts tissues such as brain, breast, ovary, lung, colon, pancreas, testes, liver, muscle and bone tissues or from neoplastic growths derived from such tissues. In particular, a sample may comprise a breast tissue, such as a breast tissue from an individual suspected to be suffering from breast cancer.

Antibodies may be bound to a solid support and/or packaged into kits in a suitable container along with suitable reagents, controls, instructions and the like.

Antibody Delivery

The antibodies against the VHZ protein may be delivered into a cell by means of techniques known in the art, for example by the use of liposomes, polymers, (e.g., polyethylene glycol (PEG), N-(2-hydroxypropyl) methacrylamide (HPMA) copolymers, polyamidoamine (PAMAM) dendrimers, HEMA, linear polyamidoamine polymers etc) etc. The immunoglobulins and/or antibodies may also be delivered into cells as protein fusions or conjugates with a protein capable of crossing the plasma membrane and/or the nuclear membrane. For example, the immunoglobulin and/or target may be fused or conjugated to a domain or sequence from such a protein responsible for the translocational activity. Translocation domains and sequences may include domains and sequences from the HIV-1-trans-activating protein (Tat), Drosophila Antennapedia homeodomain protein and the herpes simplex-1 virus VP22 protein.

Pharmaceutical Compositions and Administration

While it is possible for the anti-VHZ agent, including an VHZ nucleic acid, polypeptide, fragment, homologue, variant or derivative thereof, modulator, agonist or antagonist, a structurally related compound, or an acidic salt of either to be administered alone, the active ingredient may be formulated as a pharmaceutical formulation.

We therefore also disclose pharmaceutical compositions comprising an anti-VHZ agent. Such pharmaceutical compositions are useful for delivery of the anti-VHZ agent such as in the form of a composition as described, to an individual for the treatment or alleviation of symptoms as described.

A pharmaceutical composition in the context of the present document is a composition of matter comprising at least an anti-VHZ agent as an active ingredient.

The pharmaceutical formulations comprise an effective amount of the anti-VHZ agent together with one or more pharmaceutically-acceptable carriers. An "effective amount" is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the anti-VHZ agent is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The active ingredient(s) of a pharmaceutical composition is contemplated to exhibit therapeutic activity, for example, in the alleviation of cancer, tumours, neoplasms and other related diseases. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

The anti-VHZ agent may be administered alone, or in combination with other therapeutic agents. Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

Oral Administration

In some embodiments, the inhibitor of VHZ activity, expression or amount is provided as an oral composition and administered accordingly. The dosage of the inhibitor of VHZ activity, expression or amount may be between about 1 mg/day to about 10 mg/day.

The pharmaceutical composition can be administered in an oral formulation in the form of tablets, capsules or solutions. An effective amount of the oral formulation is administered to patients 1 to 3 times daily until the symptoms of the disease alleviated.

The effective amount of agent depends on the age, weight and condition of a patient. In general, the daily oral dose of agent is less than 1200 mg, and more than 100 mg. The daily oral dose may be about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

The composition may be suitably orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Injectable or Intravenous Administration

In some embodiments, the anti-VHZ agent is provided as an injectable or intravenous composition and administered accordingly. The dosage of the anti-VHZ agent inhibitor may be between about 5 mg/kg/2 weeks to about 10 mg/kg/2 weeks. The anti-VHZ agent inhibitor may be provided in a dosage of between 10-300 mg/day, such as at least 30 mg/day, less than 200 mg/day or between 30 mg/day to 200 mg/day.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

Topical Administration

The pharmaceutical compositions disclosed here include those suitable for topical and oral administration, with topical formulations being preferred where the tissue affected is primarily the skin or epidermis (for example, psoriasis, eczema and other epidermal diseases).

The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the agent composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p.

1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the composition in the topical formulation is in an amount of about 0.5 to 50% by weight of the composition, such as about 1 to 30%, about 2-20%, or about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In:Swine in Biomedical Research (M. E. Tumbleson, Ed.) Plenum, N.Y., 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, a long acting form of agent or composition may be administered using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations described here can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

Parenteral Administration

The active compound may also be administered parenterally or intraperitoneally. Dispersions can also be prepared in glycerol, liquid polyethylene glycols, and mixtures thereof and in oils. In some embodiments, the dispersions may be prepared in 30% Capsitol (CyDex, Inc., Lenexa, Kans., USA). Capsitol is a polyanionic β-cyclodextrin derivative with a sodium sulfonate salt separated from the lipophilic cavity by a butyl ether spacer group, or sulfobutylether (SBE). The cyclodextrin may be SBE7-β-CD.

Adjuvants

The composition may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes.

Prevention of Microorganism Growth

Under ordinary conditions of storage and use, these preparations may contain a preservative to prevent the growth of microorganisms.

The prevention of the action of microorganisms can be brought about by various antibacterial and antifungal agents, for example, parabens, chlorobutanol, phenol, sorbic acid, thirmerosal, and the like. In many cases, it is possible to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the methods of preparation may include vacuum drying and the freeze-drying technique which yield a powder of the active ingredient plus any additional desired ingredient from previously sterile-filtered solution thereof.

Pharmaceutically Acceptable Carrier

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Dosage Unit Forms

It is especially advantageous to formulate pharmaceutical compositions in dosage unit form for ease of administration and uniformity of dosage.

Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

EXAMPLES

Example 1

Generation of VHZ-EGFP, VHZ (C95S)-EGFP, VHZ-GST, and VHZ(C95S)-GST Expression Constructs The human Universal Quick-clone II cDNA library (BD, Cat#637260) is used as template in the generation of VHZ fragment. Forward primer A; 5' gcgaattcaccatgggcgtgcagcccccaacttctcc3' (SEQ ID NO: 6) and reverse primer B; 5' gtggatcccgtttcgttcgctggtag 3' (SEQ ID NO: 7) are used to perform PCR (94, 55, 72° C., 40 cycles). The VHZ PCR fragment is then inserted into the EcoR1 and BamH1 sites of the pEGFP-N1 vector, resulting in VHZ C-terminally tagged with EGFP (VHZ-EGFP). To construct VHZ (C95S), the above forward primer A and reverse primer B together with a mid-reverse primer 5' gccaaagcccagagcagagtgcactc-ccacagc3' (SEQ ID NO: 8) and a mid-forward primer 5' gcgaattcaccatgggcgtgcagcccccaacttctcc3' (SEQ ID NO: 6) are used in a similar strategy as described previously (Zeng et al. 2003) to make catalytically inactive VHZ (C95S). The VHZ (C95S) PCR fragment is then inserted into the EcoR1 and BamH1 sites of the pEGFP-N1 vector to form mutant VHZ C-terminally tagged with EGFP; VHZ-(C95S)-EGFP. The VHZ and VHZ(C95S)PCR products are respectively inserted into pGEX-KG to form VHZ-GST and VHZ (C95S)-GST. All clones are confirmed by DNA sequencing of the coding region.

Example 2

Generation of MCF-7 and NRK Cell Pools Stably Expressing VHZ-EGFP, VHZ-EGFP(C95S) and EGFP Vector Alone The three expression constructs are respectively transfected into the human breast cancer cell line-MCF-7 (ATCC HTB-22) or Normal Rat Kidney cell-NRK (ATCC CRL-6509), using Lipofectamine 2000 (Invitrogen). The cells are cultured in RPMI 1640 medium supplemented with 10% fetal bovine serum and 2 mM L-glutamine (Invitrogen). Cells are selected in 1 mg/ml G418 for 20-30 days to establish stable cell pools. The stable pools ($10^6$ cells/ml) are then subjected to EGFP sorting by FACS Vantage, SE mode (Becton Dickinson) to select for EGFP-positive cells.

Example 3

Confocal Microscopy and Analysis of VHZ-EGFP Subcellular Localization

NRK cells transfected with VHZ-EGFP expressing vector are grown on coverslips and washed once with PBSCM (PBS containing 1 mM $MgCl_2$ and 1 mM $CaCl_2$). Cells are then fixed in 2.7% paraformaldehyde for 20 min at room temperature (RT, 24° C.). After two more washes with PBSCM, the cells are permeabilized for 15 min with 0.12% Saponin in PBSCM and incubated with rabbit anti-Pericentrin antibody from Covance' Inc (Princeton, N.J.) for 1 hour at RT, and then overnight at 4° C. The cells are gently washed three times with PBSCM and incubated with anti-mouse IgG conjugated with Texas Red (Sigma) for 4 hours at RT. The VHZ-EGFP is directly visualized (green) by fluorescence microscopy. Confocal imaging is performed (Zeiss LSM 510 Image Browser).

Example 4

Generation of Mouse Monoclonal and Rabbit Polyclonal Anti-VHZ Antibodies

Figure 9A:
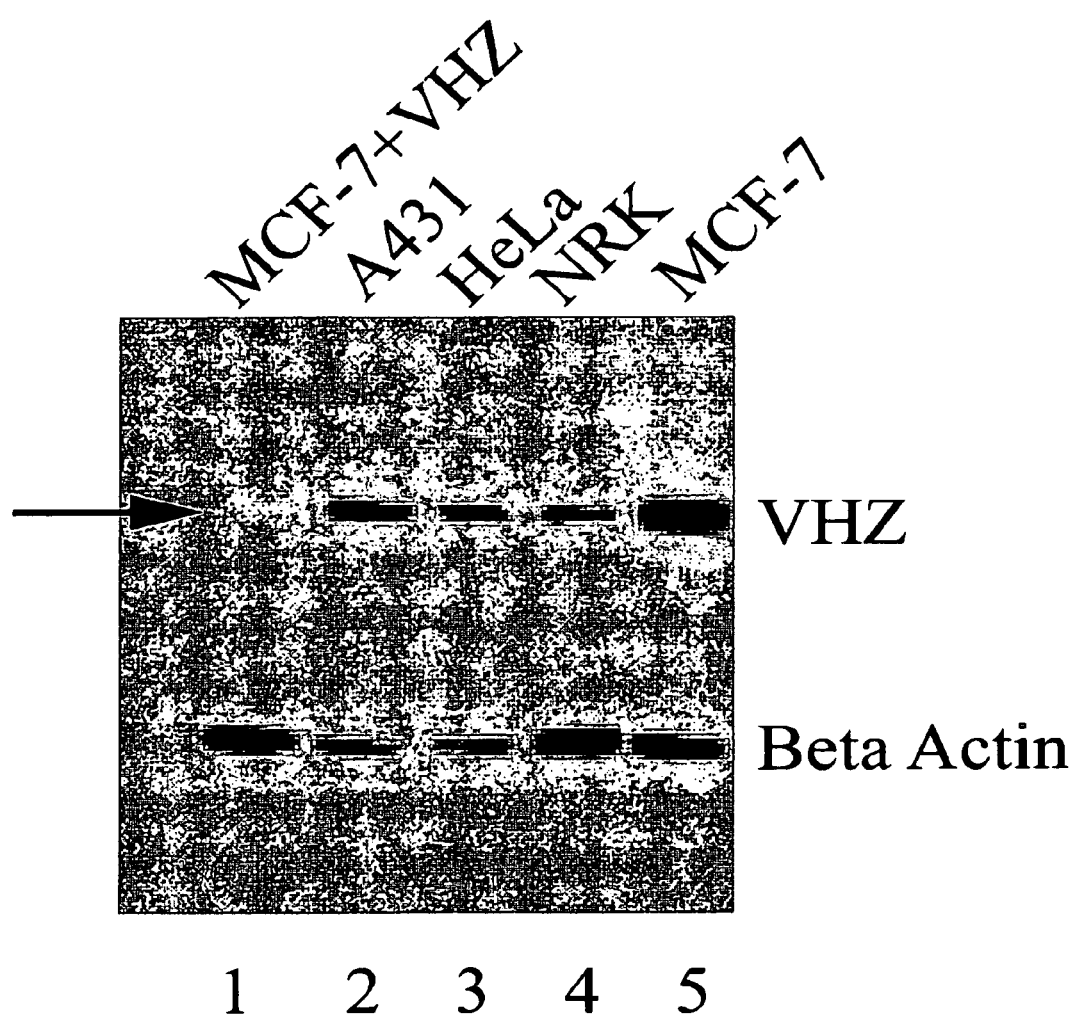
FIG. 9A and FIG. 9B are figures showing characterization of rabbit and mouse anti-VHZ antibodies FIG. 9A. Western blots analysis with rabbit and mouse anti-VHZ antibodies. Total cell lysates are derived from A431, HaLa, NRK, and MCF-7 cells. MCF-7 total cell lysate is pre-incubated with 2 μg VHZ-GST (lane 1). The detection of VHZ band is specifically blocked by VHZ-GST (arrow indicated)
Figure 9A:
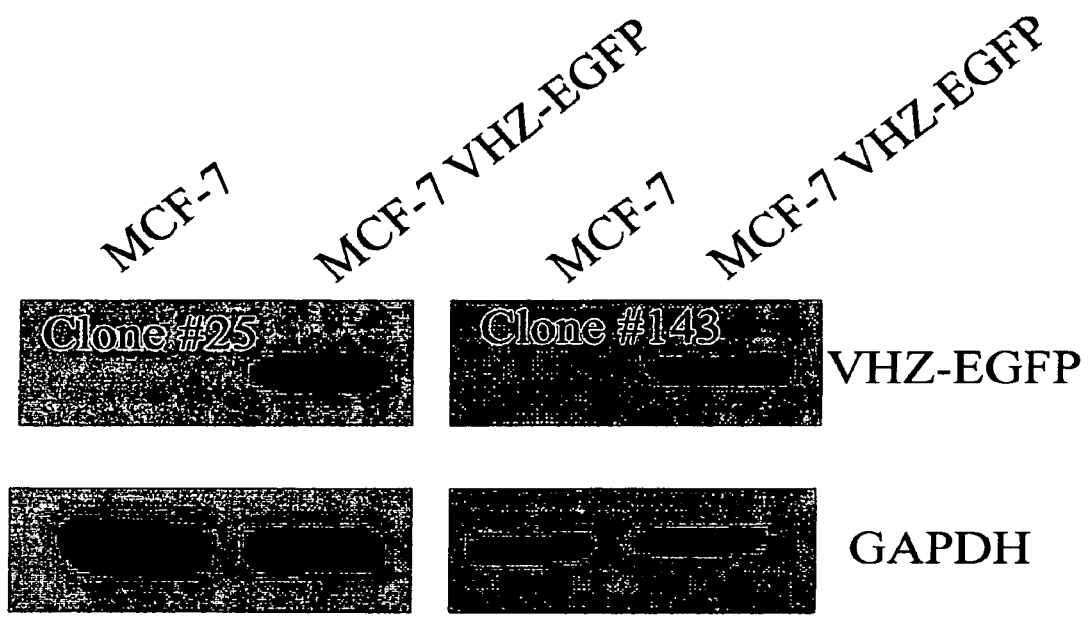
Figure 9B:
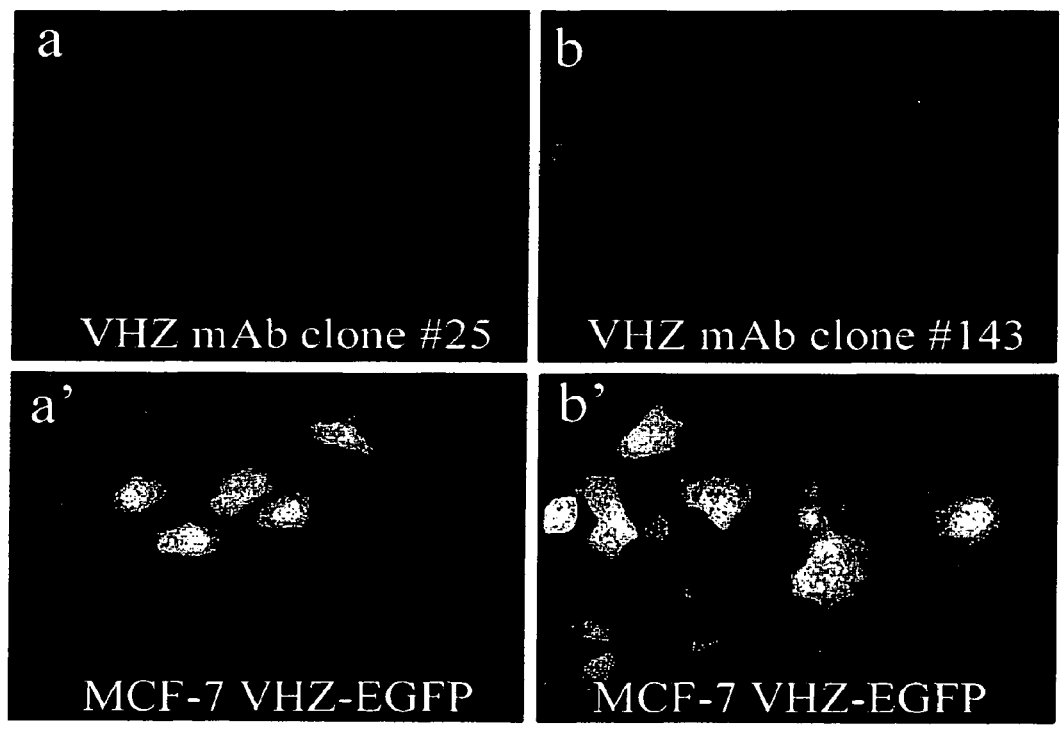

The method is previously described (Li et at., 2005). We used the ClonaCell™-HY Hybridoma Cloning Kit (Stemcell Technologies Inc.) to generate VHZ hybridomas. After fusing spleenocytes, derived from mice immunized with VHZ-GST, with SP2/0 myeloma cells, 506 surviving hybridoma clones are isolated and grown up. All clones are initially tested for VHZ binding by ELISA. 80 clones showed good reaction with VHZ, and the two specific VHZ clones with strongest reactivity are selected as these two clones can be used in several applications (FIGS. 9A-9B). Rabbit polyclonal anti-VHZ serum is generated (Genemed Synthesis, Inc.). The antibodies are produced by immunizing rabbits with a synthetic peptide C-RRLRPGSIETYEQEK (SEQ ID NO: 9) corresponding to amino acid residues (126-140) of human VHZ. Antibodies are purified by protein A and then peptide affinity chromatography. A specific band of expected size (16 kDa) is detected by this antibody in immunoblot analysis of cell lysates derived from several cell lines, and detection of this band is specifically blocked by VHZ-GST fusion protein (FIG. 9A).

Example 5

Confocal Microscopy and Analysis of Endogenous VHZ in NRK, MCF-10A, And A431 Cells NRK cells, Human Mammary Epithelia cell-MCF-10A (ATCC CRL-10317), and Human Epithelial carcinoma cell-A431 (ATCC CRL-1555) are grown on coverslips and washed once with PBSCM (PBS containing 1 mM $MgCl_2$ and 1 mM $CaCl_2$). Cells are then fixed in 100% methanol for 15 min at −20° C. After two more washes with PBSCM, the cells are permeabilized for 15 min with 0.12% Saponin in PBSCM and incubated with mouse anti-γ-tubulin (Sigma) and rabbit anti-VHZ antibodies (1:150 dilution) for 1 hour at RT, and then overnight at 4° C. The cells are gently washed three times with PBSCM and incubated with anti-mouse IgG conjugated with Texas Red (Sigma) and anti-rabbit IgG conjugated with FITC (Sigma) for 4 hours at RT. Confocal imaging is performed (Zeiss LSM 510 Image Browser).

Example 6

Tyrosine Phosphatase Assay

The EnzChek kit (Invitrogen, R22065) is used. As per the manufacturer's protocol, the fluorogenic substrate is reconstituted in the assay wells with buffer; the desired potential PTPases (0.675 picomole for each protein: VHZ-GST, VHZ-GST+Phosphatase inhibitor, VHZ(C95S)-GST, and control GST) are added to the wells and incubated 30 min or 90 min respectively. The fluorescence is then quantified using a Gemini XPS microplate spectrofluorometer (Molecular Devices). Fluorescence is measured at 10 minute intervals at the excitation and emission wavelengths of 358 and 452 nm, respectively. The phosphatase inhibitor sodium orthovanadate (10 μM) is used in the assay as a negative control.

Example 7

Measuring Newly Synthesized DNA by BrdU Labeling

Cell proliferation is assessed by measuring newly synthesized DNA using APC BrdU Flow Kit (BD Pharmingen) according to the manufacturer's protocol. The FACS data are analyzed using WinMDI 2.8 software. The percentage of APC-labeled cells (FL2) is determined.

Example 8

Western Blot Analysis

Detailed steps were as previously described (Li et al., 2005). Rabbit anti-VHZ antibody is used at a dilution of 1:500. Phospho-Rb (Ser 780), Phospho-Rb (Ser795), Phospho-Rb (Ser807/811), and -actin antibodies were from Cell Signaling Technology (Beverly, Mass.). GAPDH antibody is from Santa Cruz Biotechnology (Santa Cruz).

Example 9

Immunohistochemistry (IHC)

We investigated VHZ protein expression on human breast cancer specimens. With VECTASTAIN ABC kit (Orton Southgate, Peterborough, England), rabbit anti-VHZ antibody (1:300 dilution) is used to perform IHC experiments. A total of 65 formalin-fixed and paraffin-embedded surgical specimens of primary human breast cancer samples are collected from the archives of the pathology department of the Henan Medical Hospital. In addition, human breast carcinoma tissue arrays TMA (CC08-11-008) is purchased from Cybrdi (Frederick) to reconfirm the results. The IHC method is previously described (Li et al., 2005). E-cadherin antibody is purchased (Cell Signaling Technology).

Example 10

MCF-7-VHZ-EGFP and MCF-7-VHZ(C95S)-EGFP Cell Motility

We assessed as previously described (Sherri et al., 2006). By plating cells in a confluent monolayer on a coverslip (12 mm), the cell-coated coverslip is then inverted with cell side down to a fresh culture dish (35 mm). Fresh culture medium (2 ml RPMI with 10% FBS) is gently added into the dish. Images are taken at 0- and 48-hours.

Example 11

Establishment of MCF-10A Stable Pools Expressing VHZ-EGFP and VHZ(C95S)-EGFP by Retrovirus Generation and Infection VHZ and VHZ(C95S)PCR fragments are respectively cloned into EcoR1 and BamH1 enzyme sites of the retroviral vector (pBABEpuro). The amphotropic Phoenix packaging cells are transfected with pBABEpuro-VHZ or pBABEpuro-VHZ(C95S) retroviral vectors respectively, using Lipofectamine according to manufacturer's instruction (Invitrogen). After 48 h, the retroviral supernatants are collected, filtered (0.45 μm; Millipore) and added onto the target MCF10A cells in the presence of 5 μg/ml of polybrene (Sigma-Aldrich) for 6-8 h. Infection is done twice. After infection, the cells are selected with puromycin (1 μg/ml) for a week before being analyzed.

Example 12

MCF-10A-VHZ-EGFP and MCF-10A-VHZ(C95S)-EGFP Cell Motility in Wound-Healing assays Assays are performed on monolayer of the cells by creating wounds with yellow pipette tips. After washing with PBS, the cells are continuity incubated in fresh culture media. The wounded areas are photographed at the beginning (0 hr, upper panels) and at the end (8 hr, lower panels) of the assay.

Example 13

Exogenous VHZ Localizes in the Centrosome and Throughout the Cytoplasm

Determining the intracellular localization of a protein can sometimes provide clues as to the possible biological function(s) of the protein.

Figure 1B:
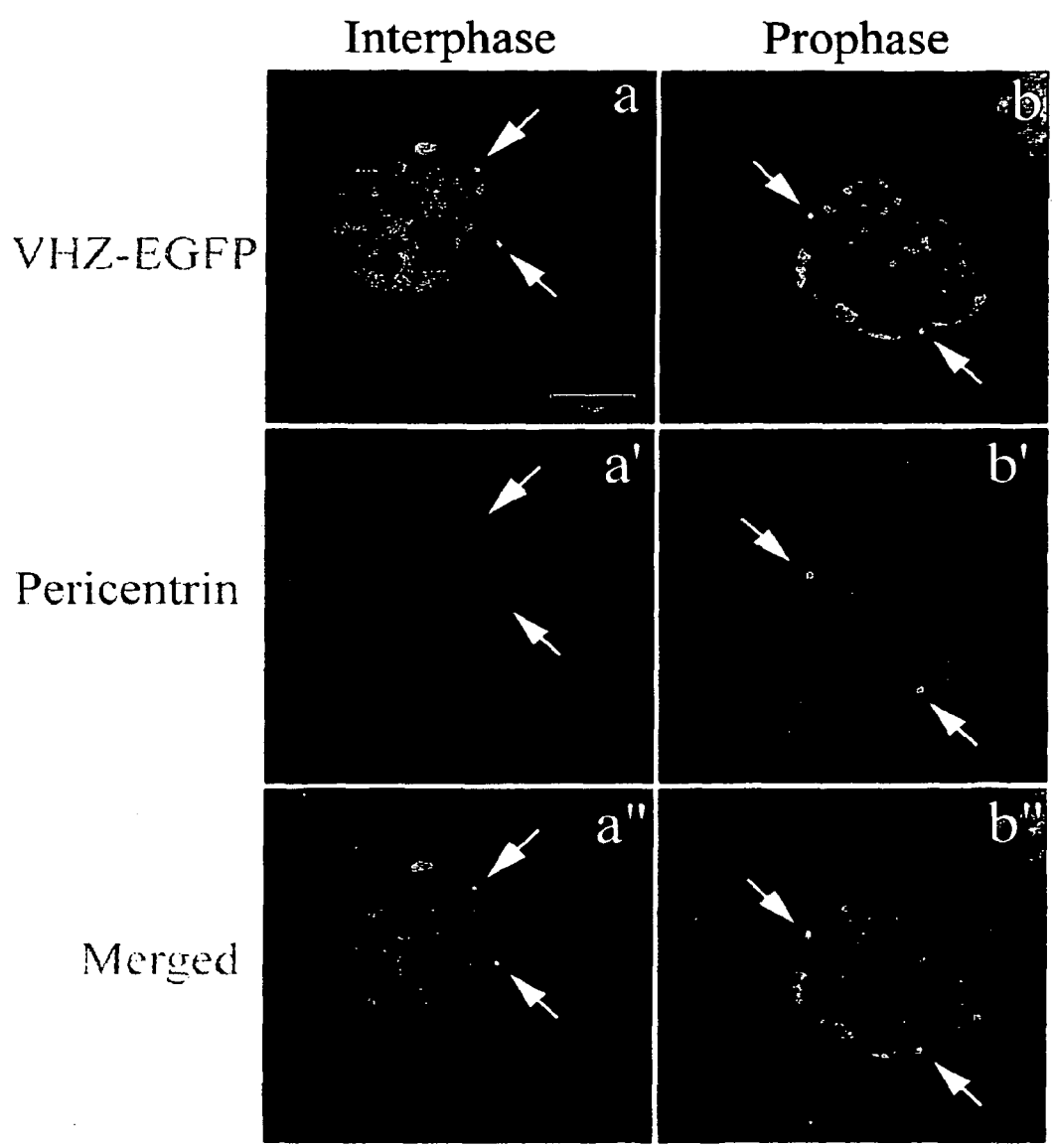
Figure 1B:
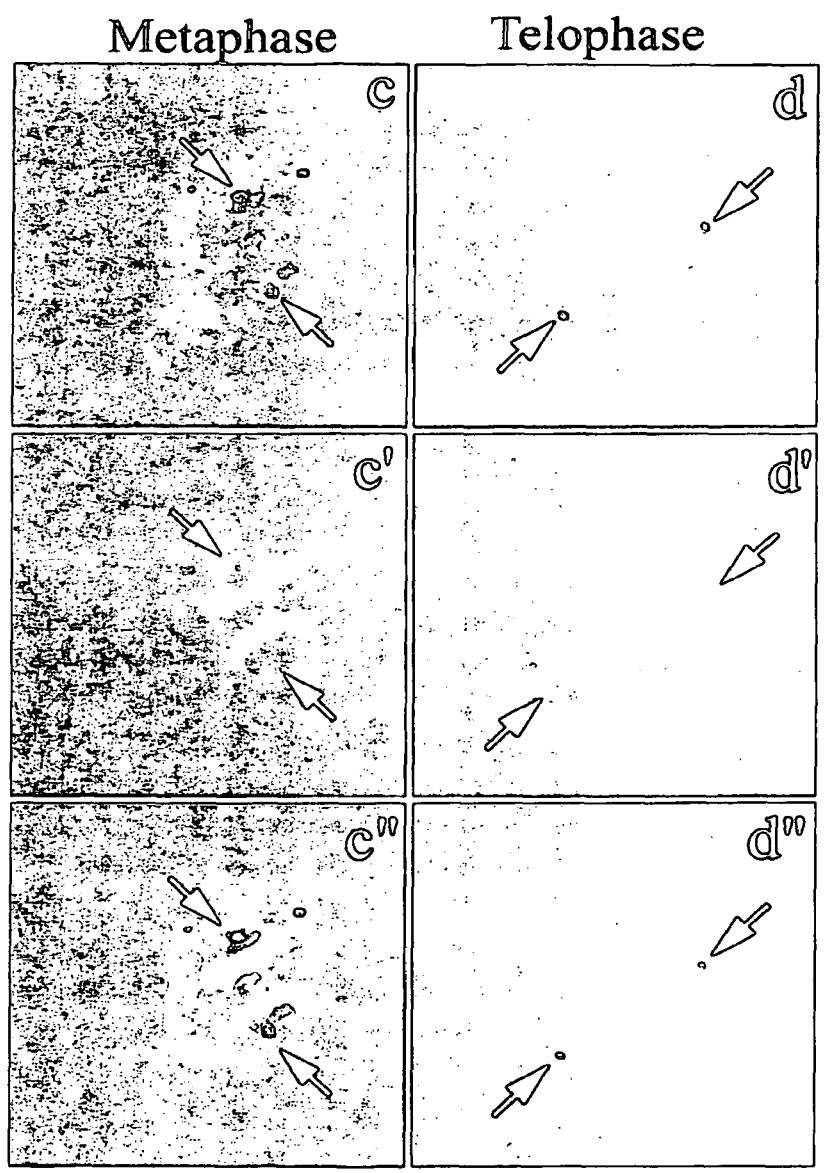

To assess the subcellular localization of VHZ, we generate NRK cells that stably express VHZ-EGFP. Confocal microscopy of these cells shows that VHZ has a range of subcellular locations. The EGFP signal is found at the plasma membrane and the cytoplasm (FIG. 1A). Importantly, enrichment of EGFP-tagged VHZ in the centrosome is apparent in all stages of the cell cycle, as it co-localizes with the centrosomal marker-pericentrin (FIG. 1B).

Endogenous VHZ localizes in the centrosome and the cytoplasm. The EGFP-tagged VHZ protein provides useful information regarding its subcellular localization. To understand the causal nature of VHZ, it is essential to examine the subcellular distribution of the endogenous VHZ protein.

Figure 2A:
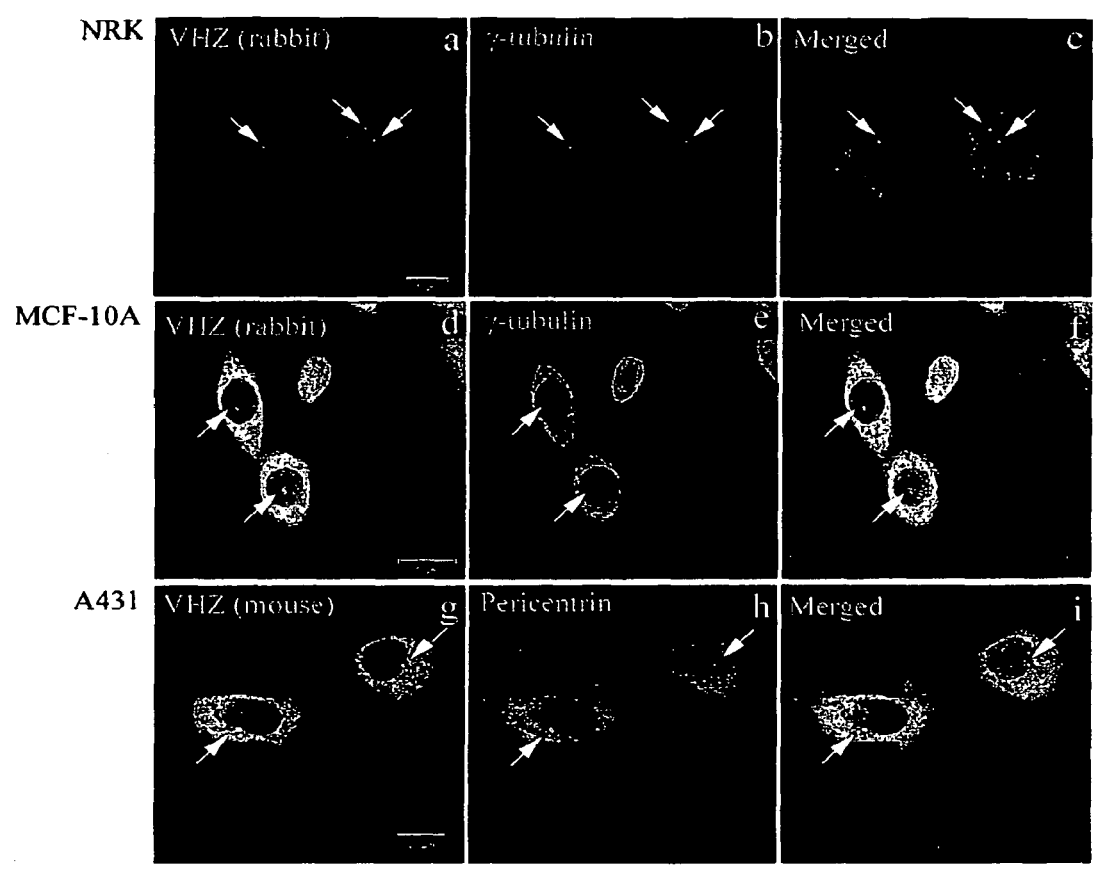
FIG. 2A and FIG. 2B are figures showing that endogenous VHZ localizes in the centrosome and the cytoplasm.

Using double immunofluorescence labeling with affinity-purified rabbit polyclonal anti-VHZ antibody in conjunction with mouse monoclonal (mAb) anti-γ-tubulin (another centrosomal marker) antibody, endogenous VHZ is clearly seen in the centrosome co-localized with γ-tubulin in NRK cells (FIG. 2A, Panels A-C), and in MCF-10A cells (FIG. 2A, Panels D-F). In addition, anti-VHZ mAb together with rabbit polyclonal anti-pericentrin antibody shows again that endogenous VHZ is co-localized to the centrosome in A431 cells (FIG. 2A, Panels G-I).

Figure 2B:
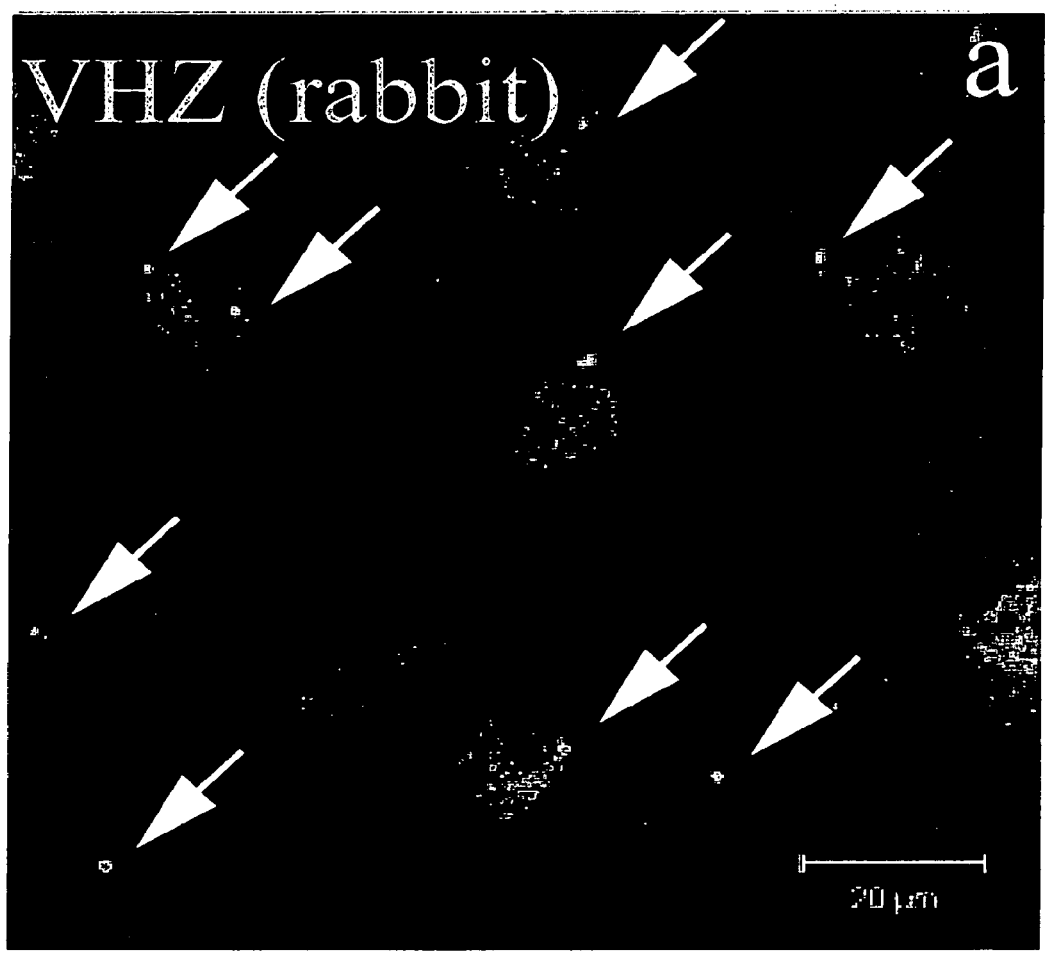
Figure 2B:
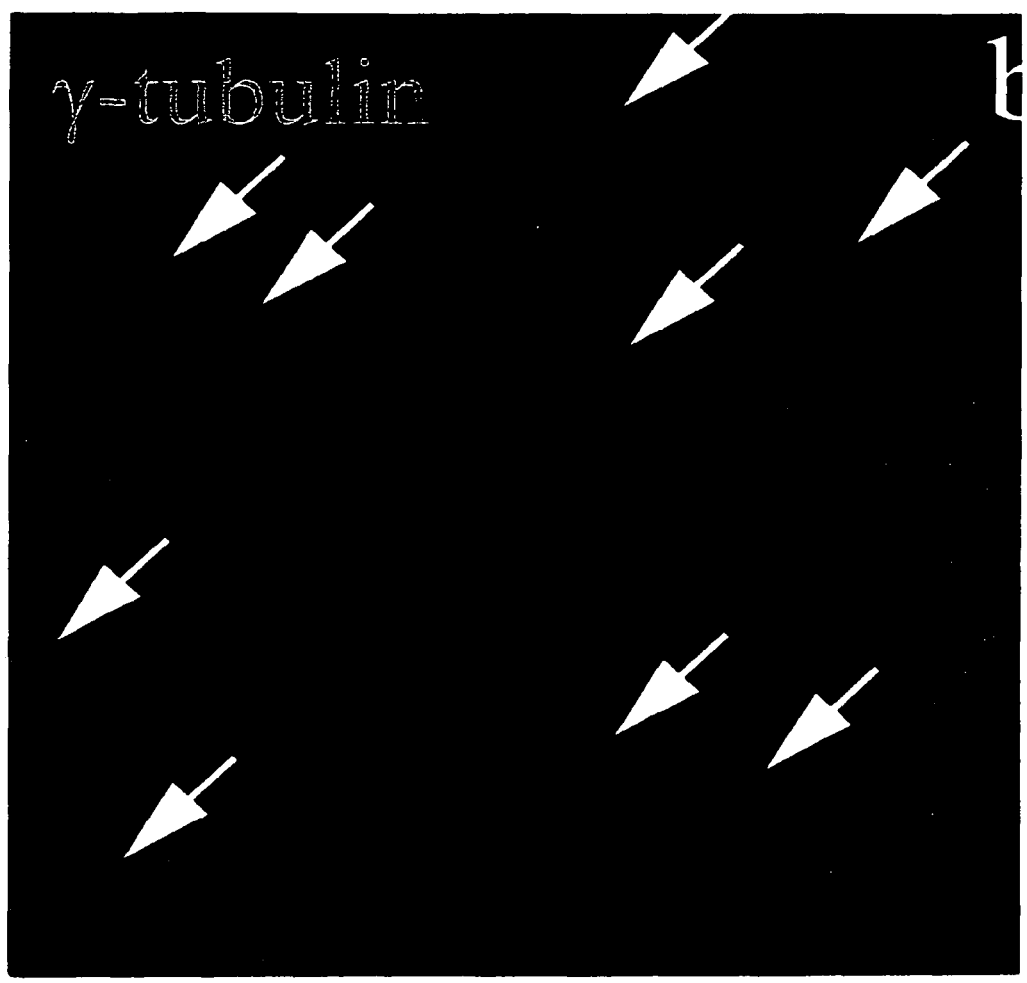
Figure 2B:
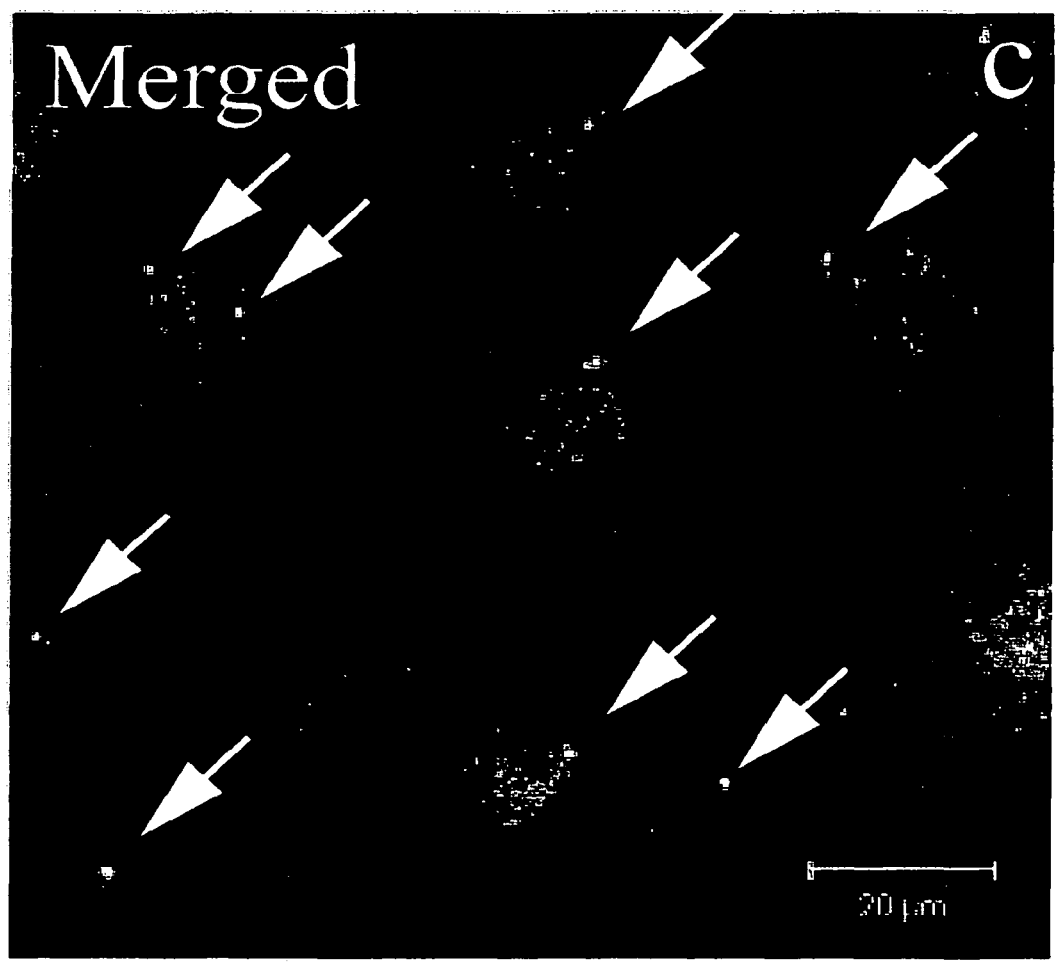

Endogenous VHZ is shifted from cytoplasm to the nucleus with enrichment in the centrosome after serum starvation. NRK cells are serum-starved overnight. Double immunofluorescence labeling with rabbit anti-VHZ antibody and anti-γ-tubulin mAb, endogenous VHZ protein is observed to be more concentrated in the centrosome. Furthermore, a decrease in cytoplasmic distribution with concomitant increase in the nucleus is surprisingly observed in NRK cells (FIG. 2B).

Example 14

VHZ is a Protein Tyrosine Phosphatase

Figure 3A:
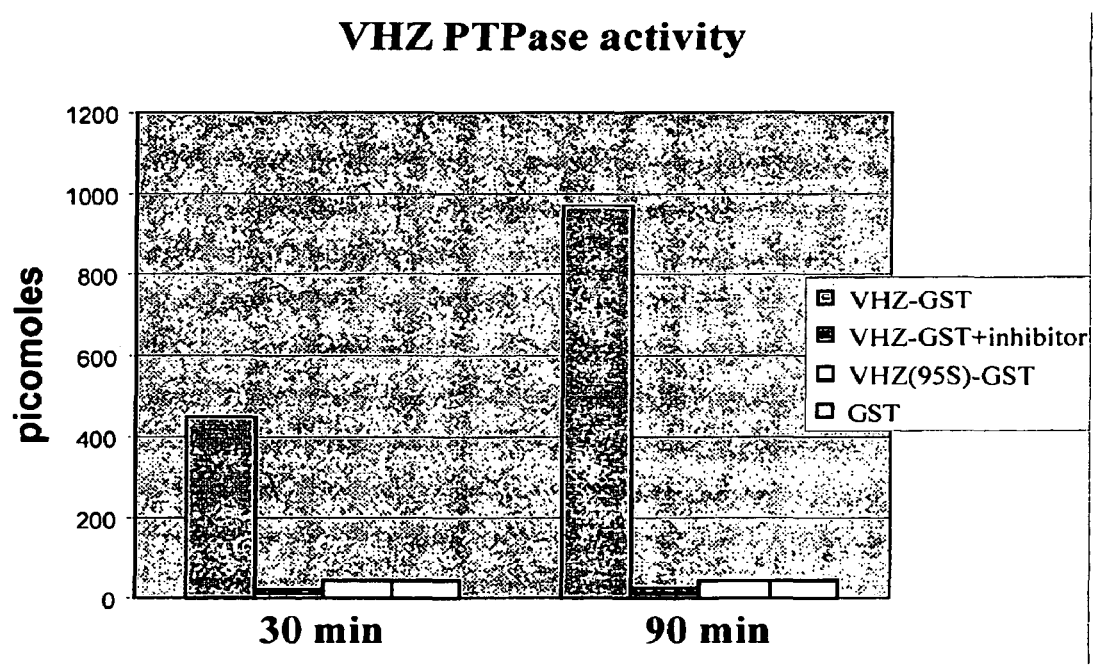
FIG. 3A, FIG. 3B and FIG. 3C are figures showing that VHZ has protein tyrosine phosphatase activity and is involved in cell cycle regulation FIG. 3A. We test each protein (0.675 picomoles) for its PTPase activity. The PTPase activity of VHZ is completely abolished by adding 10 μM sodium orthovanadate (VHZ-GST+Vanadate) in the reaction or by point mutation of Cys 95 to Ser [VHZ (C95S)-GST)]

To verify that VHZ is indeed an active tyrosine phosphatase, we assay the PTP activity of VHZ-GST or a catalytically inactive VHZ (C95S)-GST fusion proteins comparing with GST alone as a control protein. The PTPase activities of VHZ-GST, indicated by increasing blue fluorescence (excitation/emission maxima ~358/452 nm), are abolished either by mutation of Cys 95 to Ser or by adding phosphatase inhibitor (sodium orthovanadate) into the assay (FIG. 3A, Panel A).

Example 15

VHZ Enhances Cell Proliferation by Facilitating G1/S Transition

Figure 3B:
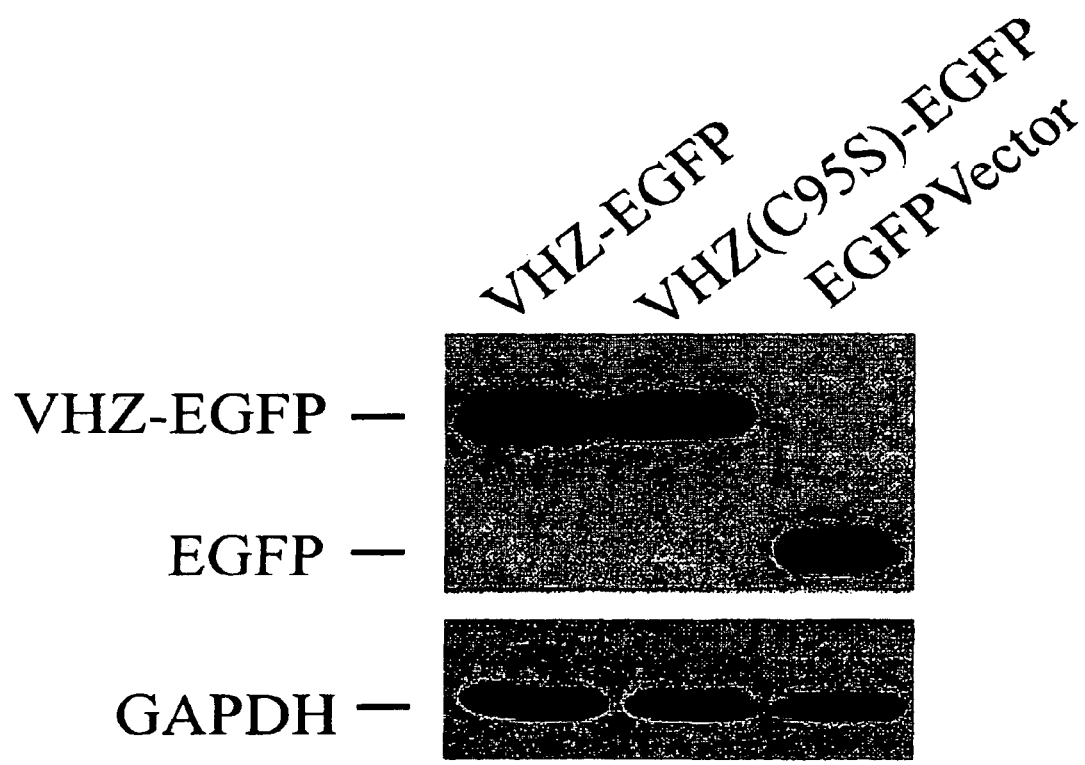
Figure 3B:
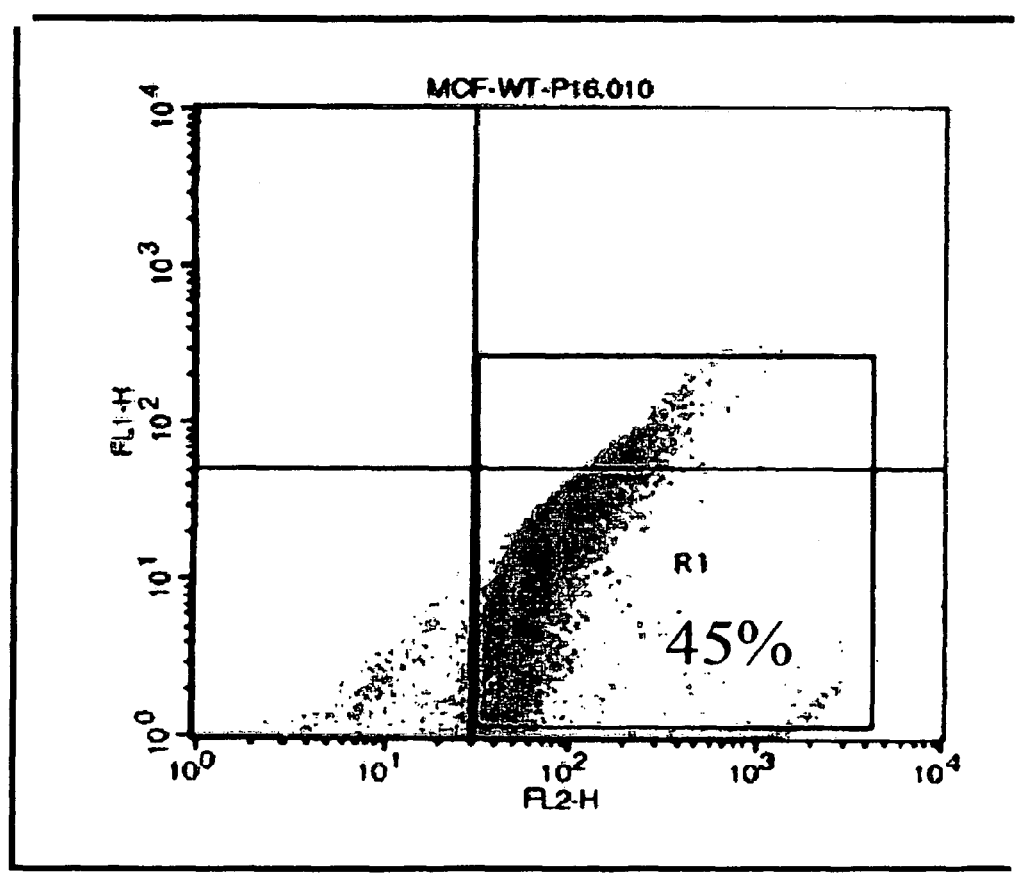
Figure 3B:
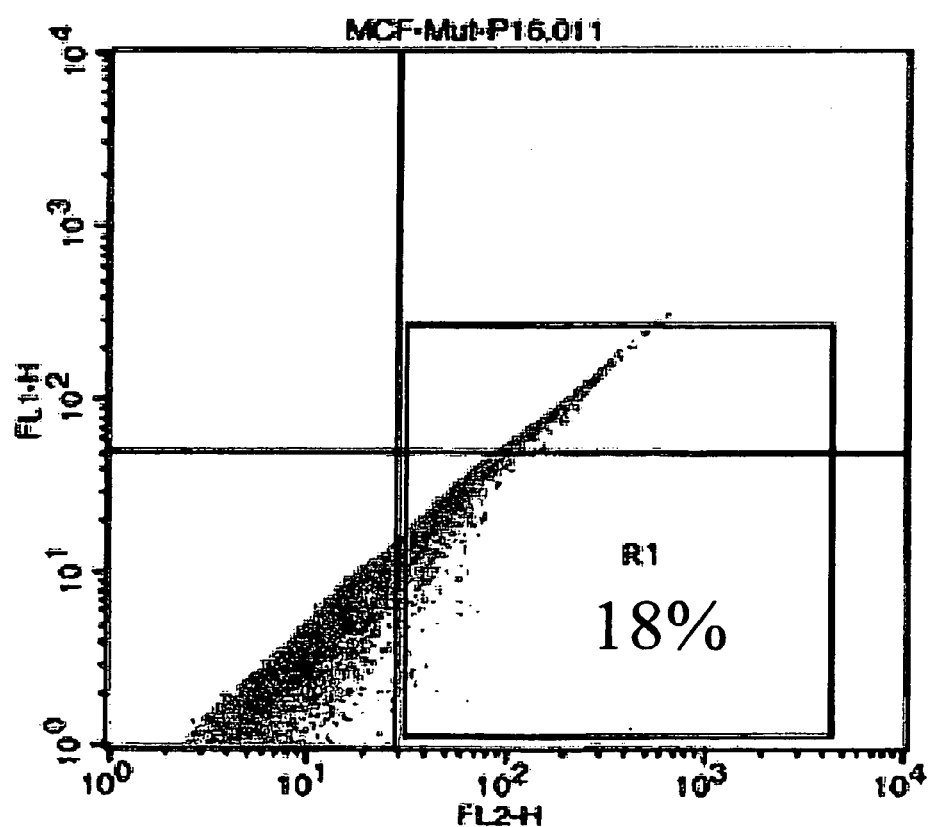
Figure 3B:
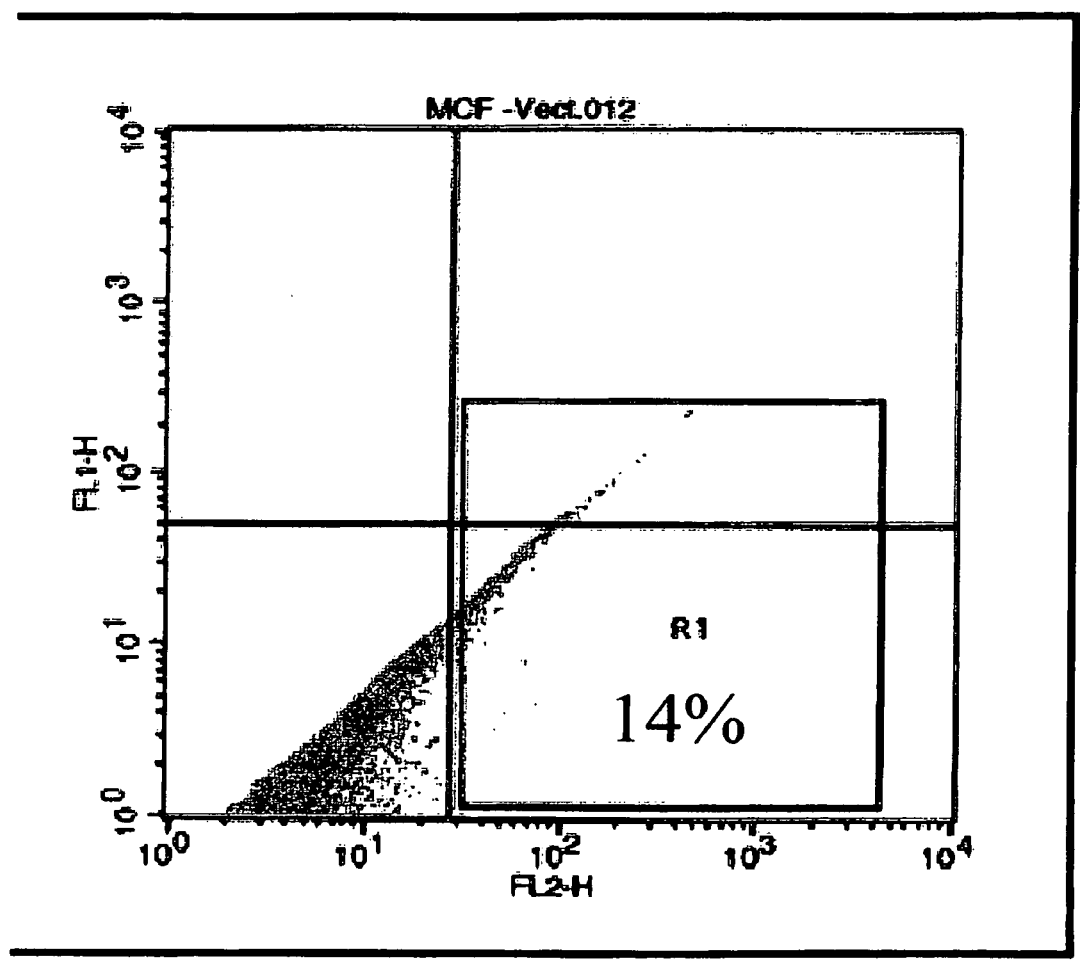
Figure 3C:
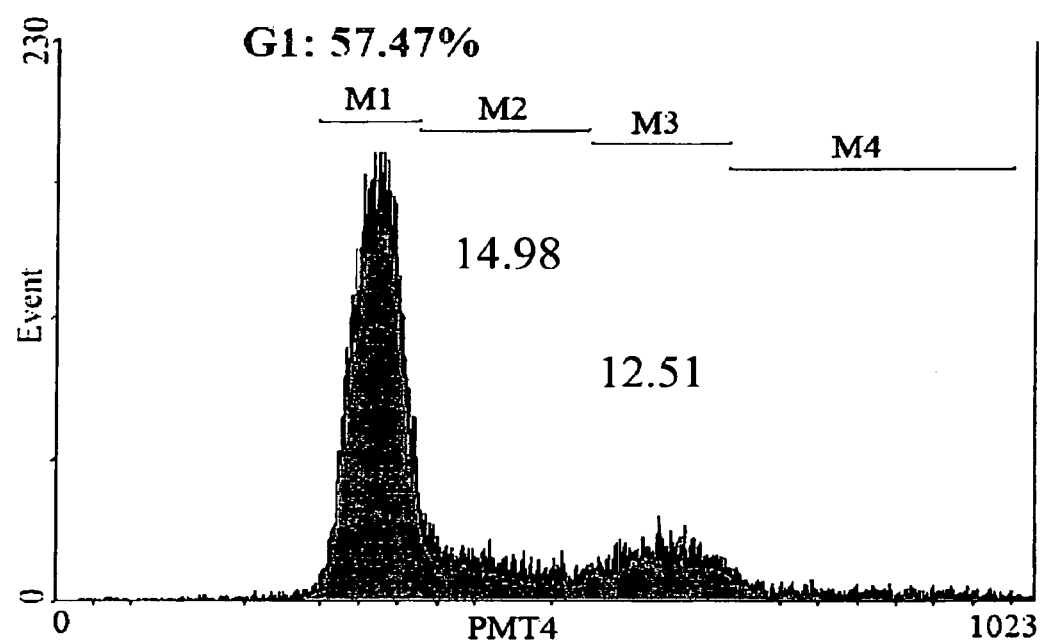
Figure 3C:
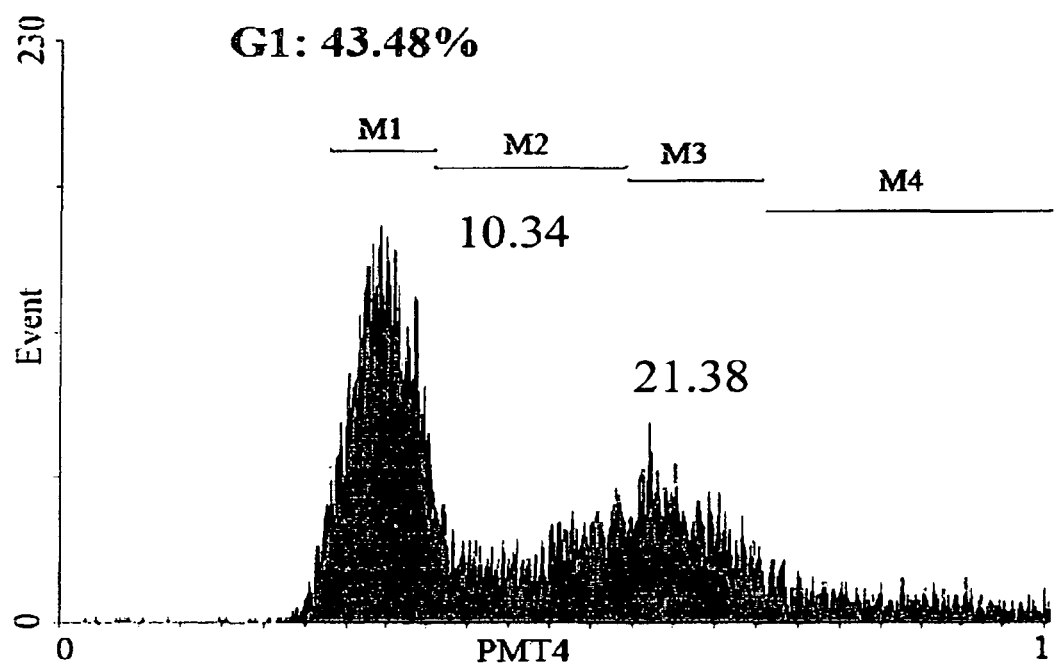
Figure 3C:
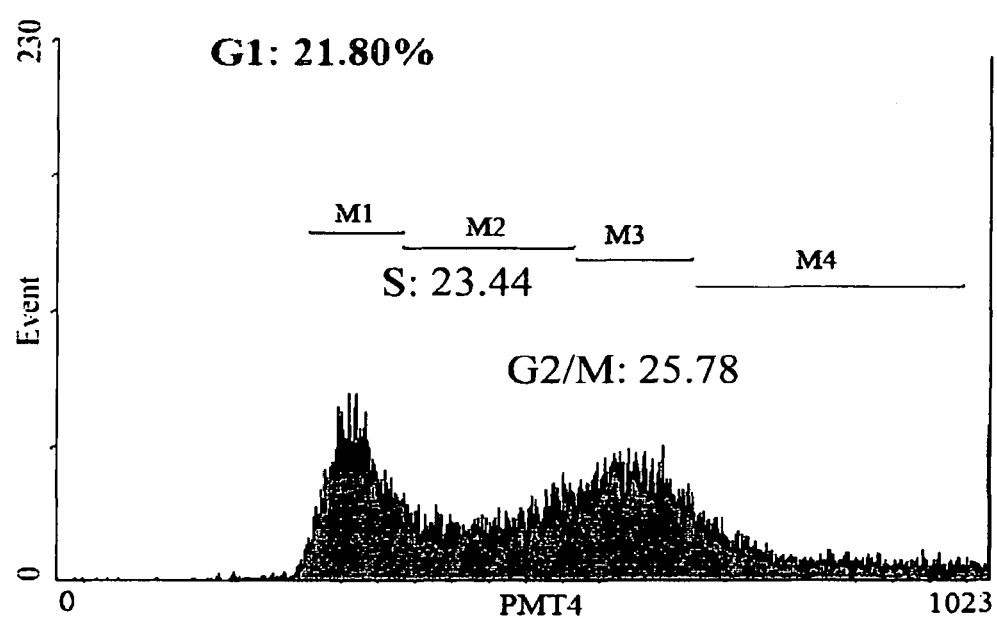

The association of VHZ with the centrosome suggests to us that VHZ might have potential function in controlling the cell cycle regulation. To test this, we generated MCF-7 cells that stably expressed three different expression constructs: 1. VHZ-EGFP; 2. VHZ (C95S)-EGFP; and 3. EGFP vector. The three stable pools are analyzed for their cell proliferation. VHZ is found to be able to enhance cell proliferation rates (data not shown). To confirm this observation, DNA synthesis rate is measured in these three cell lines using APC-BrdU incorporation into newly synthesized DNA. The experiment showed that BrdU incorporation is notably higher in cells that expressed VHZ-EGFP than VHZ(C95S)-EGFP or EGFP vector alone (FIG. 3B). Analogous results are also obtained from FACS analyses of NRK cells that stably expressed the same three expression constructs and implicated that VHZ could accelerate G/S transition by reducing G1 but increasing S populations (FIG. 3C). This raised the possibility that wild type VHZ might have a role in G1/S phase progression.

Example 16

VHZ could Indirectly Cause Hyperphosphorylation of Retinoblastoma Protein (Rb)

Figure 4A:
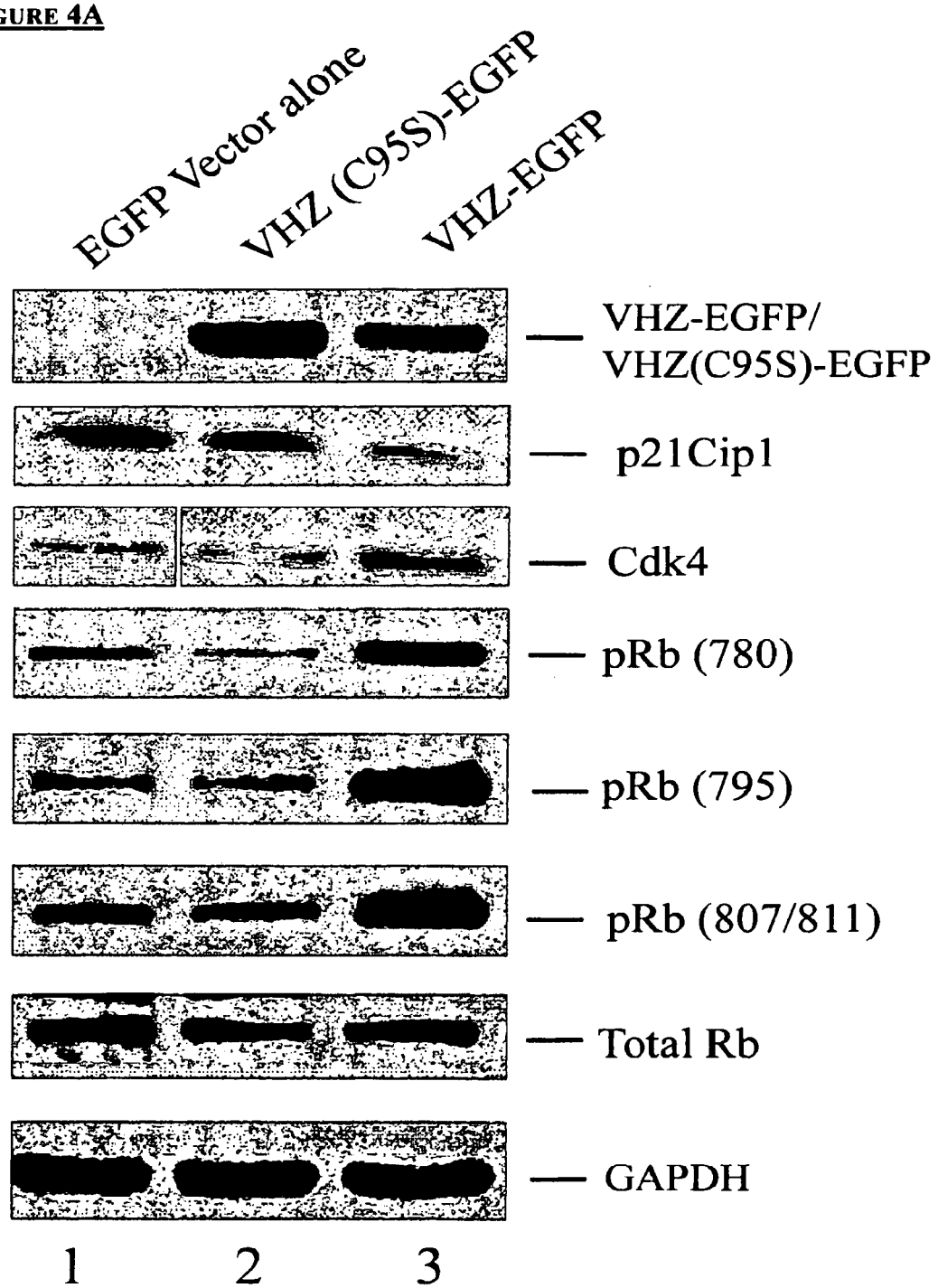
FIG. 4A and FIG. 4B are figures showing that VHZ enhances G1/S transition in MCF-7 cells FIG. 4A. MCF-7 cells expressing EGFP vector, VHZ (C95S)-EGFP or VHZ-EGFP are analyzed for several molecules that are involved in G1/S cell cycle control. There are p21 Waf1/Cip1, Cdk4, and Rb phosphorylated at Ser780, Ser795 and Ser807/811.

To understand how VHZ could facilitate G1/S phase transition and to address the possible molecular mechanism, we carried out immunoblot studies on several major molecules which are important in regulating cell cycle progression from G1 to S phase. We found that VHZ could downregulate the tumor suppressor protein p21 Waf1/Cip1 and upregulate cyclin-dependent kinase (Cdk)4. Cdk4 is one of the major players governing G1 to S phase progression and could phosphorylates the retinoblastoma protein pRB (Sherr and Roberts, 1999). Consistent with this, we showed that overexpression of VHZ phosphatase could indirectly lead to an accumulation of phosphrylation of Rb at residues Ser780, Ser795, and Ser807/811 as assessed by phospho-specific antibodies (FIG. 4A, Lane 3).

Example 17

Figure 5A:
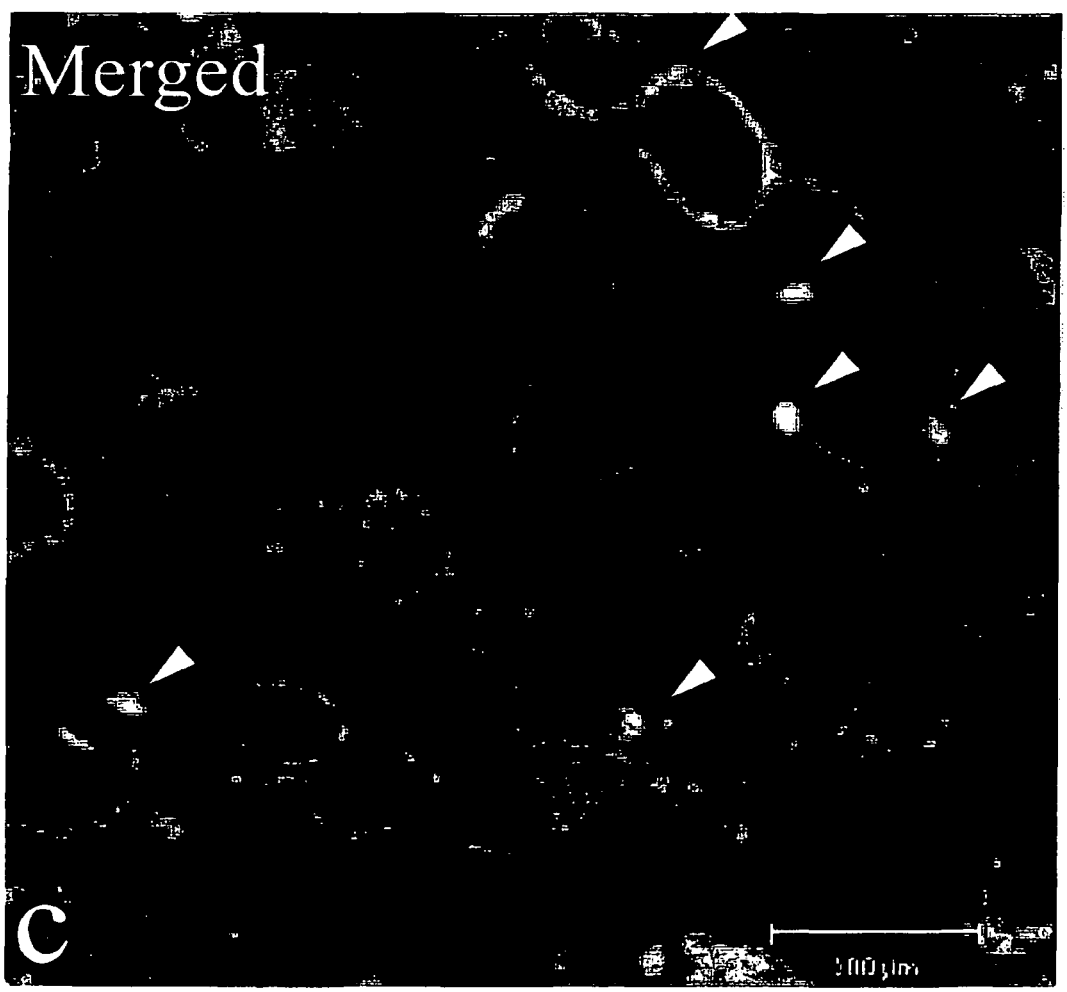
FIG. 5A, FIG. 5B and FIG. 5C are figures showing that overexpressed VHZ protein is distributed in the centrosome or in the cytoplasm of epithelial tumor cells in some breast cancer samples. Formalin-fixed and paraffin-embedded breast cancer samples are assessed for VHZ protein expression.
Figure 5A:
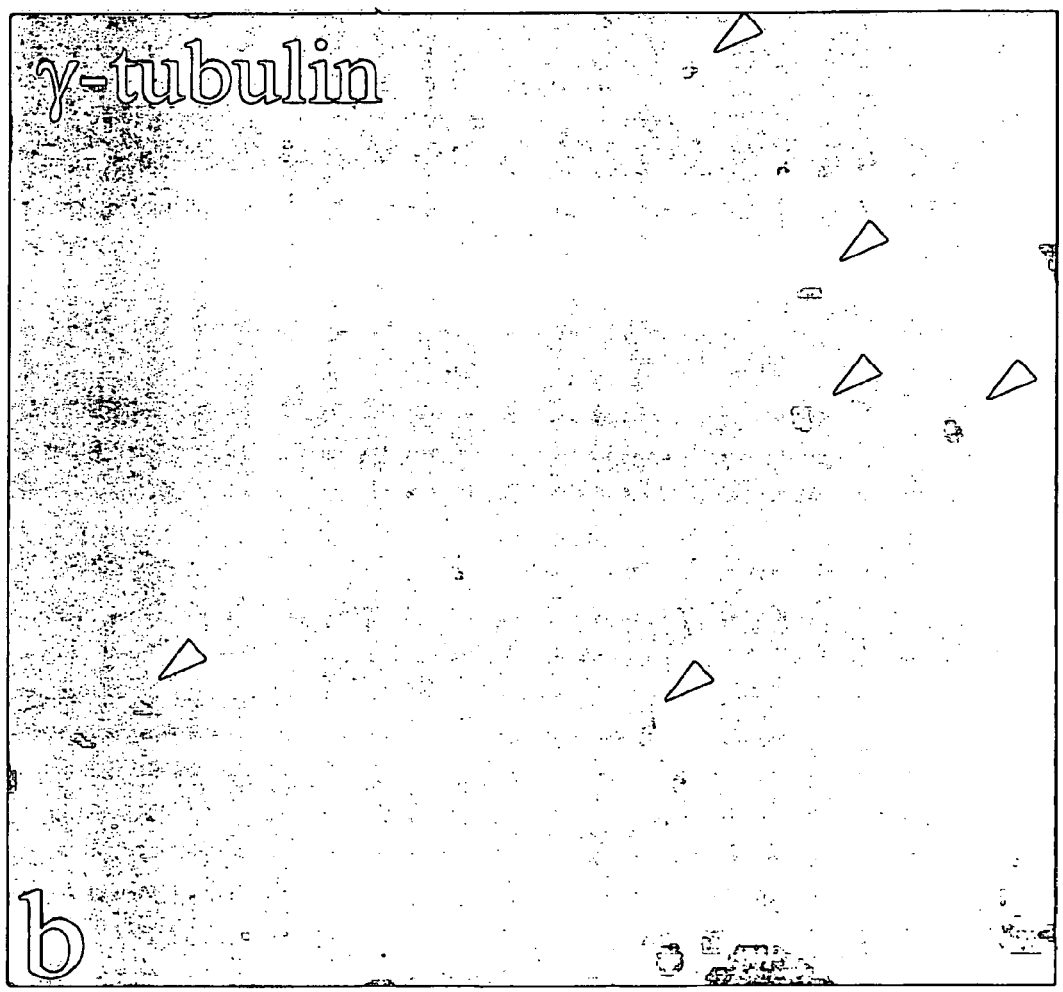
Figure 5A:
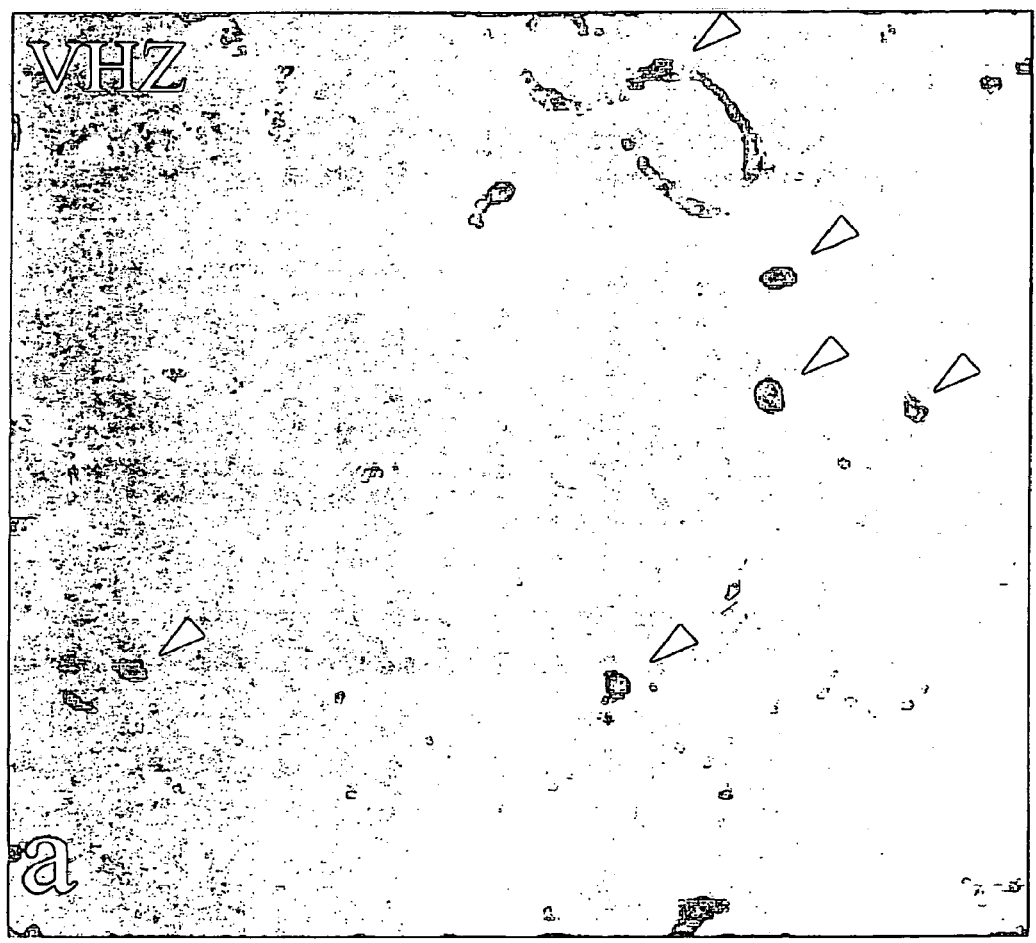
Figure 5B:
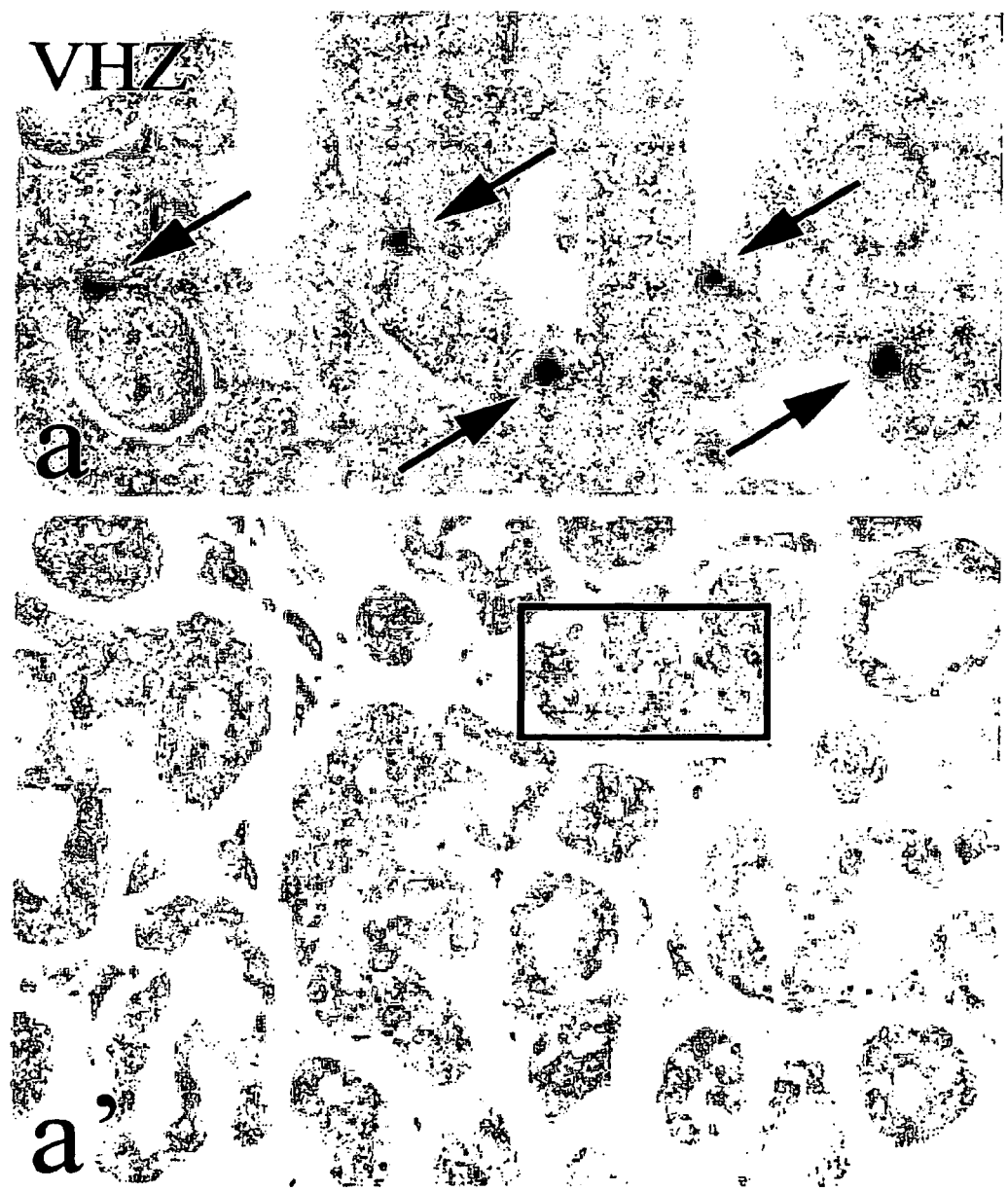
Figure 5B:
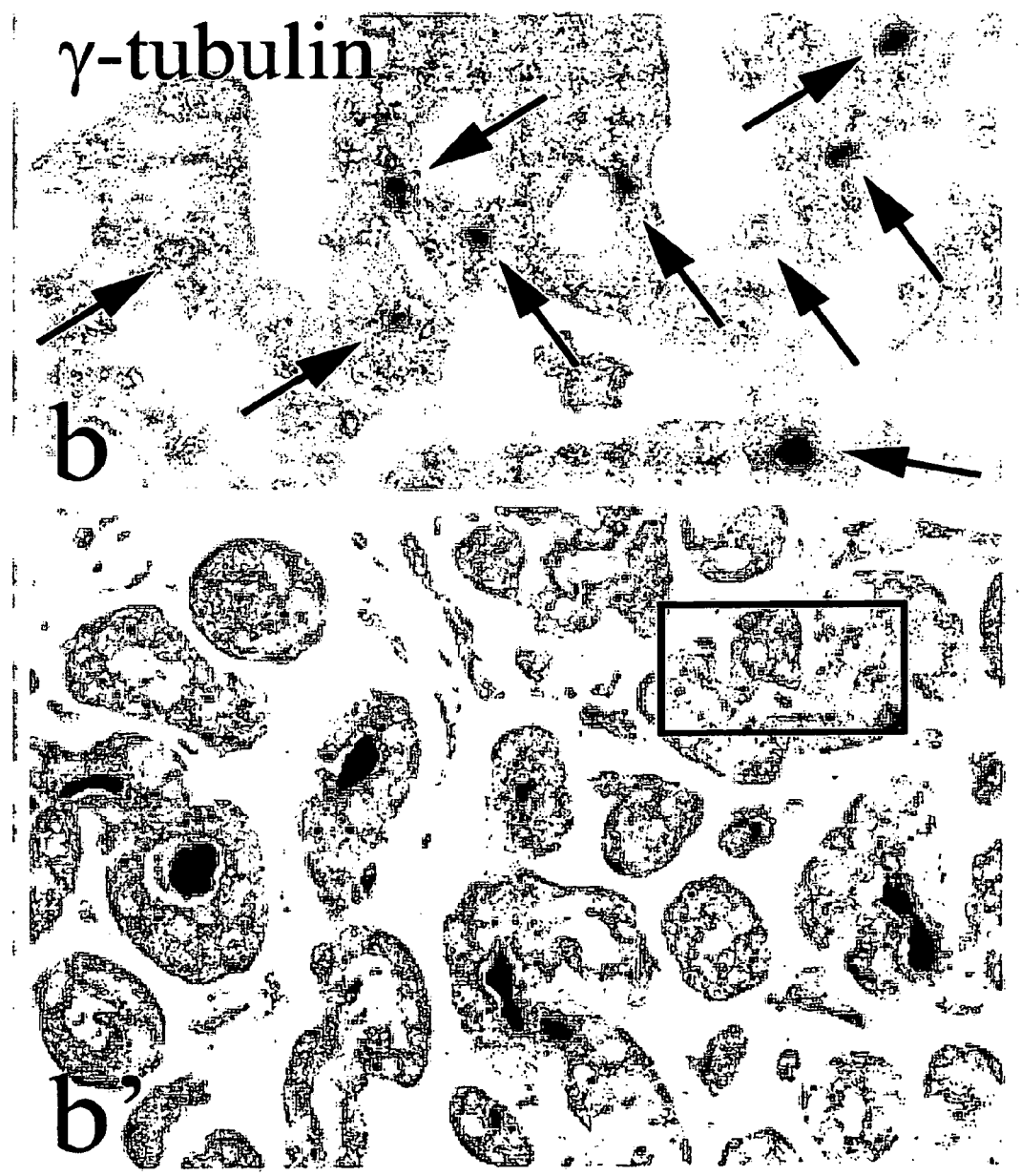
Figure 5B:
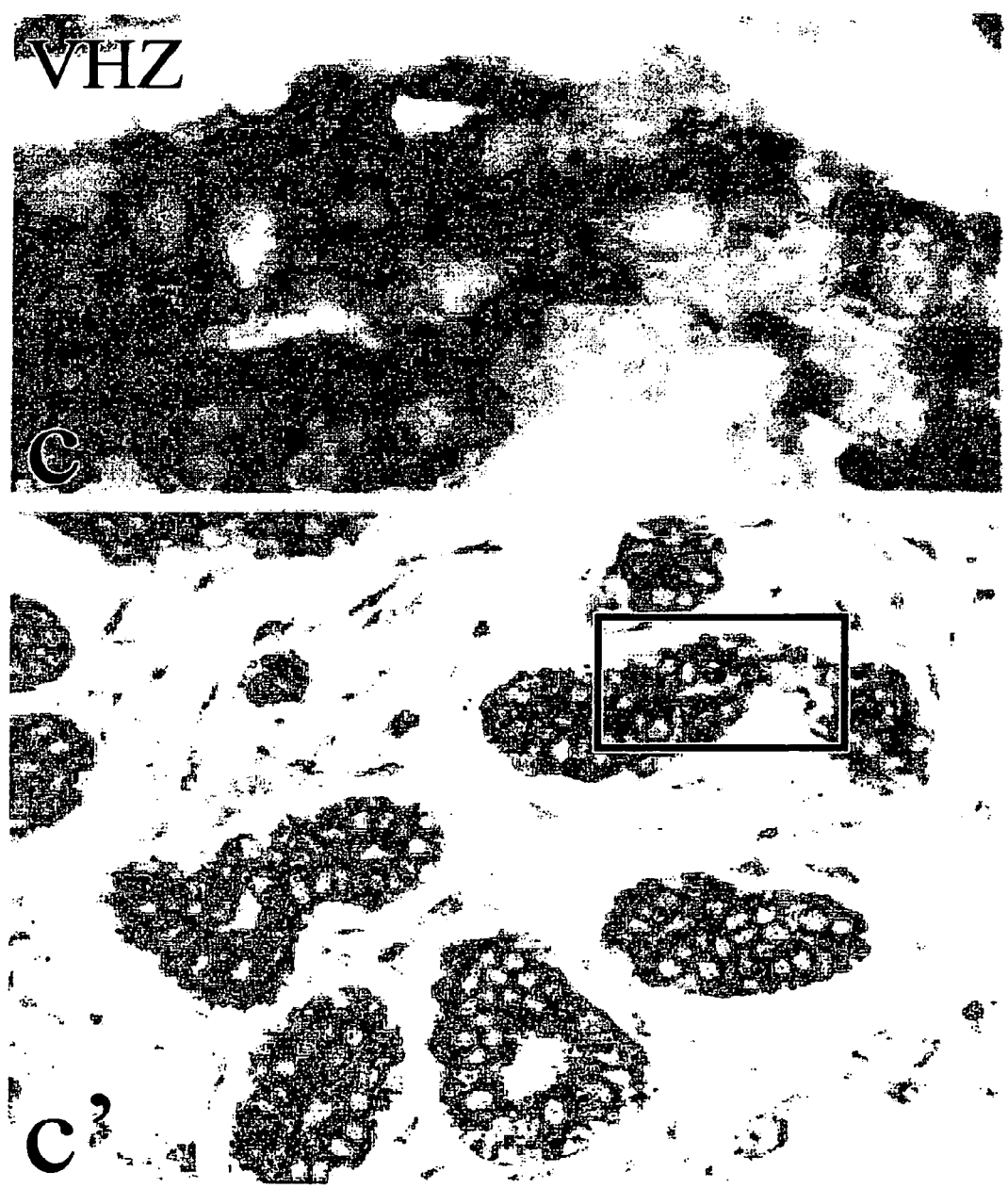
Figure 5C:
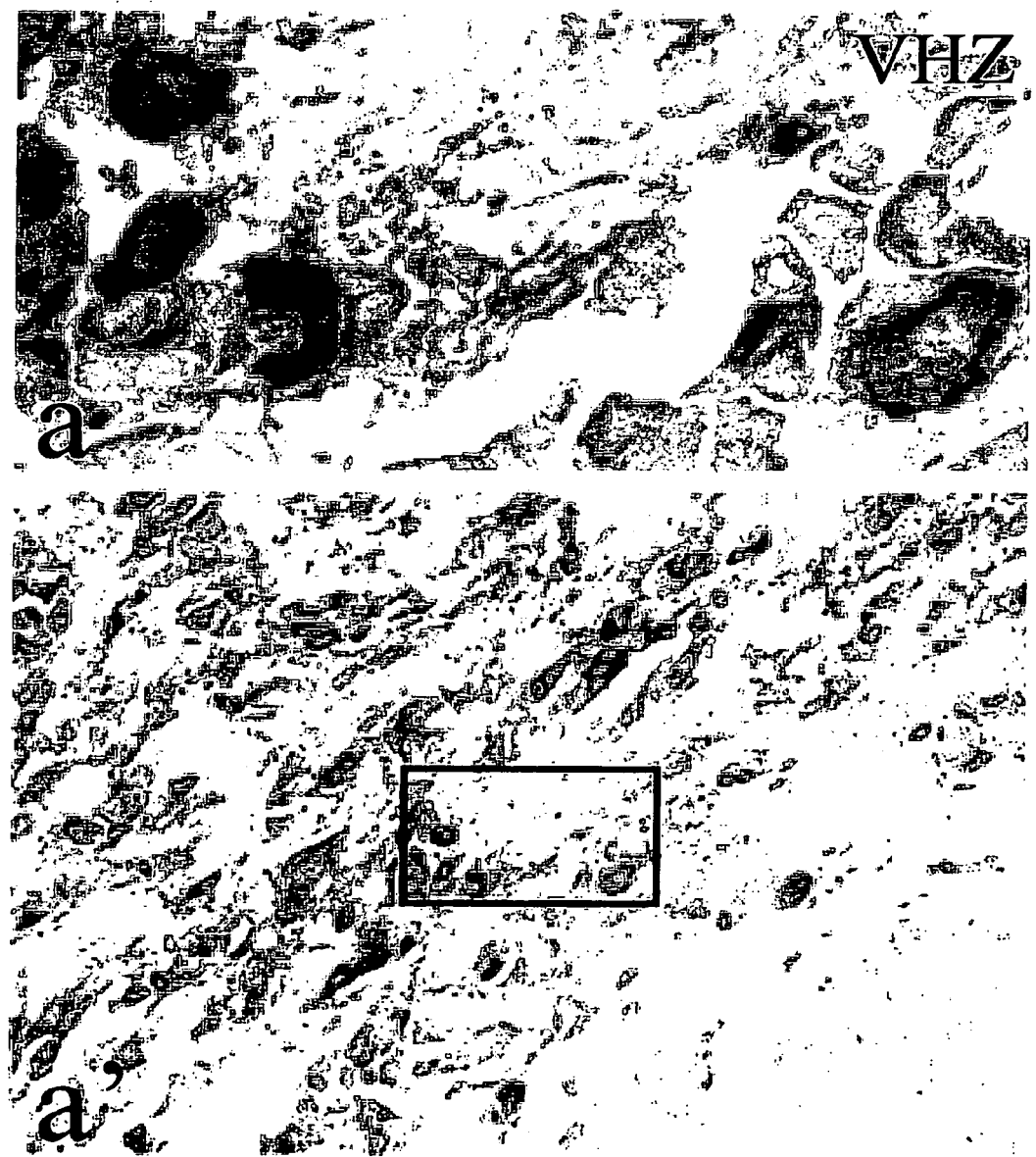
Figure 5C:
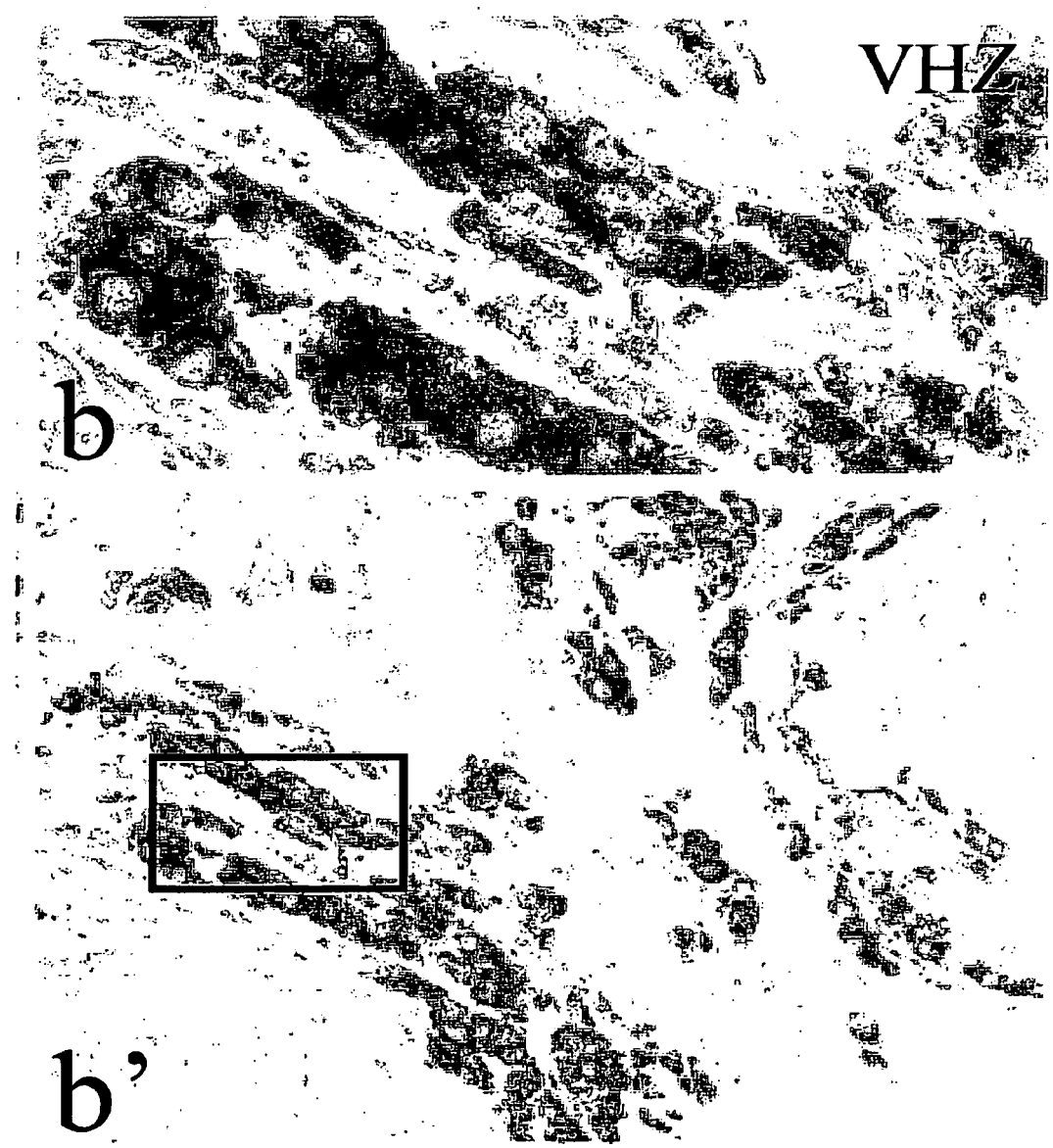
Figure 5C:
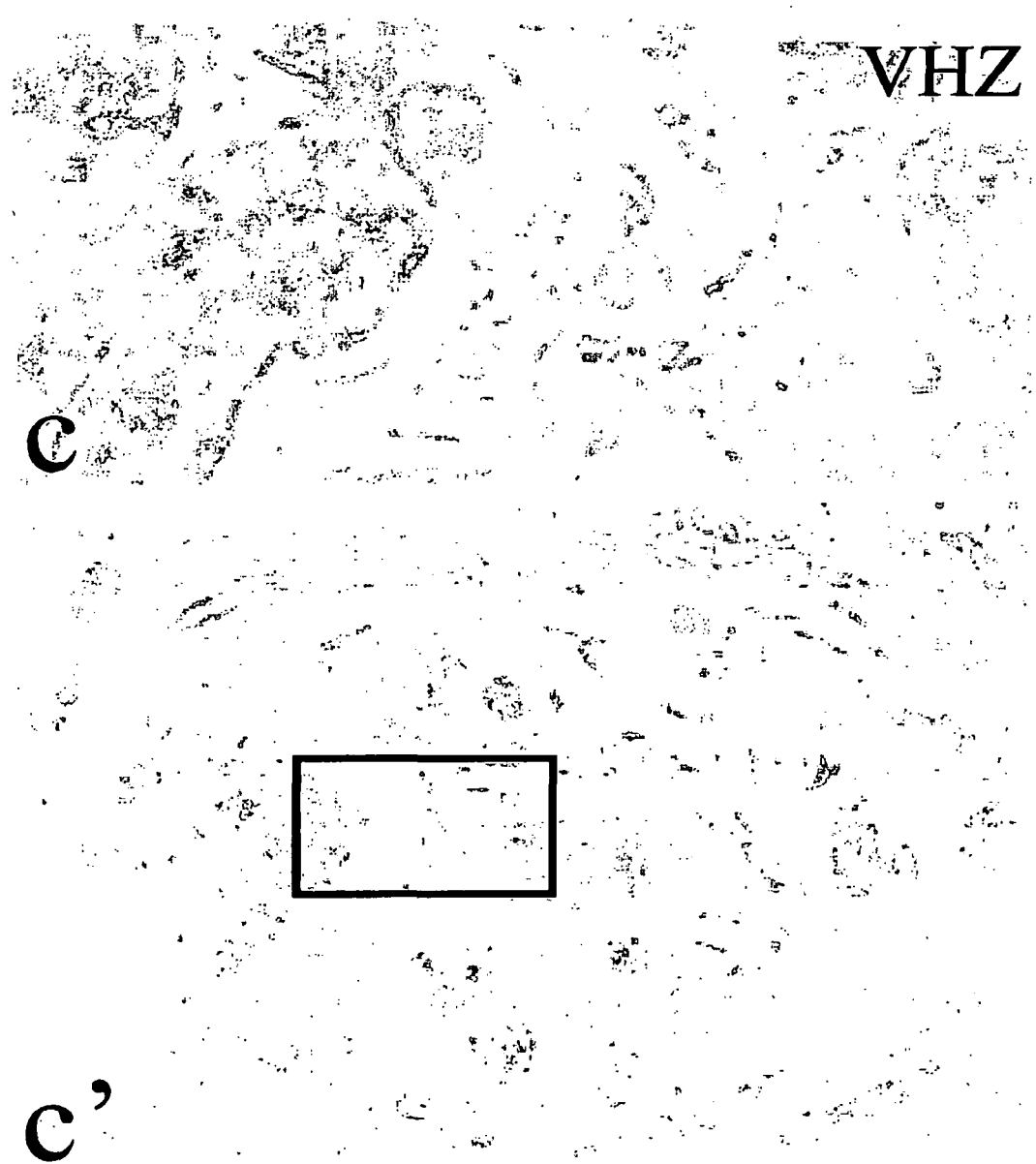
Figure 8A:
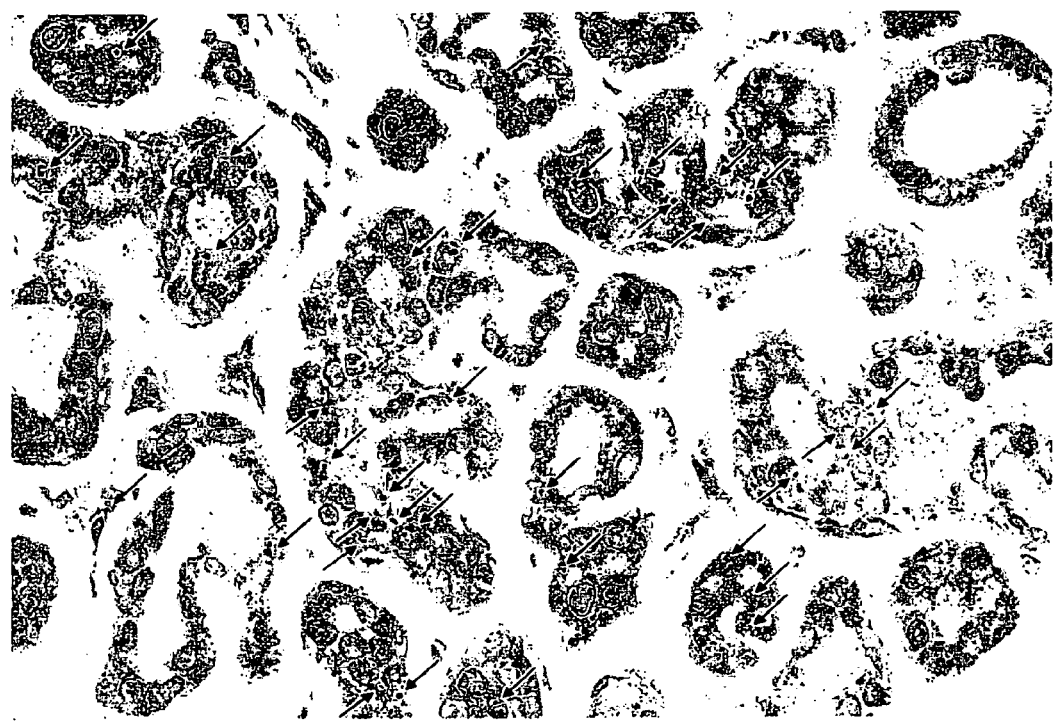
FIG. 8A and FIG. 8B are figures showing that VHZ protein is overexpressed in the centrosome and in the cytoplasm of breast cancers by immunohistochemistry FIG. 8A. Overexpression of VHZ protein is revealed in the centrosome of breast cancer. Centrosomes are indicated by black arrows (magnification ×400)
Figure 8B:
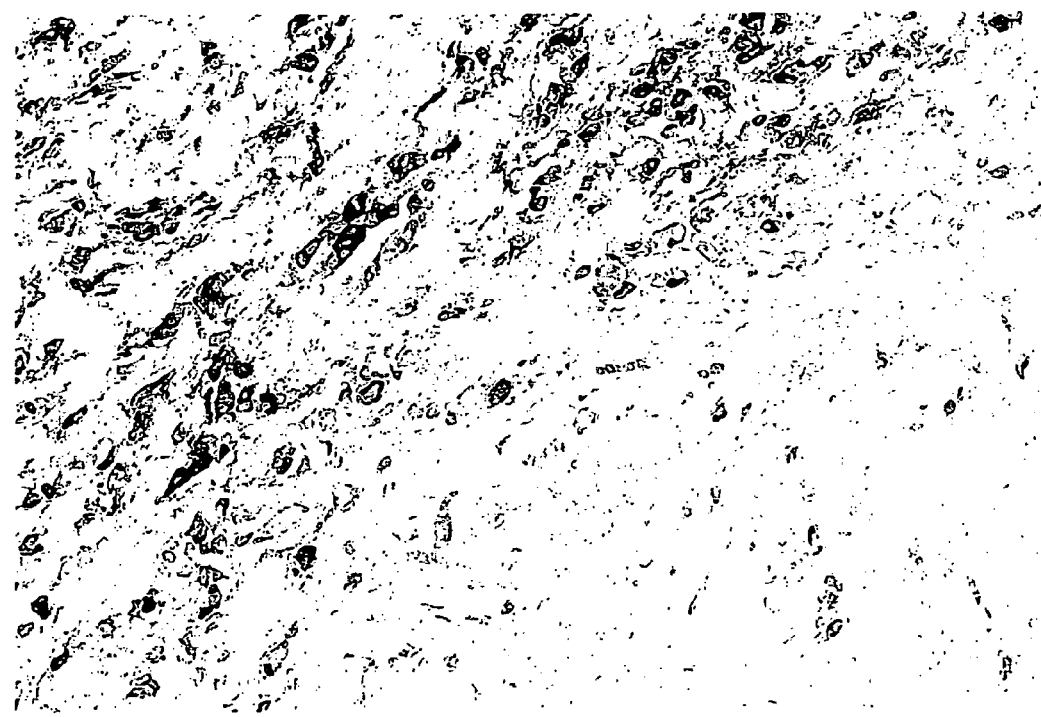

Overproduced VHZ Protein is Found Either in the Centrosome (~10%) or In the Cytoplasm (~17%) of Epithelia in Human Breast Cancers VHZ shares 28% amino acid sequence similarity with PRL-3 phosphatase. Based on the fact that PRL-3 is a phosphatase associated with metastasis of colorectal cancer (Saha et al., 2001), we hypothesized that VHZ phosphatase might have similar functions involved in metastasis of some cancers. To investigate the relationship between VHZ and multiple human cancer specimens, affinity-purified anti-VHZ rabbit antibody is used for immunohistochemistry to assess VHZ protein expression. We found that VHZ overexpression is preferentially associated with breast cancer. Out of 65 breast cancer samples (30 IDC/ILC stage I, 35 IDC stage II), 6 expressed high levels of VHZ protein in the centrosome, which is demonstrated both by double immunofluorescence with rabbit anti-VHZ and a centrosomal marker mouse anti-γ-tubulin on the same section of the cancer sample (FIG. 5A) and by single immunohistochemistry with either rabbit anti-VHZ antibody or mouse anti-γ-tubulin antibody on two adjacent sections (FIG. 5B, Panels A-B). Both immunofluorescence and immunohistochemistry confirmed that VHZ is overexpressed in the centrosome of some breast cancer samples diagnosed as invasive ductal carcinoma (IDC) or invasive lobular carcinoma (ILC) Stage I (FIG. 8A). Other than the centrosomal staining of VHZ, we found an alternate staining pattern of VHZ in different subset of breast cancer samples diagnosed as IDC Stage II. Out of 65 breast cancer samples, 11 showed high levels of VHZ protein distributed throughout the cytoplasm of spread epithelial tumor cells that displayed a fibroblast-like morphology (FIG. 5C, Panels A-B) (FIG. 8B).

Example 18

Figure 6A:
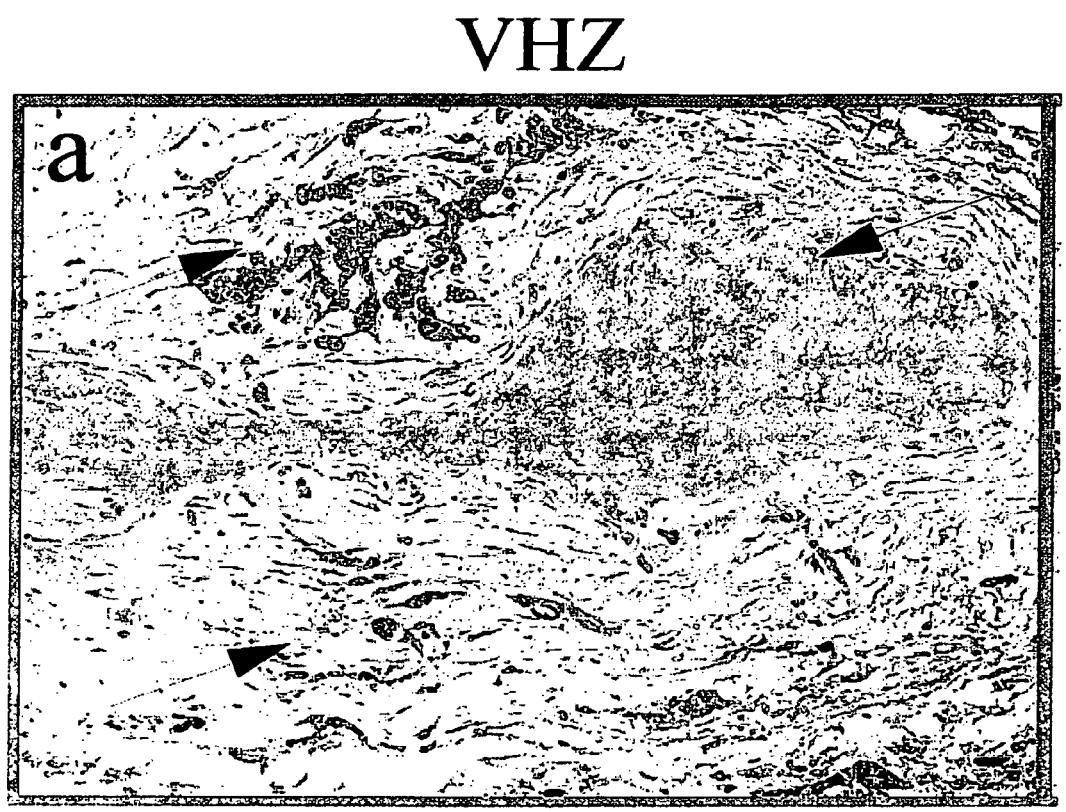
FIG. 6A and FIG. 6B are figures showing that VHZ expression in E-cadherin negative cells and overexpression of VHZ enhances motility of MCF-7 cells.
Figure 6A:
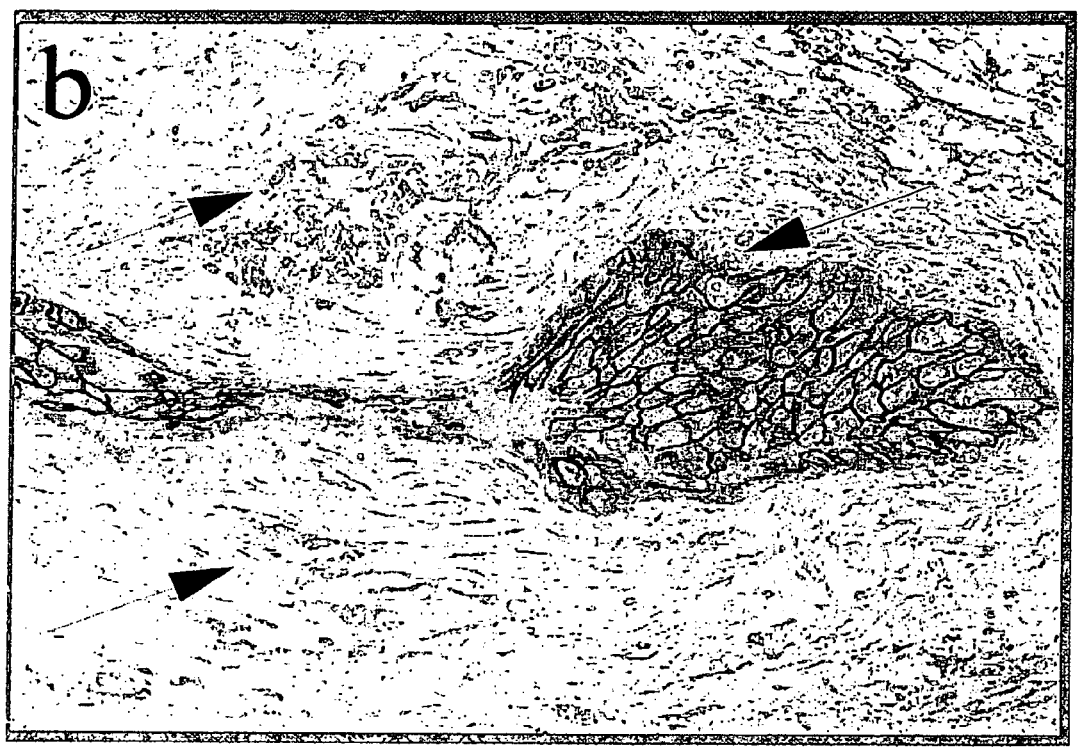

Overexpression of VHZ is Correlated with the Loss of E-cadherin Expression in Breast Cancers Since we captured an unexpected phenomenon within some microenvironments where VHZ protein is specifically overexpressed in spread fibroblast-like cells of breast cancer samples, we investigated if these cells are undergoing Epithelial-Mesenchymal transition (EMT). EMT occurs during embryonic development and oncogenesis, in which epithelial cells acquire fibroblast-like properties and lose epithelial cells adhesion and cytoskeletal components (Thiery and Sleeman, 2006). The loss of E-cadherin results in disassembly of cell-cell adhesion junctions and increased tumor cell invasiveness in vivo and is a hallmark of EMT (Kang et al., 2004). We observed that the majority of VHZ overexpressing cells (red arrows indicated) had lost the expression of E-cadherin (black arrows indicated) (FIG. 6A), suggesting that these cancer cells might have undergone through EMT process.

Example 19

Overexpression of VHZ in MCF-7 Cells Enhances Cell Migration

Figure 6B:
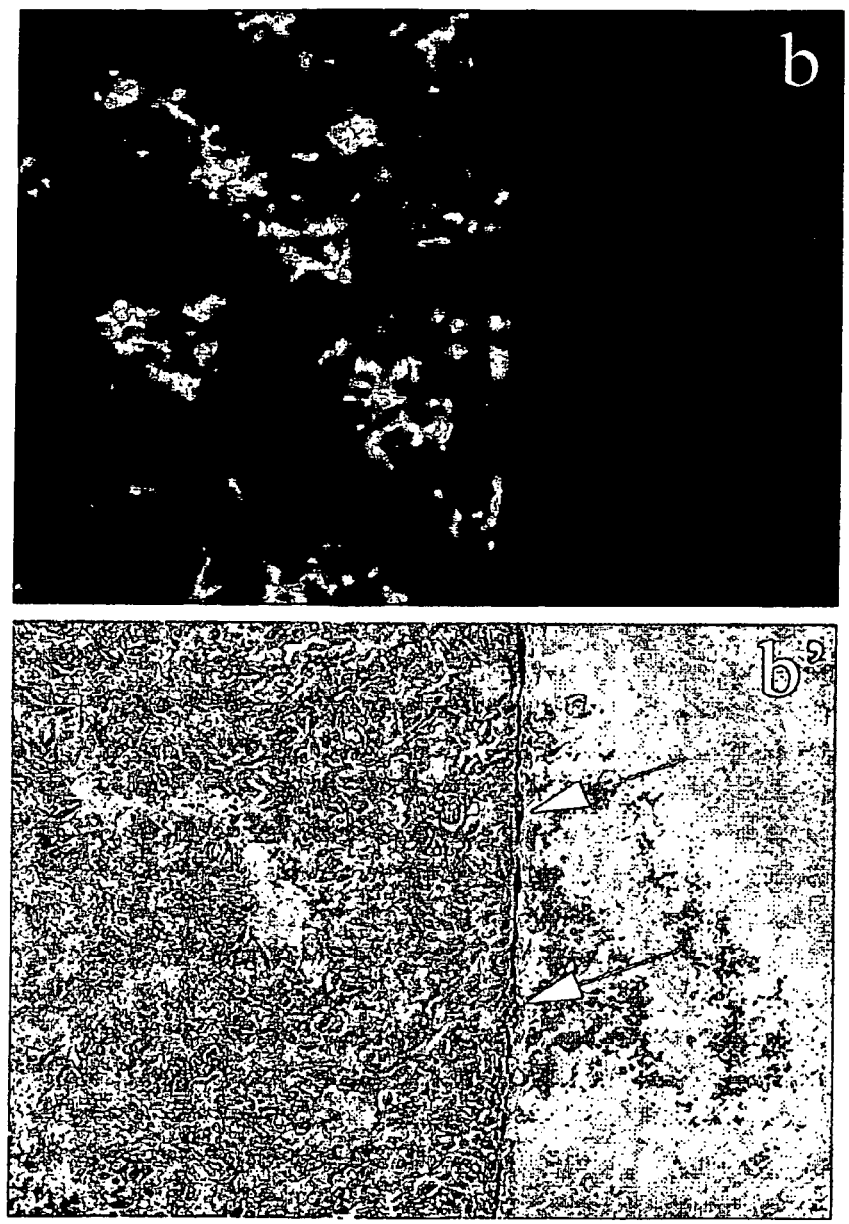
Figure 7A:
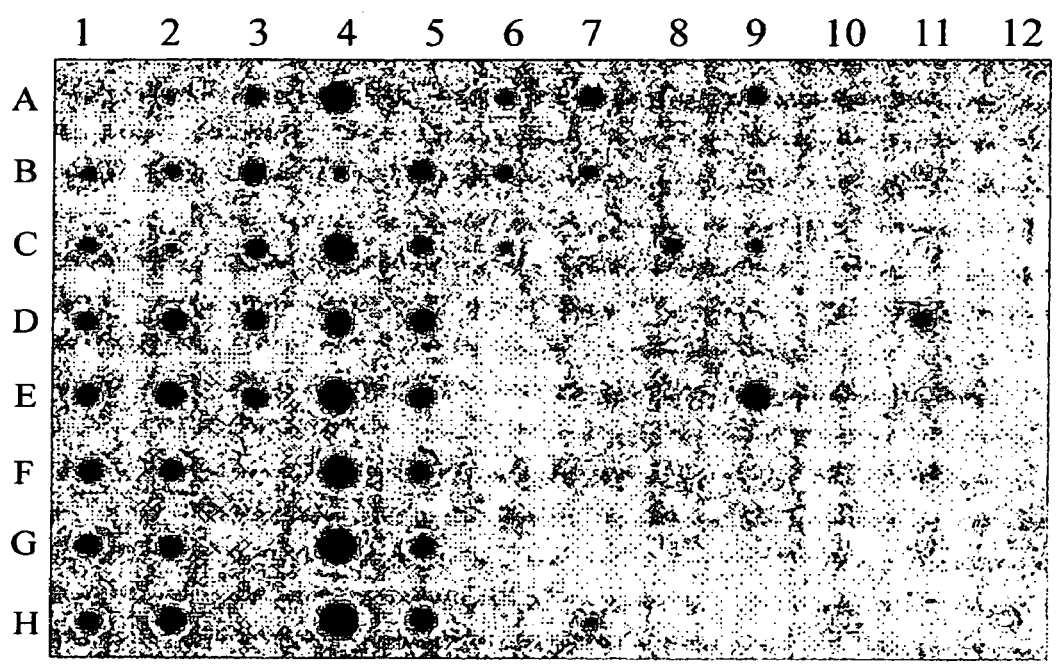
Figure 10:
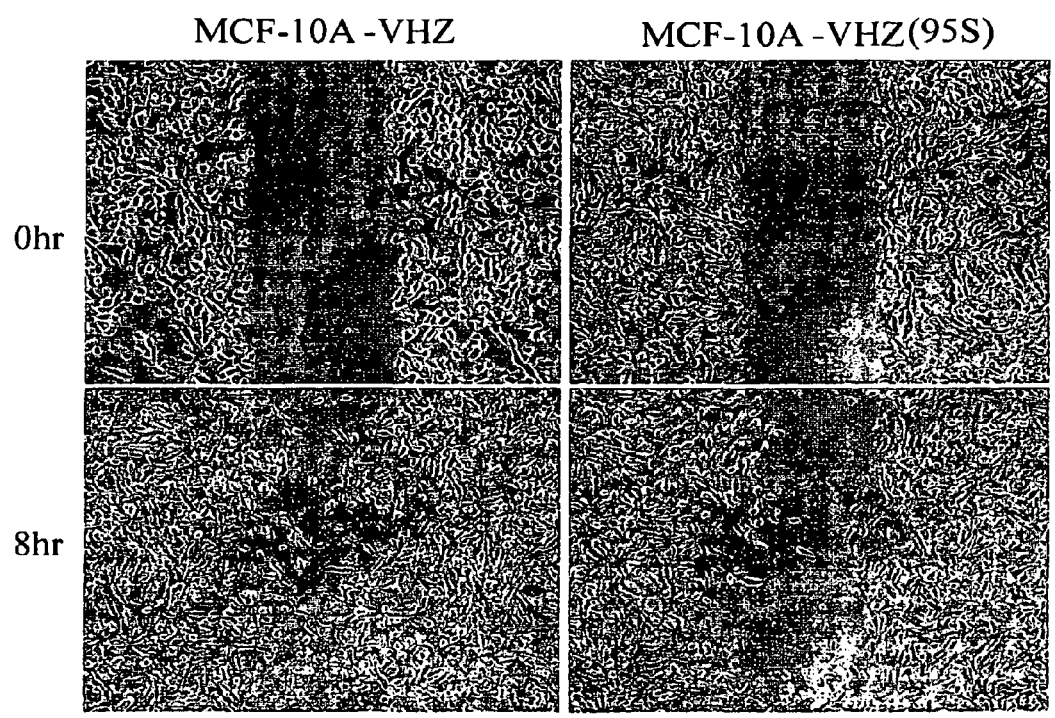
FIG. 10 is a figure showing that by wound-healing assay, MCF10A cells expressing VHZ displayed enhanced migratory property than MCF10A cells expressing VHZ(C95S). We have expressed VHZ and VHZ(C95S) in MCF10A cells ($5×10^5$) via retrovirus-mediated transduction using pBABEpuro vector. MCF10A cells expressing VHZ displayed enhanced migratory property than MCF10A cells expressing VHZ(C95S) by wound-healing assay. The clear differences in cell migration at the beginning (0 hr upper panels) and at the end point (8 hr lower panels) can be observed.

Since VHZ appeared to be associated with EMT during breast cancer progression, we then tested if VHZ could play a role in triggering cancer cell migration. To study cell mobility driven by VHZ, MCF-7 cells expressing VHZ-EGFP, or VHZ(C95S)-EGFP are examined for cell migratory properties. As migration of MCF-7 cells is difficult to measure using the conventional wound-healing or Transwell chamber assays, we used an alternative 'Inverted Coverslip' assay previously described (Sherri et al., 2006). As shown, MCF-VHZ cells migrated out from the coverslip (FIG. 6B, Panel A' white arrows) but MCF-VHZ(C95S) cells remain within the coverslip (FIG. 6B, Panel B' white arrows). The results suggest that VHZ is able to promote cell motility. The property of VHZ in promoting cell migration is further investigated using immortalized human mammary epithelia-MCF10A cells (FIG. 10).

Example 20

Discussion

We have shown that VHZ is a novel centrosomal phosphatase. The centrosome is an organelle that plays a key role in cell-cycle progression and cell division. It organizes microtubule arrays throughout the cell cycle and plays a pivotal role in regulating cell division in meiotic and mitotic cells. Deregulation of the centrosome organelle is linked to human genetic diseases and cancer. Indeed, many human tumors show centrosome aberrations (Doxsey, 2001; Nigg, 2002).

Figure 4B:
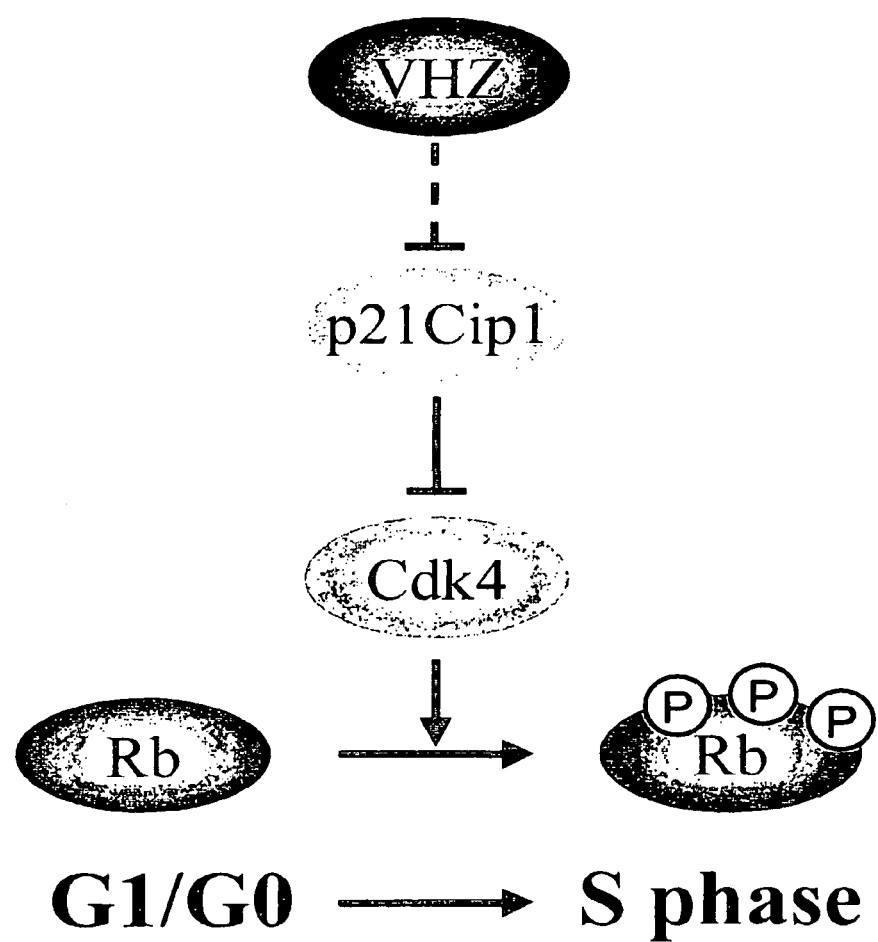

Our results of VHZ overexpression in MCF-7 cells and in NRK cells support the conclusion that VHZ phosphatase may play a role in facilitating G1/S transition during the cell cycle progression. In an attempt to address the mechanistic roles of VHZ in promoting MCF-7 cell growth; several important molecules that play critical roles in G1/S cell cycle control are examined. We found that VHZ overexpression could downregulate the tumor suppressor protein p21 Waf1/Cip1, an inhibitor of cell cycle progression. p21 Waf1/Cip1 serves to inhibit kinase activity and blocks progression through G1/S (Pestell et al., 1999). The downregulation of p21 Waf1/Cip1 by VHZ might release the inhibition of p21 on cyclin dependent kinases (Cdk) 4 (Sherr and Roberts, 1999). Consistent with this, we found that VHZ could upregulate Cdk4 expression. Eukaryotic cell cycle progression is dependent, in part, on the tightly regulated activity of CDKs. The activation of Cdk4 could target retinoblastoma protein Rb for phosphorylation (Lukas, et al., 1996). As a consequence, VHZ cause indirectly enhancement of Rb phosphorylation. The hyperphosphorylation of Rb is known to inactive the function of Rb in controlling progression through the restriction point within the G1-phase of the cell cycle (Lukas, et al., 1996, Sherr, 1996). Thus, VHZ overexpression could overcome the G1/S phase restriction point indirectly via Rb inactivation. Although future studies are needed, our results enabled us to propose a working model for VHZ's role in cell cycle progression (FIG. 4B).

In some breast cancer samples, we found overexpression of VHZ protein either in the centrosome (~10%) or in the cytoplasm (~17%) of epithelial tumor cells. VHZ is more often overexpressed in cancer cells that displayed migratory fibroblast-like morphology. We observed that VHZ-centrosomal-positive cells showed typical epithelia morphology with ILC or IDC Stage I breast cancer samples; while VHZ-cytosol-positive cells are more often associated with dispersed epithelia in IDC Stage II samples. The results might indicate that VHZ could initially be overexpressed in the centrosome and subsequently throughout the entire cytosol of the tumor cells that acquired cell motility. Significantly, the strongly stained VHZ-cytosol-positive cells are E-cadherin negative. The loss of E-cadherin plays an initial step in EMT complex process that converts epithelia into migratory mesenchymal cells (Kang et al., 2004). The loss of E-cadherin results in disassembly of cell-cell adhesion junctions and increases tumor cell invasiveness. Upregulation of VHZ might serve as one of the driving forces to initiate EMT, or to change typical epithelia phenomena to promote cell migration. Cancer cells need to acquire enhanced motility in order to overcome the barrier of the neoplastic epithelial neighborhood; leading to the invasion and outgrowth of malignant cells into new places (Thiery and Sleeman, 2006). Tumor cells infiltrate the surrounding tissue matrices in diverse patterns including both individual- and collective-cell-migration strategies (Friedl, 2003; Vogelstein and Kinzler, 2004). In our study, we showed that both individual-(FIG. 5C, Panel A) and collective-cell migrations (FIG. 5C, Panel B) are simultaneously present in VHZ-cytosol-positive cells. These phenomena might recapitulate and represent a relatively early onset of local invasion driven by VHZ within microenvironments in vivo. Although the precise role that VHZ plays in tumor progression and cancer cell migration is not known, our data suggests that overexpression of VHZ or its elevated activity might be a crucial early event for local invasion. Consistent with this hypothesis, we are able to show VHZ could enhance MCF-7 cell migration (FIG. 6B).

Our study here provides evidence that VHZ is a phosphatase involved in cell-cycle regulation and breast cancer progression. Our findings reveal new insight into this small phosphatase as an important target in future diagnostic and therapeutic strategy. We propose that inhibition of VHZ could be the basis for a therapeutic approach to block the spread of breast cancer metastasis at an early stage.

REFERENCES

Polyak K. On the birth of breast cancer. Biochim Biophys Acta. 2001 1552(1):1-13. Review Singapore Cancer Registry Report No. 5 "Cancer Incidence in Singapore, 1993-1997" published in the Yr 2000.

Alonso A, Burkhalter S, Sasin, J, Tautz L, Bogetz J, Huynh H et al. (2004a). The minimal essential core of a cysteine-based protein-tyrosine phosphatase revealed by a novel 16-kDa VH1-like phosphatase, VHZ. *J Biol Chem* 279:35768-35774.

Alonso A, Sasin J, Bottini N, Friedberg I, Osterman A, Godzik A et al. (2004b). Protein tyrosine phosphatases in the human genome. *Cell* 117:699-711.

Bessette DC, Qiu D, Pallen C J. (2008). PRL PTPs: mediators and markers of cancer progression. Cancer Metastasis Rev DOI 10.1007/s10555-008-9121-3.

Doxsey S. (2001). Re-evaluating centrosome function. *Nat Rev Mol Cell Biol* 2:688-698.

Friedl P, Wolf K. (2003). Tumour-cell invasion and migration: diversity and escape mechanisms. *Nat Rev Cancer* 3:362-374.

Kang Y, Massague J. (2004). Epithelial-mesenchymal transitions: twist in development and metastasis. *Cell* 118: 277-279.

Li J, Guo K, Koh V W, Tang J P, Gan B Q, Shi H, Li H X, Zeng Q. (2005). Generation of PRL-3- and PRL-1- specific monoclonal antibodies as potential diagnostic markers for cancer metastases. *Clin Cancer Res* 11:2195-2204.

Lukas J, Bartkova J, Bartek J. (1996). Convergence of mitogenic signalling cascades from diverse classes of receptors at the cyclin D-cyclin-dependent kinase-pRb-controlled G1 checkpoint. *Mol Cell Biol* 16:6917-6925.

Nigg E A. (2002). Centrosome aberrations: cause or consequence of cancer progression? *Nat Rev Cancer* 2:815-825.

Pestell R G, Albanese C, Reutens A T, Segall J E, Lee R J, Arnold A. (1999). The cyclins and cyclin-dependent kinase inhibitors in hormonal regulation of proliferation and differentiation. *Endocr. Rev* 20:501-534.

Polato F, Codegoni A, Fruscio R, Perego P, Mangioni C, Saha S et al. (2005). PRL-3 phosphatase is implicated in ovarian cancer growth. *Clin Cancer Res* 11:6835-6839.

Rahmouni, S., Cerignoli, F., Alonso, A., Tsutji, T., Henkens, R., Zhu, C., Louis-dit-Sully, C., Moutschen, M., Jiang, W. and Mustelin, T. (2006). Loss of the VHR dual-specific phosphatase causes cell-cycle arrest and senescence. *Nat Cell Biol* 8:524-531.

Saha S, Bardelli A, Buckhaults P, Velculescu V E, Rago C, St Croix B et al. (2001). A phosphatase associated with metastasis of colorectal cancer. *Science* 294:1343-1346.

Sherr C J. (1996). Cancer cell cycles. *Science* 274:1672-1677.

Sherr C J, Roberts J M. (1999). CDK inhibitors: positive and negative regulators of G1-phase progression. *Genes Dev* 13: 1501-1512.

Sherri L, Rankin M R, Karen, M M. (2006). A method to assess multiple aspects of the motile behaviour of adherent PC12 cells on applied biological substrates. *Journal of Neuroscience Methods* 156: 55-63.

Sun J P, Wang W Q, Yang H, Liu S, Liang F, Fedorov A A, Almo S C, Zhang, Z Y. (2005) "Structure and Biochemical Properties of PRL-1, a Phosphatase Implicated in Cell Growth, Differentiation, and Tumor Invasion", *Biochemistry* 44, 12009-12021.

Thiery J P, Sleeman J P. (2006). Complex networks orchestrate epithelial-mesenchymal transitions. *Nat Rev Mol Cell Biol* 7:131-142.

Tonks N K. (2006). Protein tyrosine phosphatases: from genes, to function, to disease. Nat Rev *Mol Cell Biol* 7:833-846.

Vogelstein B, Kinzler K W. (2004). Cancer genes and the pathways they control. *Nat. Med.* 10:789-799.

Wang Q, Holmes D I, Powell S M, Lu Q L Waxman J. (2002). Analysis of stromal-epithelial interactions in prostate cancer identifies PTPCAAX2 as a potential oncogene. *Cancer Lett.* 175:63-69.

Zeng, Q, Dong J M, Guo K, Li J, Tan H X, Koh V, Pallen C J, Manser E, Hong W J. (2003). PRL-3 and PRL-1 promote cell migration, invasion, and metastasis. *Cancer Res* 63:2716-2722.

Zeng Q, Si X, Horstmann H, Xu Y, Hong W J and Pallen C J. (2000). Prenylation-dependent association of protein-tyrosine phosphatases PRL-1, -2, and -3 with the plasma membrane and the early endosome. *J Biol Chem* 275:21444-21452.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of treatment, or alleviation of invasive or metastatic cancer that overexpresses VHZ (VH-1 like member Z) in an individual, the method comprising detecting overexpression of VHZ in a cell of the individual, and administering an anti-VHZ antibody to the individual if the expression of VHZ is increased relative to a reference level, wherein VHZ is a polypeptide having at least 90% sequence identity to SEQ ID NO: 2, wherein the anti-VHZ antibody is capable of binding to VHZ of SEQ ID NO: 2 and wherein the invasive or metastatic cancer cell becomes non-invasive or non-metastatic as a result.

2. The method of claim 1 wherein the cancer is breast cancer.

3. The method of claim 2 wherein the breast cancer is Invasive Ductal Carcinoma.

4. A method of treatment, or alleviation of an invasive or metastatic cancer in which VHZ is overexpressed in a subject, the method comprising administering an anti-VHZ antibody to the subject thereby inhibiting the formation of VHZ expressing tumor, wherein VHZ is a polypeptide having at least 90% sequence identity to SEQ ID NO: 2, wherein the anti-VHZ antibody is capable of binding to VHZ of SEQ ID NO: 2 and wherein the invasive or metastatic cancer cell becomes non-invasive or non-metastatic as a result.

5. The method of claim 4 wherein the activity of VHZ is downregulated in the cancer cells following administration of the anti-VHZ antibody.

6. A method of treating an invasive or metastatic cancer that overexpresses VHZ in a patient, the method comprising the steps of: (a) detecting increased VHZ expression in a cancer cell; and (b) reducing the level of VHZ in the cancer cell by administering an anti-VHZ antibody to the patient, wherein VHZ is a polypeptide having at least 90% sequence identity to SEQ ID NO: 2, wherein the anti-VHZ antibody is capable of binding to VHZ of SEQ ID NO: 2 and wherein the invasive or metastatic cancer cell becomes non-invasive or non-metastatic as a result.

7. The method of claim 6 wherein said reducing causes said cancer cell to become non-cancerous, non-invasive or non-metastatic.

* * * * *